US012531140B2

(12) United States Patent
Freeman et al.

(10) Patent No.: US 12,531,140 B2
(45) **Date of Patent: *Jan. 20, 2026**

(54) HANDLING OF AGE OF TRANSMITTED DATA IN MEDICAL DEVICE SYSTEM

(71) Applicant: ZOLL Medical Corporation, Chelmsford, MA (US)

(72) Inventors: Gary A. Freeman, Waltham, MA (US); Timothy F. Stever, Lowell, MA (US); C. Shane Reid, Denver, CO (US)

(73) Assignee: ZOLL Medical Corporation, Chelmsford, MA (US)

( * ) Notice: Subject to any disclaimer, the term of this patent is extended or adjusted under 35 U.S.C. 154(b) by 12 days.

This patent is subject to a terminal disclaimer.

(21) Appl. No.: 18/770,828

(22) Filed: Jul. 12, 2024

(65) Prior Publication Data

US 2025/0046408 A1 Feb. 6, 2025

Related U.S. Application Data

(63) Continuation of application No. 17/593,381, filed as application No. PCT/US2020/023479 on Mar. 19, 2020, now Pat. No. 12,073,928.

(Continued)

(51) Int. Cl.
*G16H 10/60* (2018.01)
*A61B 5/00* (2006.01)

(52) U.S. Cl.
CPC ........... *G16H 10/60* (2018.01); *A61B 5/0002* (2013.01); *A61B 5/002* (2013.01); *A61B 5/0022* (2013.01);

(Continued)

(58) Field of Classification Search
CPC ...... G16H 10/60; A61B 5/0002; A61B 5/002; A61B 5/0022; A61B 5/742; A61B 5/743; A61B 5/7435; A61B 5/7475; A61B 5/00
See application file for complete search history.

(56) References Cited

U.S. PATENT DOCUMENTS 5,414,644 A 5/1995 Seaman et al.
5,813,403 A 9/1998 Soller et al.

(Continued)

FOREIGN PATENT DOCUMENTS

CA 2897915 7/2014
CN 101952796 A 1/2011

(Continued)

OTHER PUBLICATIONS

European Search Report and Opinion, Europe Patent Application EP 25 15 0610, 8 pages (received Mar. 20, 2025).

(Continued)

*Primary Examiner* — Shahid Merchant
*Assistant Examiner* — David Choi
(74) *Attorney, Agent, or Firm* — Finch & Maloney PLLC

(57) ABSTRACT

An example of a system for review of clinical data includes a medical device configured to receive patient data signals from patient interface devices coupled to the medical device, and an auxiliary device configured to communicatively couple to the medical device via a communication channel and including an output device, a memory, a communication interface, and a processor configured to establish the communication channel, estimate a transmission age for the patient data, receive the patient data from the medical device via the communication channel, determine a patient data age based on at least one of the transmission age and a playback selection age, select a patient data age threshold based on a patient data context, compare the patient data age to the patient data age threshold to determine a patient data age indication, and provide the patient data and the patient data age indication at the output device.

31 Claims, 24 Drawing Sheets

Related U.S. Application Data

(60) Provisional application No. 62/822,073, filed on Mar. 22, 2019.

(52) U.S. Cl.
CPC .............. *A61B 5/742* (2013.01); *A61B 5/743* (2013.01); *A61B 5/7435* (2013.01); *A61B 5/7475* (2013.01)

(56) References Cited

U.S. PATENT DOCUMENTS

| | | | |
|---|---|---|---|
| 6,055,447 | A | 4/2000 | Weil et al. |
| 6,073,033 | A | 6/2000 | Campo |
| 6,364,834 | B1 | 4/2002 | Reuss et al. |
| 6,564,088 | B1 | 5/2003 | Soller et al. |
| 6,766,188 | B2 | 7/2004 | Soller |
| 6,820,057 | B1 | 11/2004 | Loch et al. |
| 6,990,371 | B2 | 1/2006 | Powers et al. |
| 7,188,151 | B2 | 3/2007 | Kumar et al. |
| 7,330,426 | B2 | 2/2008 | Berzosa et al. |
| 8,255,238 | B2 | 8/2012 | Powell et al. |
| 8,315,688 | B2 | 11/2012 | Ueda |
| 8,608,657 | B2 | 12/2013 | Pinto et al. |
| 8,738,129 | B2 | 5/2014 | Packer et al. |
| 8,856,729 | B2 | 10/2014 | Moore et al. |
| 8,870,742 | B2 | 10/2014 | Dlugos, Jr. et al. |
| 9,246,991 | B2 | 1/2016 | Moore et al. |
| 9,357,262 | B2 | 5/2016 | Vanduyn et al. |
| 9,392,217 | B2 | 7/2016 | Defazio et al. |
| 9,400,874 | B2 | 7/2016 | Powell et al. |
| 9,463,108 | B2 | 10/2016 | Anglada et al. |
| 9,524,569 | B2 | 12/2016 | Moore et al. |
| 9,658,756 | B2 | 5/2017 | Freeman et al. |
| 9,996,667 | B2 | 6/2018 | Moore et al. |
| 10,032,236 | B2 | 7/2018 | Hawkins et al. |
| 10,042,979 | B2 | 8/2018 | Moore et al. |
| 10,068,057 | B2 | 9/2018 | Moore |
| 10,111,591 | B2 | 10/2018 | Dyell et al. |
| 10,262,382 | B2 | 4/2019 | Moore et al. |
| 10,282,518 | B2 | 5/2019 | Powell et al. |
| 10,300,293 | B2 | 5/2019 | Dascoli et al. |
| 10,349,875 | B2 | 7/2019 | Freeman et al. |
| 2002/0070957 | A1 | 6/2002 | Trajkovic et al. |
| 2004/0051721 | A1 | 3/2004 | Ramseth |
| 2004/0054261 | A1 | 3/2004 | Kamataki et al. |
| 2004/0204635 | A1 | 10/2004 | Scharf et al. |
| 2006/0173501 | A1 | 8/2006 | Stickney et al. |
| 2006/0229557 | A1 | 10/2006 | Fathallah et al. |
| 2008/0261192 | A1 | 10/2008 | Huang et al. |
| 2009/0073114 | A1 | 3/2009 | Bay et al. |
| 2010/0131293 | A1 | 5/2010 | Linthicum et al. |
| 2010/0235782 | A1 | 9/2010 | Powell et al. |
| 2011/0055720 | A1 | 3/2011 | Potter et al. |
| 2011/0172550 | A1 | 7/2011 | Martin et al. |
| 2011/0246235 | A1 | 10/2011 | Powell et al. |
| 2012/0123223 | A1 | 5/2012 | Freeman et al. |
| 2012/0191464 | A1 | 7/2012 | Stuart et al. |
| 2012/0253847 | A1 | 10/2012 | Dell Anno et al. |
| 2012/0278099 | A1 | 11/2012 | Kelly et al. |
| 2012/0310059 | A1 | 12/2012 | Pinto et al. |
| 2013/0145236 | A1 | 6/2013 | Baker |
| 2013/0271469 | A1 | 10/2013 | Moore et al. |
| 2013/0275145 | A1 | 10/2013 | Moore et al. |
| 2013/0332195 | A1 | 12/2013 | Galuten |
| 2014/0201627 | A1 | 7/2014 | Freeman et al. |
| 2014/0249855 | A1 | 9/2014 | Moore |
| 2014/0278488 | A1 | 9/2014 | Moore |
| 2015/0019236 | A1* | 1/2015 | Boyer ...................... G16Z 99/00 705/2 |
| 2015/0088549 | A1 | 3/2015 | Moore et al. |
| 2015/0178457 | A1 | 6/2015 | Grimley et al. |
| 2015/0227694 | A1 | 8/2015 | Grimley |
| 2015/0374328 | A1 | 12/2015 | Ginestet et al. |
| 2016/0058287 | A1 | 3/2016 | Dyell et al. |
| 2016/0135706 | A1 | 5/2016 | Sullivan et al. |
| 2016/0303389 | A1 | 10/2016 | Peterson et al. |
| 2017/0193182 | A1 | 7/2017 | Mihai |
| 2017/0231508 | A1 | 8/2017 | Edwards et al. |
| 2017/0249435 | A1 | 8/2017 | Lancelot |
| 2017/0293726 | A1 | 10/2017 | Freeman et al. |
| 2017/0300653 | A1 | 10/2017 | Hresko et al. |
| 2018/0200142 | A1 | 7/2018 | Freeman et al. |
| 2018/0235537 | A1 | 8/2018 | Whiting et al. |
| 2018/0242875 | A1 | 8/2018 | Volpe et al. |

FOREIGN PATENT DOCUMENTS

| | | | |
|---|---|---|---|
| CN | 102833307 | A | 12/2012 |
| CN | 104335211 | A | 2/2015 |
| JP | 2002-263070 | A | 10/2005 |
| JP | 2007-233850 | A2 | 9/2007 |
| JP | 2008-301984 | A2 | 12/2008 |
| JP | 2009-039357 | A2 | 2/2009 |
| JP | 2009-233042 | A2 | 10/2009 |
| JP | 2010-217153 | A2 | 9/2010 |
| JP | 2011-036371 | A2 | 2/2011 |
| WO | WO2006001055 | A1 | 1/2006 |
| WO | WO2011116340 | A2 | 9/2011 |
| WO | WO2011122402 | A1 | 10/2011 |
| WO | WO2012017342 | A1 | 2/2012 |
| WO | WO2012065131 | A1 | 5/2012 |
| WO | WO2012065167 | A1 | 5/2012 |
| WO | WO2012148934 | A1 | 11/2012 |
| WO | WO2014110280 | A2 | 7/2014 |

OTHER PUBLICATIONS

Zoorob, et al., "Acute Dyspnea in the Office", American Family Physician, 68(9): 1803-1811, Nov. 1, 2003, 6 pages.

Hernandez, et al., "C.A.U.S.E.: Cardiac Arrest Ultra-Sound Exam—A Better Approach to managing Patients in Primary Non-Arrhythmogenic Cardiac Arrest", Resuscitation, 76(2): 198-206, Feb. 2008, Published online Sep. 6, 2007.

People's Republic of China Patent Application 202080036864.2, Office Action dated Apr. 26, 2024.

PCT Search Report and Written Opinion for PCT Application No. PCT/US2020/023479 dated Jun. 19, 2020 , 17 pages.

* cited by examiner

HANDLING OF AGE OF TRANSMITTED DATA IN MEDICAL DEVICE SYSTEM

CROSS-REFERENCE TO RELATED APPLICATIONS

This application is a continuation of U.S. patent application Ser. No. 17/593,381 (filed 17 Sep. 2021), which was the National Stage of International Application PCT/US2020/023479 (filed 19 Mar. 2020), which claims the benefit of U.S. Provisional Patent Application 62/822,073 (filed 22 Mar. 2019). All subject matter set forth in the above referenced applications is hereby incorporated by reference in its entirety into the present application as if fully set forth herein.

BACKGROUND

Caregivers, rescuers, and supervisory medical personnel evaluate patient data collected during a patient treatment, for example an emergency medical encounter, in order to determine and provide appropriate patient treatments and to evaluate the efficacy of those treatments. A user interface configured to provide the patient data at a device separate from the medical device collecting the data may enhance this evaluation. The medical device may transmit the patient data to the separate device providing the user interface via one or more short-range and/or long-range communication channels. The reviewed data may include physiological data for the patient such as electrocardiograms, heart rate, blood pressure, and other indicators necessary for the provision of effective treatment.

SUMMARY

An example of a system for review of clinical data according to the disclosure includes a medical device configured to receive signals indicative of patient data from one or more patient interface devices coupled to the medical device, and at least one auxiliary device configured to communicatively couple to the medical device via a communication channel, the at least one auxiliary device including at least one output device, a first memory, a first communication interface, and at least one first processor coupled to the first memory, the at least one output device, and the first communication interface, wherein the at least one first processor is configured to establish the communication channel with the medical device, estimate a transmission age for the patient data, receive the patient data from the medical device via the communication channel, determine a patient data age based on at least one of the transmission age and a playback selection age, select a patient data age threshold from a plurality of patient data age thresholds based on a patient data context, compare the patient data age to the patient data age threshold to determine an indication of the patient data age, and control the at least one output device to provide the patient data and the indication of the patient data age.

Implementations of such a system may include one or more of the following features. The patient data may include waveform data. The transmission age may include one or more of a medical device data communications time, an auxiliary device data communications time, and a communication channel latency. The patient data may include discrete data and the transmission age may include one or more of a medical device data communications time, an auxiliary device data communications time, a communication channel latency, and a data display duration time. One or more of the medical device and the at least one auxiliary device may be configured to estimate a round-trip time (RTT) for the communication channel in response to the establishment of the communication channel and determine the transmission age based at least in part on the RTT. The at least one auxiliary device may be configured to update a previously determined transmission age. The at least one auxiliary device may be configured to update the previously determined transmission age based on a buffer depth of a reception buffer. The at least one auxiliary device may be configured to update the previously determined transmission age in response to the receipt of the patient data from the medical device. The at least one auxiliary device may be configured to update the previously determined transmission age in coordination with a screen refresh at the at least one auxiliary device. The at least one auxiliary device may be configured to capture the playback selection age via user input to the at least one auxiliary device. The patient data age may be a combination of the transmission age and the playback selection age. The first memory may include at least one look-up table that may include the plurality of patient data age thresholds. Each patient data age threshold of the plurality of patient data age thresholds corresponds to a particular patient data context. The at least one first processor may be configured to select the patient data age threshold based on the at least one look-up table. The patient data age threshold may be a range of acceptable patient data ages. The patient data age threshold may be a maximum acceptable patient data age. The patient data context may correspond to at least one of a patient data type and a machine state of the medical device. The at least one first processor may be configured to identify the patient data type. The patient data type may include one of ECG data, gas flow data, gas pressure data, CPR data, capnography data, pulse oximetry data, blood pressure data. The patient data type may include ECG data indicative of a particular physiological condition. The particular physiological condition may include ventricular fibrillation, ventricular tachycardia, or atrial fibrillation. The patient data context may correspond to a particular combination of the machine state of the medical device and the patient data type. The machine state of the medical device may indicate one or more of a machine configuration or an operational mode. The at least one first processor may be configured to identify the machine state of the medical device. The at least one first processor may be configured to detect a change in the machine state of the medical device from first machine state to a second machine state that is different from the first machine state. The at least one first processor may be configured to detect the change in the machine state based on machine state information provided with the patient data. The first machine state may correspond to a first patient data age threshold and the second machine state may correspond to a second patient data age threshold. The at least one first processor may be configured to compare the patient data age to the first patient data age threshold when the medical device is in the first machine state and to compare the patient data age to the second patient data age threshold in response to the medical device changing from the first machine state to the second machine state. The at least one first processor may be configured to determine a relative location of the medical device and the at least one auxiliary device and select the patient data age threshold based on the relative location. The relative location of the medical device and the at least one auxiliary device may include a proximate relative location or a remote relative location. The plurality of patient data age thresholds may include a first plurality of patient data age thresholds for the proximate relative location and a second plurality of patient data age thresholds for the remote relative location. The first memory may include at least a first look-up table that may include the first plurality of patient data age thresholds for the proximate relative location and a second look-up table that may include the second plurality of patient data age thresholds for the remote relative location. The at least one first processor may be configured to determine the relative location based on one or more characteristics of the communication channel. The at least one output device may include a display screen and the indication of the patient data age may include one or more user interface features indicative of a comparison between the patient data age and the patient data age threshold. The one or more user interface features may include a textual indication of the patient data age. The one or more user interface features may include a change in an appearance of the patient data at the at least one auxiliary device. The change in the appearance of the patient data may include one or more of a change from a solid line to a broken line, a change in gray scale, and a change in color. The change in the appearance of the patient data may include a change from continuously displayed data to blinking data. The one or more user interface features may include a pop-up window that may include additional patient data with a patient data age below the patient data age threshold. The at least one output device may include a speaker. The indication of the patient data age may include an audible indication. The at least one first processor may be configured to control the at least one output device to provide one or more indications of a deterioration of data transmission through the communication channel. The at least one output device may include a display screen and the one or more indications of the deterioration of data transmission through the communication channel may include a flat dashed line in place of the patient data. The communication channel may be one or more of a wired and a wireless communication channel. The communication channel may include a short-range communication channel. The communication channel may include a long-range communication channel. The communication channel may include at least one of a local area network, an ad hoc network, a mesh network, a cellular network, and a computer network. The medical device may be a therapeutic medical device or a patient monitor. The therapeutic medical device may be a defibrillator or a defibrillator/patient monitor. The medical device may be a defibrillator and a patient monitor configured to communicatively couple to one another. The medical device may include a second memory, a second communication interface configured to communicatively couple to the first communication interface via the communication channel, and at least one second processor coupled to the second memory and the second communication interface. The at least one second processor may be configured to receive the signals indicative of patient data from the one or more patient interface devices coupled to the medical device and provide the patient data to the second communication interface. The at least one output device may include at least one first display screen. The at least one auxiliary device may be configured to provide a first visual representation of the patient data at the at least one first display screen. The medical device may be configured to provide a second visual representation of the patient data at an at least one second display screen. The at least one auxiliary device may be a tablet computer. The medical device may be a first medical device and the at least one auxiliary device may be a second medical device. The one or more patient interface devices may include at least one of one or more therapy delivery components and one or more sensors. The one or more sensors may be one or more of a chest compression sensor, ventilation sensors, and cardiac sensing electrodes. The ventilation sensors may include one or more of spirometry sensors, flow sensors, oxygen sensors, carbon dioxide sensors, pulse oximetry sensors, capnography sensors, and combinations thereof. The one or more therapy delivery components may be electrotherapy electrodes. The patient data may include one or more of physiological data and chest compression data. The physiological data may include one or more of an electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, ultrasound images of the patient's heart, near-infrared reflectance spectroscopy data, pneumography data, and cardiography data. The chest compression data may include one or more of displacement data, velocity data, release velocity data, acceleration data, compression rate data, dwell time data, and hold time data. The medical device may include a near field communication tag configured to establish the communication channel between the medical device and the at least one auxiliary device in response to a proximate location of the at least one auxiliary device relative to the medical device. The at least one output device may include a display screen configured to provide a playback interface including a data display window configured to provide a visual representation of the patient data, an interactive timeline configured to capture first user input indicative of a time interval selection for the visual representation of the patient data, and a media navigation bar configured to capture second user input indicative of data display parameters and to control the visual representation of the patient data based on the second user input. The visual representation of the patient data may include one or more of waveforms, time trends, and discrete physiological measurements for one or more of cardiac parameters and ventilation parameters. The visual representation of the patient data may include one or more of a textual, numerical, and graphical representation of cardiopulmonary resuscitation (CPR) performance data. The CPR performance data may include one or more of a compression depth, a compression rate, a chest release indicator, a perfusion performance indicator, and a CPR time indicator. The interactive timeline may include a first time interval selector configured to indicate a start time of the visual representation of the patient data and a second time interval selector configured to indicate an end time of the visual representation of the patient data. The first time interval selector and the second time interval selector may be configured to move along the interactive timeline in response to user input. The interactive timeline may include one or more visual event indicators and may be configured to capture a user selection of at least one visual event indicator of the one or more visual event indicators. The data display window may be configured to provide the visual representation of the patient data that corresponds to the user selected at least one visual event indicator. The media navigation bar may include user interactive data display controls configured to enable a user to control playback of the patient data, the user interactive data display controls including one or more of a rewind control, a play control, a stop control, a pause control, and a fast forward control, a skip back control, and skip forward control. The at least one auxiliary device may be configured as a telemedicine auxiliary device.

An example of a system for review of clinical data includes a medical device configured to receive signals indicative of patient data from one or more patient interface devices coupled to the medical device, and at least one auxiliary device configured to communicatively couple to the medical device via a communication channel, the at least one auxiliary device including: at least one output device, a first memory, a first communication interface, and at least one first processor coupled to the first memory, the at least one output device, and the first communication interface, wherein the at least one first processor is configured to establish the communication channel with the medical device, estimate a transmission age for the patient data, receive the patient data from the medical device via the communication channel, determine a patient data age based on the transmission age and a playback selection age, select a patient data age threshold, compare the patient data age to the patient data age threshold to determine an indication of the patient data age, and control the at least one output device to provide the patient data and the indication of the patient data age.

Implementations of such a system may include one or more of the following features. The patient data may include waveform data. The transmission age may include one or more of a medical device data communications time, an auxiliary device data communications time, and a communication channel latency. The patient data may include discrete data. The transmission age may include one or more of a medical device data communications time, an auxiliary device data communications time, a communication channel latency, and a data display duration time. One or more of the medical device and the at least one auxiliary device may be configured to estimate a round-trip time (RTT) for the communication channel in response to the establishment of the communication channel and determine the transmission age based at least in part on the RTT. The at least one auxiliary device may be configured to update a previously determined transmission age. The at least one auxiliary device may be configured to update the previously determined transmission age based on a buffer depth of a reception buffer. The at least one auxiliary device may be configured to update the previously determined transmission age in response to the receipt of the patient data from the medical device. The at least one auxiliary device may be configured to update the previously determined transmission age in coordination with a screen refresh at the at least one auxiliary device. The at least one auxiliary device may be configured to capture the playback selection age via user input to the at least one auxiliary device. The patient data age may include a combination of the transmission age and the playback selection age. The first memory may include at least one look-up table that may include patient data age thresholds. Each patient data age threshold in the at least one look-up table may correspond to a particular patient data context. The at least one first processor may be configured to select the patient data age threshold based on the at least one look-up table. The patient data age threshold may be a range of acceptable patient data ages. The patient data age threshold may be a maximum acceptable patient data age. The processor may be configured to select the patient data age threshold based on a patient data context that may correspond to at least one of a patient data type and a machine state of the medical device. The at least one first processor may be configured to identify the patient data type. The patient data type may include one of ECG data, gas flow data, gas pressure data, CPR data, capnography data, pulse oximetry data, blood pressure data. The patient data type may include ECG data indicative of a particular physiological condition. The particular physiological condition may include ventricular fibrillation, ventricular tachycardia, or atrial fibrillation. The patient data context may correspond to a particular combination of the machine state of the medical device and the patient data type. The machine state of the medical device may indicate one or more of a machine configuration or an operational mode. The at least one first processor may be configured to identify the machine state of the medical device. The at least one first processor may be configured to detect a change in the machine state of the medical device from first machine state to a second machine state that may be different from the first machine state. The at least one first processor may be configured to detect the change in the machine state based on machine state information provided with the patient data. The first machine state may correspond to a first patient data age threshold and the second machine state may correspond to a second patient data age threshold. The at least one first processor may be configured to compare the patient data age to the first patient data age threshold when the medical device may be in the first machine state and to compare the patient data age to the second patient data age threshold in response to the medical device changing from the first machine state to the second machine state. The at least one first processor may be configured to determine a relative location of the medical device and the at least one auxiliary device and select the patient data age threshold based on the relative location. The relative location of the medical device and the at least one auxiliary device may include a proximate relative location or a remote relative location. The first memory may include a first look-up table that may include first patient data age thresholds for the proximate relative location and a second look-up table that may include second patient data age thresholds for the remote relative location. Each patient data age threshold in the first and second look-up tables may correspond to a particular patient data context. The at least one first processor may be configured to select the patient data age threshold from the first look-up table or the second look-up table based on the relative location. The at least one first processor may be configured to determine the relative location based on one or more characteristics of the communication channel. The at least one output device may include a display screen and the indication of the patient data age may include one or more user interface features indicative of a comparison between the patient data age and the patient data age threshold. The one or more user interface features may include a textual indication of the patient data age. The one or more user interface features may include a change in an appearance of the patient data at the at least one auxiliary device. The change in the appearance of the patient data may include one or more of a change from a solid line to a broken line, a change in gray scale, and a change in color. The change in the appearance of the patient data may include a change from continuously displayed data to blinking data. The one or more user interface features may include a pop-up window that may include additional patient data with a patient data age below the patient data age threshold. The at least one output device may include a speaker and the indication of the patient data age may include an audible indication. The at least one first processor may be configured to control the at least one output device to provide one or more indications of a deterioration of data transmission through the communication channel. The at least one output device may include a display screen and the one or more indications of the deterioration of data transmission through the communication channel comprise a flat dashed line in place of the patient data. The communication channel may be one or more of a wired and a wireless communication channel. The communication channel may include a short-range communication channel. The communication channel may include a long-range communication channel. The communication channel may include at least one of a local area network, an ad hoc network, a mesh network, a cellular network, and a computer network. The medical device may be a therapeutic medical device or a patient monitor. The therapeutic medical device may be a defibrillator or a defibrillator/patient monitor. The medical device may be a defibrillator and a patient monitor configured to communicatively couple to one another. The medical device may include a second memory, a second communication interface configured to communicatively couple to the first communication interface via the communication channel, and at least one second processor coupled to the second memory and the second communication interface. The at least one second processor may be configured to receive the signals indicative of patient data from the one or more patient interface devices coupled to the medical device, and provide the patient data to the second communication interface. The at least one output device may include at least one first display screen and the at least one auxiliary device may be configured to provide a first visual representation of the patient data at the at least one first display screen. The medical device may be configured to provide a second visual representation of the patient data at an at least one second display screen. The at least one auxiliary device may be a tablet computer. The medical device may be a first medical device and the at least one auxiliary device may be a second medical device. The one or more patient interface devices may include at least one of one or more therapy delivery components and one or more sensors. The one or more sensors may include one or more of a chest compression sensor, ventilation sensors, and cardiac sensing electrodes. The ventilation sensors may include one or more of spirometry sensors, flow sensors, oxygen sensors, carbon dioxide sensors, pulse oximetry sensors, capnography sensors, and combinations thereof. The one or more therapy delivery components may be electrotherapy electrodes. The patient data may include one or more of physiological data and chest compression data. The physiological data may include one or more of an electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, ultrasound images of the patient's heart, near-infrared reflectance spectroscopy data, pneumography data, and cardiography data. The chest compression data may include one or more of displacement data, velocity data, release velocity data, acceleration data, compression rate data, dwell time data, and hold time data. The medical device may include a near field communication tag configured to establish the communication channel between the medical device and the at least one auxiliary device in response to a proximate location of the at least one auxiliary device relative to the medical device. The at least one output device may include a display screen configured to provide a playback interface including a data display window configured to provide a visual representation of the patient data, an interactive timeline configured to capture first user input indicative of a time interval selection for the visual representation of the patient data, and a media navigation bar configured to capture second user input indicative of data display parameters and to control the visual representation of the patient data based on the second user input. The visual representation of the patient data may include one or more of waveforms, time trends, and discrete physiological measurements for one or more of cardiac parameters and ventilation parameters. The visual representation of the patient data may include one or more of a textual, numerical, and graphical representation of cardiopulmonary resuscitation (CPR) performance data. The CPR performance data may include one or more of a compression depth, a compression rate, a chest release indicator, a perfusion performance indicator, and a CPR time indicator. The interactive timeline may include a first time interval selector configured to indicate a start time of the visual representation of the patient data and a second time interval selector configured to indicate an end time of the visual representation of the patient data. The first time interval selector and the second time interval selector may be configured to move along the interactive timeline in response to user input. The interactive timeline may include one or more visual event indicators and may be configured to capture a user selection of at least one visual event indicator of the one or more visual event indicators. The data display window may be configured to provide the visual representation of the patient data that may correspond to the user selected at least one visual event indicator. The media navigation bar may include user interactive data display controls configured to enable a user to control playback of the patient data, the user interactive data display controls including one or more of a rewind control, a play control, a stop control, a pause control, and a fast forward control, a skip back control, and skip forward control. The at least one auxiliary device may be configured as a telemedicine auxiliary device.

Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

DETAILED DESCRIPTION

Figure 1A:
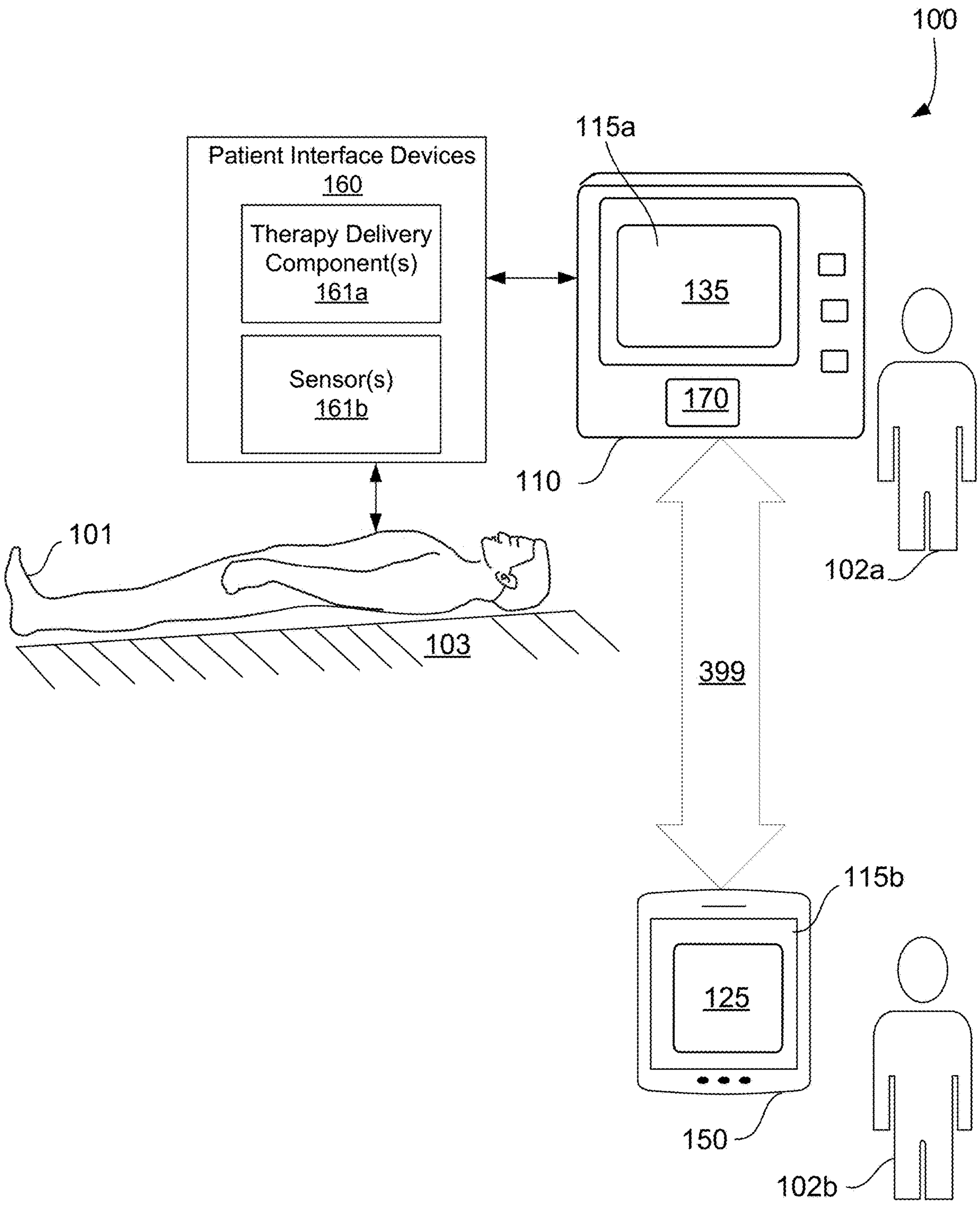
FIG. 1A shows an example of a system that provides transmission of patient data from a medical device to an auxiliary device.

During a medical event, a medical device may be used by the appropriate personnel to provide medical therapy to a patient and/or may be used to monitor the patient. The medical device may be, for example, a patient monitor, a therapeutic medical device (e.g., a defibrillator, an automated compression device, a ventilator, etc.), a therapeutic medical device/patient monitor, or a modular therapeutic medical device/patient monitor. The medical device or apparatus may be provided as one physical device (e.g., a single housing) or may be provided as multiple physical devices (e.g., modular physical devices with two or more separate housings) configured to communicatively and/or operatively couple with one another. These types of medical devices are examples only and other types and combinations of medical devices are within the scope of the disclosure. The medical device may include and/or be configured to couple to one or more patient interface devices. The patient interface devices may include one or more therapy delivery components, one or more sensors, and/or one or more combined therapy delivery/sensing components such as defibrillation electrodes configured to sense and monitor a patient's electrocardiogram (ECG) and to deliver electrotherapy. The medical device may collect patient data via the one or more patient interface devices and may provide the patient data to a user of the medical device via an operational interface. The user may be a caregiver such as a first responder, a paramedic, a physician, a nurse, a rescue worker, etc. The patient data may include physiological sensor data, clinical performance data, demographic data, etc. For example, the patient data may include clinical performance data such as CPR performance data (e.g., chest compression parameters (e.g., compression depth, compression rate, etc.)) and/or may include physiological sensor data such as respiration parameters, heart rate, blood pressure, etc. and/or physiological waveforms such as, for example, an electrocardiogram (ECG). Demographic data may include, for example, name, age, gender, address, insurance, medical provider, biometric data, etc. The patient data may also include diagnostic data, stored diagnostic data, stored event markers of clinical interventions and/or other types of event markers, historical patient health information, and/or clinical performance information. The patient data may further include information of various types (e.g., clinical performance, physiological, demographic, etc.) provided to the medical device by a caregiver (e.g., information input via a touchscreen, keyboard, microphone, soft key, etc.). These types of data are examples only and not limiting of the disclosure and are discussed in further detail below.

An auxiliary device such as another medical device or a computer tablet may provide a display for viewing patient data. For example, the auxiliary device may be a computer tablet, a server, a laptop, a mobile communication device, a patient monitor, a therapeutic medical device (e.g., a defibrillator, an automated compression device, a ventilator, etc.), a therapeutic medical device/patient monitor, or a modular therapeutic medical device/patient monitor. These types of auxiliary devices are examples only and other types and combinations of auxiliary devices are within the scope of the disclosure. The auxiliary device may be communicatively coupled to the medical device and may be located proximate to or remote from the medical device. In an implementation, the auxiliary device may collect patient data from the patient in addition to the patient data collected by the medical device.

The auxiliary device may host a playback interface. The playback interface may be a user interface at the display of the auxiliary device. The playback interface may display, re-display, and/or replay patient data transmitted to the auxiliary device from the medical device. The patient data may include current patient data and/or historic patient data. A user of the auxiliary device may request the current data and/or the historic data for display and review at the playback interface. The medical device may collect, display, and/or store the patient data transmitted to the auxiliary device. In an implementation, the medical device may control its display screen to display both the operational interface and the playback interface (e.g., in a toggle mode or shared screen mode).

As discussed in further detail below with regard to FIGS. 1B and 1C, the current data corresponds to data provided at the medical device and/or at the auxiliary device at a display time that is as close as possible to the time of the instantaneous real-time physiologic event represented by the current data. The current data may also be referred to as real-time data. The historic data, which may also be referred to as playback data corresponds to data from a user-selected time or time period prior to a current time. For example, the user may select a time period starting 5 seconds prior to the current time and view data collected over the time period spanning 5 seconds prior to the current time up to the current time. All of the data transmitted from the medical device to the auxiliary device, for example, the current data and the historic data, may have a transmission age due to various latencies associated with the transmission of data from the medical device to the auxiliary device. These latencies may delay the display of data at the auxiliary device relative to the medical device and may prevent the display of the patient data at the auxiliary device any closer in time to the instantaneous real-time physiologic event than the transmission age. These latencies may include contributions from one or more of the medical device, the auxiliary device, and the communication channel. As discussed in further detail below, the medical device and/or the auxiliary device may determine (e.g., measure or estimate) the transmission age and determine (e.g., measure or estimate) a patient data age based at least in part on the transmission age.

For the current patient data, the transmission age may determine the difference between the display time of the current patient data at the auxiliary device and the time of the instantaneous real-time physiologic event. Differences between the time of the instantaneous real-time physiologic event and the time of display at the medical device of patient data for the physiologic event may be assumed to be negligible as discussed below with regard to FIGS. 1B and 1C. Thus for the current patient data, the patient data age may be the transmission age. As one non-limiting example, if the transmission age is 1 second, then the current patient data may be displayed at the auxiliary device 1 second after the same current patient data is displayed at the medical device. For instance, an ECG feature at the display of the auxiliary device may be displayed 1 second after the same feature appears at the display of the medical device.

For the playback patient data (i.e., the historic data), a combination of the transmission age and a user selected playback age may determine the difference between the display time of the playback patient data at the auxiliary device and the time of the instantaneous real-time physiologic event. Thus, the patient data age for the playback patient data may be a sum of the transmission age and the playback age. As one non-limiting example, the user may want to view patient data during a 5 second time period prior to the current time. The user may request playback patient data for this time period. The transmission age for the requested playback patient data may be 1 second. The playback patient data corresponding to a time 5 seconds prior to the current time may have a playback age of 5 seconds in addition to the transmission age of 1 second. Thus, the playback patient data may be displayed at the auxiliary device 6 seconds after the instantaneous real-time physiologic event and 6 seconds after the medical device displayed the same data as current data.

As discussed below with regard to FIG. 1C, there may be additional contributions to the patient data age for data that is sampled intermittently. For example, the medical device may sample blood pressure at discrete time intervals, as compared with continuously sampled waveforms, like ECG.

Current data and/or playback data that is older than a threshold data age may not be clinically actionable. As discussed below in further detail, specific clinical situations may determine the threshold patient data age. A patient data age in excess of the threshold data age may render the data too far removed in time from the instantaneous real-time physiologic event to base a determination of an appropriate clinical response on this data. The threshold patient data age may depend upon the specific clinical situation and may vary between different clinical situations. The system may include pre-selected threshold patient data ages (e.g., pre-programmed based on clinical knowledge and expertise) so as to enable the system to distinguish between current data and playback data that is clinically actionable and current data and playback data that is not clinically actionable. Thus, even in a situation where the playback interface is described as providing real-time data, the various delays inherent in a data transmission configuration may limit the efficacy of this data in clinical decision making. As described in detail with regard to FIGS. 5A-5J, if the patient data age exceeds the threshold patient data age, the playback interface may provide and/or change features of the playback interface to alert the caregiver of the excessive patient data age. For example, the playback interface may change a color of provided data or may provide message for a user.

As one non-limiting example, a caregiver may request a current blood pressure measurement at the auxiliary device for a patient experiencing a myocardial infarction. However, due to the latencies of data communication, the blood pressure measurement may have a patient data age of 60 seconds. In the case of the myocardial infarction, the threshold patient data age for blood pressure may be 10-30 seconds. Thus, the blood pressure measurement with the patient data age of 60 seconds may be too old for the caregiver to determine an immediate treatment for the patient based on this reading. The treatment based on this reading may harm the patient or be ineffective in treating the patient. As described below, along with other examples, the auxiliary device may control the playback interface to warn the caregiver that the patient data age of 60 seconds exceeds the threshold patient data age of 10-30 seconds. In response, the caregiver may need to take other steps to determine the current blood pressure of the patient (e.g., request another transmission, call a bedside caregiver, re-start the auxiliary device to re-initiate the communication channel, etc.) prior to determining a clinical response to the blood pressure.

As one illustrative example of differences in acceptable patient data ages based on the specific clinical situation, consider atrial fibrillation (AF) versus ventricular fibrillation (VF). Further, consider a playback interface at a location remote from the patient and the medical device collecting the ECG from the patient. For AF monitoring, it may not adversely affect patient care to consider ECG data at the playback interface with a patient data age of 10-60 seconds as clinically actionable real-time data (e.g., the ECG data at the playback interface may be 10-60 seconds delayed relative to the same ECG data displayed at the operational interface of the medical device). However, if the ECG indicates ventricular fibrillation (VF), the medical device may enter a heart rhythm analysis mode to determine if application of a defibrillation shock is appropriate. In this case, with an imminent clinical response of the defibrillation shock, the patient data age of 10-60 seconds may be too long. The clinical response may require the caregiver to view data that is closer in time to the occurrence of the actual physiological VF event. Thus for VF, the patient data age may be 5-10 seconds in order to consider the ECG as clinically actionable real-time data.

The system described herein provides several advantages. It may be of benefit for the caregiver to review at least a portion of the patient data on an auxiliary device separate from the medical device. This may be advantageous in a crowded patient area or in a situation with multiple caregivers. This may also facilitate participation in care by remotely located caregivers, e.g., via telemedicine. The auxiliary device may provide the patient data at a playback interface configured to enable a review of the patient data in real-time and/or as historical data. In a telemedicine application, the auxiliary device may be configured for telemetric reception, analysis, review, and/or transmission of the patient data. Review of historical data in combination with real-time data may better inform the interpretation and response to the real-time data. The auxiliary device may be located locally or remotely and enable this patient data review during the ongoing medical event while the medical device is still administering therapy and/or collecting patient data from the patient and without requiring any downtime in operation of the medical device. In the case of the auxiliary device being at the remote location, a remotely located clinician with more advanced medical training compared to caregivers located at the patient site (i.e., local location) may be able to receive and interpret the up to date patient data, and provide expert guidance as if present. Determination of a clinically acceptable patient data age and indications of the data age for the caregiver may improve the clinical responses based on the patient data. For example, such indications may prevent a clinician error in providing a clinical response to data that is too old to serve as a basis for the clinical response. These indications may change dynamically based on changes in the age of the data due to changes in transmission channel characteristics and/or changes in the clinical situation. Remote viewing of data by medical personnel hundreds or thousands of miles away where channel latencies and variable playback delays may all negatively impact decision making by the remote-located experts, obviating any potential benefit these experts may provide in a medical emergency, and adversely impacting critical care survival rates.

Referring to FIG. 1A, an example of a system that provides transmission of patient data from a medical device to an auxiliary device is shown. The system 100 includes at least one medical device 110 (e.g., a first medical device) and at least one auxiliary device 150. Although shown as a tablet computer in the example of FIG. 1A, the auxiliary device 150 may be, for example, but not limited to, a server or a personal user device such as a personal computer, a laptop computer, a mobile device, a hand-held device, a wireless device, a tablet computer, a wearable device (e.g., a wrist-worn device, a head-worn device, heads up display, etc.), or combinations thereof. The auxiliary device 150 may be a group of communicatively coupled devices. Claimed subject matter is not limited to a particular type, category, size, etc. of computing device. In various implementations, the auxiliary device 150 may be a medical device (e.g., a second medical device) and/or may be a computing device adapted for medical applications. Although one medical device 110, one auxiliary device 150, and one communication channel 399 are shown in FIG. 1A, in various implementations, the system 100 may include one or more medical devices, one or more auxiliary devices, and/or one or more communication channels.

The medical device 110 may provide therapy to and/or monitor the patient 101 via the patient interface devices 160 (e.g., therapy delivery component(s) 161*a* and/or sensor(s) 161*b*). In various implementations, the auxiliary device 150 may provide therapy to and/or monitor the patient 101 via the patient interface devices 260 (e.g., therapy delivery component(s) 261*a* and/or sensor(s) 261*b*).

The patient 101 may be supported by a support surface 103. The support surface 103 may be the ground, a floor, a bed, a gurney, a cot, a wheelchair, a chair, etc. The type of support surface 103 may depend on the type of therapy being provided. A user 102*a* of the medical device 110 may be a caregiver (e.g., a first caregiver). Although shown as one user in FIG. 1A, the user 102*a* may represent multiple users (e.g., a care team) of the medical device 110. A user 102*b* of the auxiliary device 150 may be a caregiver (e.g., a second caregiver). Although shown as one user in FIG. 1A, the user 102*b* may represent multiple users (e.g., a care team) of the auxiliary device 150.

A processor of the medical device 110 (e.g., the processor 120 shown in FIG. 14) may determine and/or generate patient data based on the signals indicative of the patient data as received from the patient interface devices 160. The medical device 110 may also receive patient data via user input. The patient data is discussed in further detail below and may include physiological measurements and/or parameters for the patient, treatment performance parameters, etc. The processor 120 of the medical device 110 may control a display screen 115*a* to display the patient data at an operational interface 135. The operational interface 135 may provide the patient data in real-time as the signals are received and processed by the processor 120 of the medical device 110. In addition to the display screen 115*a*, the medical device 110 provides the patient data via one or more other output devices. For example, the processor 120 may be configured to control a speaker 170 to provide audible instructions, a metronome (e.g., a chest compression metronome), audible feedback, and/or audible physiological information for the user 102*a* of the medical device 110. As the processor of the medical device 110 processes sensor signals to determine and collect sensor data, the processor 120 may associate time stamps with the sensor data. The patient data may include the sensor data and the associated time stamps.

In an implementation, the medical device 110 may provide the patient data to the auxiliary device 150 via a communication channel 399. The auxiliary device 150 may provide the patient data received from the medical device 110 at the playback interface 125 provided at the display screen 115*b*. The playback interface 125 may provide historic patient data and current patient data based on user input.

The communication channel 399 may be a wired communication channel and/or a wireless communication channel. In an implementation, the communication channel 399 may be a short-range communication channel or a long-range communication channel. Thus, the auxiliary device 150 may be a remote device or a local device. The wired communication channel may include a wired electrical coupling, an optical coupling via an optical cable, etc. The communication channel 399 may include coupling via a radio frequency or other transmission media and/or via a network such as a local area network, an ad hoc network, a mesh network, a cellular and/or other communication network, a satellite network, and/or a computer network (e.g., an Internet Protocol (IP) network, etc.) and combinations thereof. The communication channel 399 may utilize protocols such as, for example, 802.11, ZigBee®, Bluetooth®, TCP/IP, etc. The communication channel 399 may include near field communication, for example, as implemented via a communication RFID tag. In various implementations, the communication channel 399 may provide secure and/or authenticated communication. In an implementation, the medical device 110 and/or the auxiliary device 150 may encrypt and/or decrypt the data transmitted and/or received via the communication channel 399.

The visual representations of the same patient data may be the same on both interfaces 135 and 125 or may be different. Thus, for the same real-time patient data, the images of this data generated for display at the playback interface 125 may differ from those generated for display at the operational interface 135. Thus, the visual representation of the patient data at the playback interface 125 (e.g., a first visual representation) may not be a replication of the visual representation of the same patient data at the operational interface 135 (e.g., a second visual representation).

In an implementation, the display screen 115*a* of the medical device may be configured to provide the playback interface 125 and the operational interface 135. For example, the display screen 115*a* may be configured to toggle between the two interfaces and/or provide the two interfaces simultaneously (e.g., as two windows on one screen or as a first window inset within a second window). In the simultaneous display, the display screen 115*a* may provide the operational interface 135 in a first portion of the display screen 115*a* and may provide the playback interface 125 in a second and different portion of the display screen 115*a*. The first portion and the second portion may be the same size or may be different sizes. For example, the playback interface 125 may occupy a smaller area on the display screen 115*a* than the operational interface 135. This configuration may be a default state for the medical device 110. Conversely, the operational interface 135 may occupy the smaller area on the display screen 115*a* than the playback interface 125.

Figure 14:
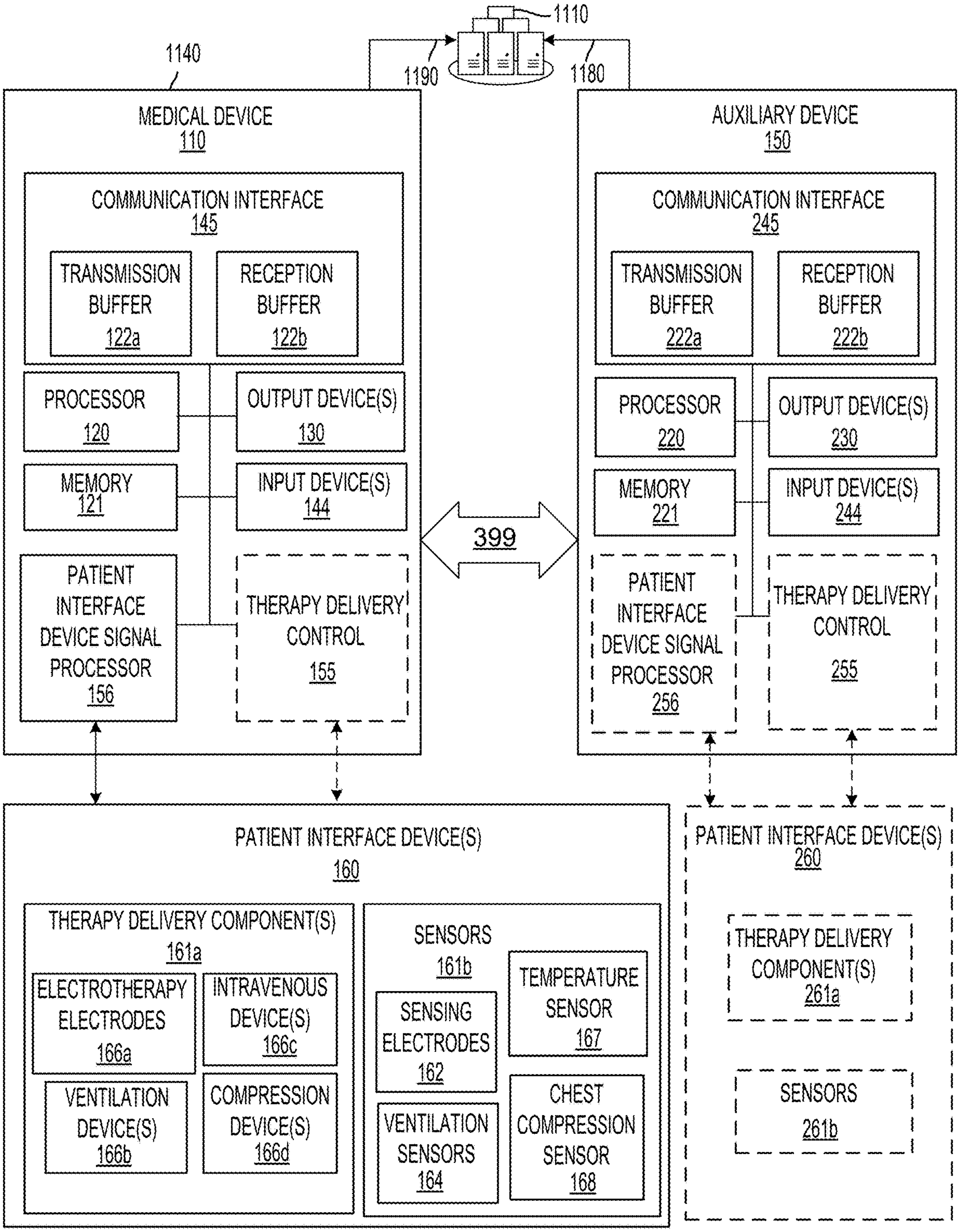
FIG. 14 shows examples of components of various devices discussed with regard to FIG. 1A.

In an implementation, the auxiliary device 150 may include and/or may be configured to couple to one or more additional patient interface devices (e.g., the patient interface devices 260 shown in FIG. 14). A processor of the auxiliary device 150 (e.g., the processor 220 shown in FIG. 14) may determine and/or generate additional patient data based on the signals from the additional patient interface devices. The auxiliary device 150 may also receive the additional patient data via user input.

Figure 1B:
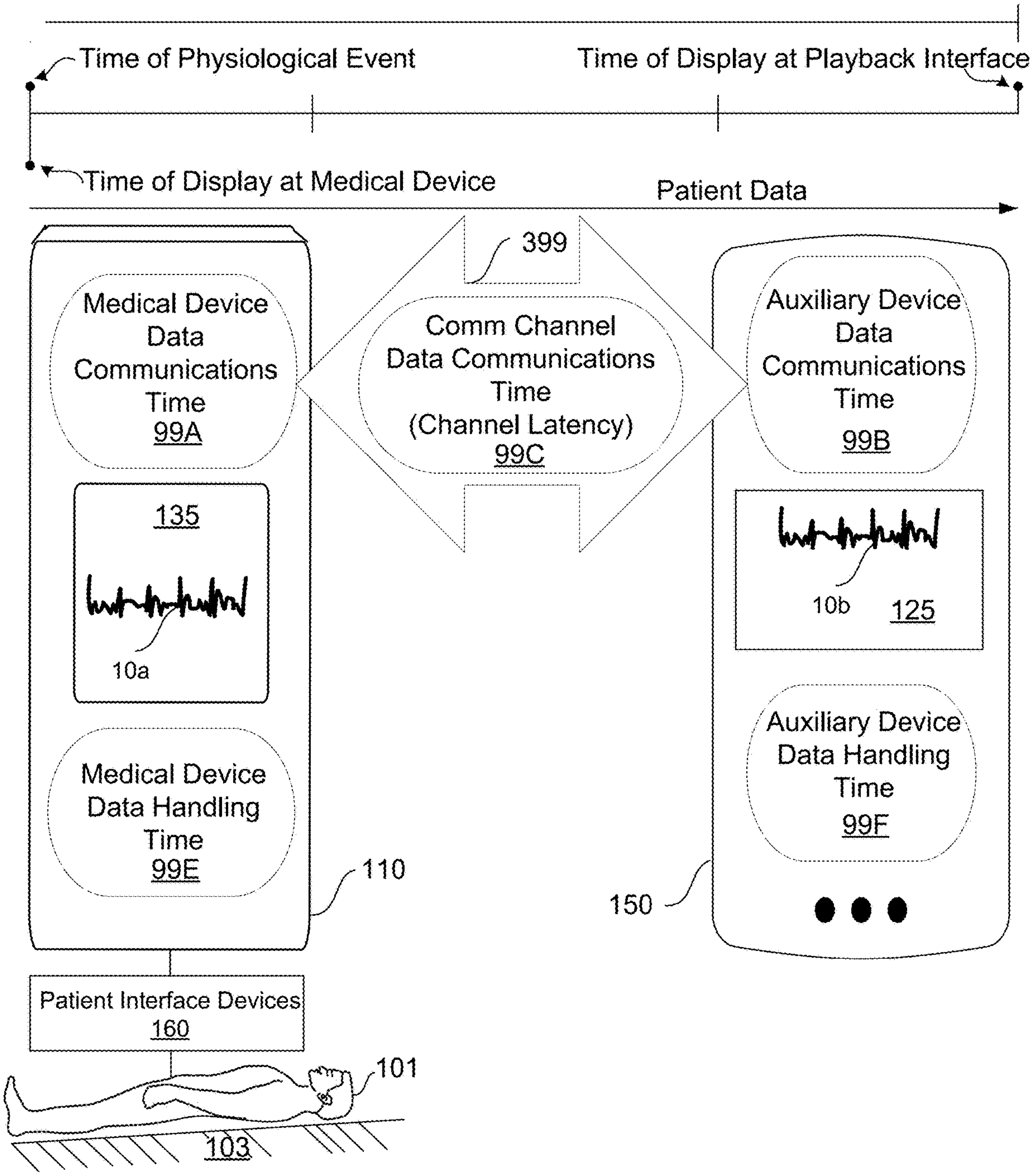
FIG. 1B is an exemplary schematic that conceptually illustrates transmission age for patient data represented as waveforms.

Referring to FIG. 1B, contributions to transmission age for waveform data are shown schematically. The medical device 110 receives patient data (e.g., patient data associated with the patient 101) via the patient interface devices 160. For example, the patient data may be waveform data 10*a* such as ECG, capnography, etc. The medical device 110 receives waveform data 10*a* as a substantially continuous analog signal converted to a digital signal at the medical device 110. The medical device 110 receives and displays the waveform data 10*a* substantially at the time of a physiological event. The waveform data 10*a* may be displayed at the operational interface 135 and streamed substantially continuously to the auxiliary device 150 for display at the playback interface 125 (e.g., the waveform data 10*b* which is a playback interface representation of the waveform data 10*a*). For the waveform data 10*a*, the time of display at the medical device 110 is substantially equal to the time of the physiological event. For example, the physiological event for ECG data is the electrical activity of the heart at the time as a function of time. Thus, each moment in time provides new ECG data that is continuously streamed to the auxiliary device 150.

Figure 1C:
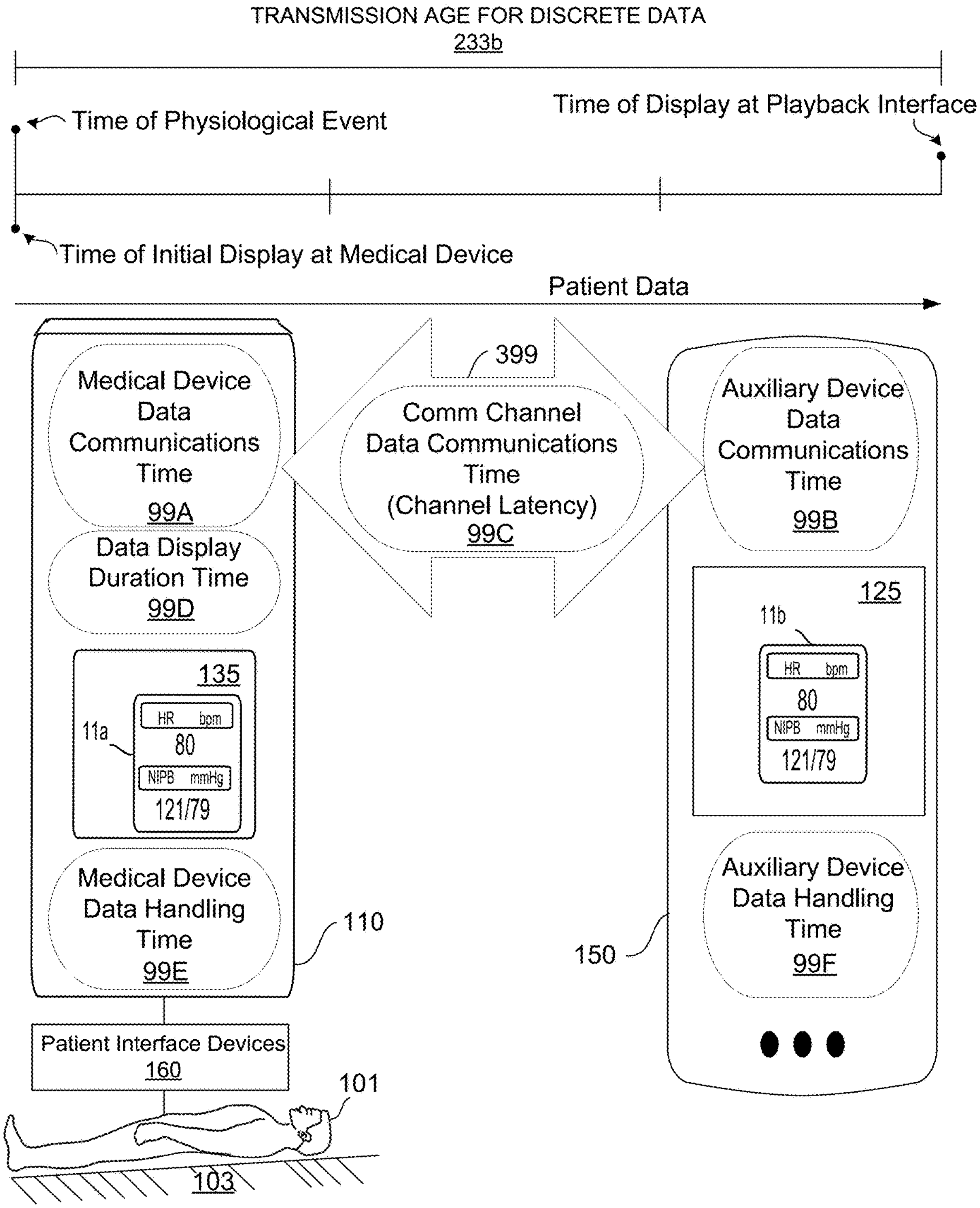
FIG. 1C is an exemplary schematic that conceptually illustrates transmission age for patient data represented as discrete values.

Referring to FIG. 1C, contributions to transmission age for discrete data are shown schematically. The medical device 110 receives patient data (e.g., patient data associated with the patient 101) via the patient interface devices 160. For example, the patient data may be discrete data 11*a* such as heart rate (HR), non-invasive blood pressure (NIBP), oxygen saturation (e.g., SpO2), end-tidal CO2, etc. The medical device 110 receives discrete data 11*a* at discrete intervals. For example, the user of the medical device 110 may request a HR, NIBP, or other discrete data reading, for example, via a soft key at the medical device 110. As another example, the medical device 110 may automatically collect the discrete data according to a schedule (e.g., every minute, every three minutes, every ten minutes, every 30 minutes, etc.). The medical device 110 receives and displays the discrete data 11*a* at discrete collection intervals.

In an implementation, in a patient monitoring mode, the medical device 110 may receive a heart rate reading every second, an invasive blood pressure reading every second, and/or an SpO2 reading every second. In an implementation, the medical device 110 may receive a non-invasive blood pressure (NIBP) reading in response to a user request and not at a pre-determined time interval. In an implementation, during administration of CPR, the medical device 110 may receive a compression rate and/or compression depth reading with every administered chest compression or every few administered chest compressions (e.g., provided as a moving average of depth based on a small group of compressions). The medical device 110 may display each reading for a display duration until the next reading occurs. Thus, while the initial time of display of the discrete data at the medical device 110 substantially corresponds to the time of the physiological event, the subsequent times of display during the display duration include a delay from the occurrence of the physiological event. Over the display duration, the medical device 110 may repeatedly transmit the heart rate reading. Therefore, for the discrete data 11*a*, the age of the playback discrete data 11*b* may include a contribution based on the data display duration time 99D at the medical device.

As shown in FIGS. 1B and 1C, a medical device data handling time 99E may be associated with the medical device 110. The medical device data handling time 99E includes time durations associated with handling the data signals received by the medical device 110 from the patient interface devices 160 in order to provide data representative of these data signals at the operational interface 135. For example, the medical device data handling time 99E may include contributions from one or more of, but not limited to, analog-to-digital conversion (e.g., conversion of sensor signals to digital data), data buffering (e.g., processor buffering, first-in-first-out buffering, memory buffering, etc.), data filtering, graphics processing, etc. The medical device data handling time 99E may not contribute to times associated with transmission of the patient data to the auxiliary device 150. For purposes of this disclosure, the medical device data handling time 99E may be considered as negligible. Based on this assumption, for the purposes of this disclosure, the physiological condition represented by the waveform data 10*a* may be considered to be instantaneously displayed at the medical device 110 with clinically acceptable and negligible delay. Therefore, in FIG. 1B, the "time of physiological event" and the "time of display at medical device" are shown as being simultaneous. Similarly, based on this assumption, for the purposes of this disclosure, the physiological condition represented by the discrete data 11*a* may be considered to be instantaneously displayed at the medical device 110 with clinically acceptable and negligible delay. Therefore, in FIG. 1C, the "time of physiological event" and the "time of initial display at medical device" are shown as being simultaneous.

As additionally shown in FIGS. 1B and 1C, an auxiliary device data handling time 99F may be associated with the auxiliary device 150. Internal data processing by the auxiliary device 150 includes a period of time, e.g., the auxiliary device data handling time 99F, between arrival of transmitted data at the reception buffer 222*b* (e.g., as shown in FIG. 14) and display of the transmitted data at the playback interface 125. In some situations, the auxiliary device data handling time 99F may be negligible or may contribute to the patient data age. As the transmission ages 233*a* and 233*b* include the time between the physiological event and the display at the playback interface 125, the auxiliary device data handling time 99F may contribute to the transmission age 233*a* and/or 233*b*. As one non-limiting example, the data display rate at the auxiliary device 150 may be lower than a data transmission rate for the medical device 110. As a result, the amount of data in the reception buffer 222*b* (e.g., as shown in FIG. 14) may increase in size over the course of a transmission. For example, the transmission may be a long duration transmission (e.g. in excess of 30 minutes). This backlog in the reception buffer 222*b* may provide a non-negligible contribution of the auxiliary device data handling time 99F to the transmission age 233*a* and/or 233*b* and may increase the transmission age 233*a* and/or 233*b* to such an extent that the patient data age exceeds the patient data age threshold. To remedy this increase, in an implementation, the auxiliary device 150 may provide instructions to purge the reception buffer 222*b*. Alternatively, the auxiliary device 150 may provide instructions that enable an increase in a playback speed of the patient data at the playback interface 125 to reduce the backlog in the reception buffer 222*b*. These steps may reduce the contribution of the auxiliary device data handling time 99F to the transmission age 233*a* and/or 233*b* and may thereby reduce the patient data age. The reduction in the patient data age may restore the patient data to a clinically actionable state.

Referring to FIGS. 1B and 1C, several factors may determine the transmission delays that contribute to the transmission ages 233*a* and/or 233*b*. For waveform data, these factors may include, but may not be limited to, a medical device data communications time 99A, an auxiliary device data communications time 99B, a communication channel data latency 99C (also referred to as a communication channel data communications time), and a user selected playback time. For discrete data, these factors may include, but may not be limited to, the medical device data communications time 99A, the auxiliary device data communications time 99B, the communication channel latency 99C, the data display duration time 99D, and the user selected playback time.

The medical device data communications time 99A and the auxiliary device data communications time 99B may contribute to latency in data communication from the medical device 110 to the auxiliary device 150. Data processing for communication (e.g., transmission and/or reception) by the communication interface 145 and/or the communication interface 245 may provide a source of latency. For example, transmission buffering (e.g., by the transmission buffer 122*a*) or reception buffering (e.g., by the reception buffer 222*b*) and/or backlogs in these buffers may contribute to the data communications times 99A and 99B. Backlogs in these buffers may occur due to differences between the transmission rate of the medical device 110 and one or more of a reception rate at the auxiliary device 150 or a display rate at the auxiliary device 150. The display rate may determine how fast the auxiliary device removes data from the reception buffer 222*b*. The communication channel latency 99C may indicate, for example, time delays associated with the communicative coupling provided by the communication channel 399.

In an implementation, the medical device data communications time 99A may include a data capture interval for waveform data. The medical device 110 may divide continuous data such as waveform data into time slices. Each time slice includes data collected over the data capture interval. The medical device 110 may transmit the continuous data such as the waveform data in packets corresponding to the time slice. For example, the medical device 110 may collect ECG waveform data for a data capture interval of 0.11 msec, 1 msec, 4 msec, 10 msec, 50 msec, 100 msec, 120 msec, 180 msec, 200 msec, 300 msec, or 500 msec, or another interval between 0.11-500 msec. At the end of each interval, the medical device 110 may package the time slice of ECG data with a header and/or other data and transmit the data to the auxiliary device 150. For example, if the data capture window is 100 msec, then the medical device 110 collects first ECG data for 100 msec, transmits the first ECG data, collects second ECG data for another 100 msec, and transmits the data, and so on. Therefore, the medical device data communications time 99A may be at least as long as the data capture interval for continuous data. In contrast, the medical device 110 may transmit the discrete data as it is received (e.g., the medical device may receive heart rate data every second and transmit the heart rate data every second) rather than collecting the discrete data over a pre-determined time period. In an implementation, the medical device 110 may transmit snapshots of data collected around an event. The medical device 110 may collect the data for a predetermined interval before and after the event and then transmit the entire amount of collected data. For example, the snapshot may include data collected for 2-10 seconds prior to the event and for 2-10 seconds after the event.

The auxiliary device 150 and/or the medical device 110 may implement various procedures to measure and/or estimate the medical device data communications time 99A and the auxiliary device data communications time 99B. For example, in an implementation, one or more of the devices 110 and 150 may measure or estimate the times 99A and 99B based on simulated data processing for a variety of machine states and/or configurations. The simulated data processing may include various data quantities and/or various processing speeds. In an implementation, one or more of the devices 110 and 150 may determine the times 99A and/or 99B based on a statistical measure (e.g., average, median, etc.) derived from a range of times associated with the simulated data processing. In an implementation, one or more of the devices 110 and 150 may store the measured or estimated value of the time 99A and/or 99B in a look-up table for hardware latency. As an example of a simulation, the medical device 110 may generate a calibration pulse or test pulse and estimate the hardware latency according to a protocol such as the IEEE 1588 Precision Time Protocol.

Additionally or alternatively, in an implementation, one or more of the devices 110 and 150 may determine (e.g., measure or estimate) a round-trip time (RTT) for data. The medical device 110 and/or the auxiliary device 150 may determine or estimate the transmission age 233*a* and/or 233*b* based on the RTT. The RTT may be a net data communications time based on a combination of 99A, 99B, and 99C. The net data communications time may include at least the hardware communication times and the communication channel latency. For example, a first one of the devices 110 and 150 may send a time stamped packet to a second one of the devices 110 and 150 via the communication channel 399 at a time of transmission. The second one of the devices 110 and 150 may respond with an ACK message. The first one of the devices 110 and 150 may receive the ACK at a time of ACK receipt. The magnitude of the RTT between the first device and the second device is the difference between the time of transmission and the time of ACK receipt. The time stamps associated with the data packets enable each device 110 and 150 to buffer data packets for transmission and/or display in order of time stamps. Therefore, even if data packets arrive at the auxiliary device 150 out of time order, the auxiliary device may re-order the data packets for display according to the time stamps.

In an implementation, one or more of the devices 110 and 150 may measure or estimate the RTT. In an implementation, the auxiliary device 150 may measure or estimate the RTT and/or the medical device 110 may measure or estimate the RTT and provide the determined RTT to the auxiliary device 150. In an implementation, the auxiliary device 150 may determine an average, a weighted average, and/or other combination of the RTT determined by the medical device 110 and the RTT determined by the auxiliary device 150 to determine the net handling time.

In an implementation, the RTT measurement or estimation may occur in conjunction with establishing the communication channel 399. Additionally or alternatively, one or more of the devices 110 and 150 may measure or estimate the RTT in conjunction with a request for patient data from the auxiliary device 150, in conjunction with sending the patient data from the medical device 110 to the auxiliary device 150, and/or in conjunction with receiving the patient data at the auxiliary device 150. In various implementations, the medical device 110 and/or the auxiliary device 150 may repeat the RTT determination at a predetermined interval and adjust the transmission age 233*a* and/or 233*b* based on changes in the RTT. In an implementation, the predetermined interval may provide for a repeat and/or update of the RTT determination in response to an establishment and/or re-establishment of the communication channel 399 and/or in response to a launch of the playback interface 125 by the auxiliary device 150 and/or in response to a request for one or more specific types of patient data from the medical device 110. The repeat of the RTT determination may happen with each occurrence of these events or at some pre-determined interval (e.g., every other event, every third event, etc.). The RTT determination may be user-configurable with regard to which event triggers this determination and/or how often this determination occurs. In an implementation, the devices 110 and/or 150 may not repeat the RTT determination during the transmission and playback.

In an implementation, an initial RTT determination (e.g., measurement or estimation) may occur at or near the time of the first transmission of patient data from the medical device 110 to the auxiliary device 150. One or more of the devices 110 and 150 may estimate the transmission age 233*a* and/or 233*b* based on this initial RTT determination. The value of the transmission age 233*a* and/or 233*b* based on this initial RTT determination may be an expected value. However, as an example, one or more of the times 99A, 99B, and/or 99C may change over the course of data transmission and prior to a repeat of the RTT determination. Thus an actual value for the transmission age 233*a* and/or 233*b* may change as a function of time such that the actual value may lag or lead the expected value.

The calculation or estimation of transmission ages 233*a* and 233*b* as described above is deterministic based on what is known, measured, calculated, and/or estimated with regard to the times 99A, 99B, and/or 99C. In between RTT determinations, the device 110 and/or 150 may dynamically detect changes and/or indications of changes in the times 99A, 99B, and/or 99C. In an implementation, the device 110 and/or 150 may update the transmission age 233*a* and/or 233*b* and the patient data age based on dynamically detected changes in the times 99A, 99B, and/or 99C. For example, once transmission and playback of the patient data begins, the devices 110 and/or 150 may monitor a state of data processing to detect changes in the times 99A, 99B, and/or 99C that may change the transmission age 233*a* and/or 233*b*. In an implementation, one or more of the devices 110 and/or 150 may predetermine a threshold buffer depth for a communication buffer (e.g., the reception buffer 222*b* shown in FIG. 14 for patient data collected at the medical device 110 and transmitted to the auxiliary device 150 for display). The threshold buffer depth may be associated with the initial transmission age determination. Over the course of patient data transmission, the device 150 may monitor the buffer depth of the reception buffer 222*b* shown in FIG. 14 relative to the threshold buffer depth. As one non-limiting example, if the buffer depth is below the threshold, this may indicate that the communication channel data latency 99C has decreased and the rate of receiving data at the communication buffer of the auxiliary device 150 has decreased. Thus, the patient data is taking longer to move from the medical device 110 to the auxiliary device 150. Therefore, the patient data may be older when it arrives at the auxiliary device 150 than indicated by the expected transmission age. Such a change may occur due to increases in the times 99A, 99B, and/or 99C since the initial transmission age determination. For example, increases in network traffic or increased CPU loads for the devices 110 and 150 may increase the times 99A, 99B, and/or 99C and increase the transmission age 233*a* and/or 233*b*.

In various situations, the end-to-end transmission time associated with the devices 110 and 150 and the communication channel 399 (e.g., the sum of 99A, 99B, and 99C) may exceed a time-out threshold for the communication channel 399. A communication protocol for the communication channel 399 may determine this time-out threshold according to a negotiation at the time of establishment of the communication channel 399. For example, if the medical device 110 transmits a data packet to the auxiliary device 150 and does not receive and ACK from the auxiliary device 150 within the time-out threshold, one or more of the medical device 110 and the auxiliary device 150 may shut down the communication channel 399. Depending on the specific clinical situation, this time-out threshold may increase the transmission age such that the patient data displayed at the playback interface 125 is no longer clinically relevant. In other words, the patient data displayed at the playback interface 125 is too old to be considered current data and to be considered reliable data on which to base clinical treatment decisions.

In addition to the times 99A, 99B, and 99C, the discrete data 11*a* may be subject to a data display duration time 99D. The initial time of display of the discrete data 11*a* at the medical device 110 is substantially equal to the time of occurrence of the physiological event represented by the discrete data 11*a*. Unlike the waveform data 10*a*, the discrete data 11*a* may persist at the medical device 110 throughout the discrete collection interval. The data display duration time 99D is a length of time that the discrete data 11*a* is displayed at the medical device 110. The discrete collection intervals determine the data display duration time 99D. At the time the measurement of the discrete data 11*a* occurs, the data display duration time 99D is zero and then increases as the discrete data 11*a* persists at the display and goes back to zero when re-measured at the end of the discrete collection interval. In an example, the handling times 99A, 99B, and 99C may be the same for discrete data 11*a* and waveform data 10*a*. However, due to the data display duration time 99D, the discrete data 11*a* displayed at the medical device may be further removed in time from the physiological event represented by this data than the waveform data 10*a*.

Figure 2A:
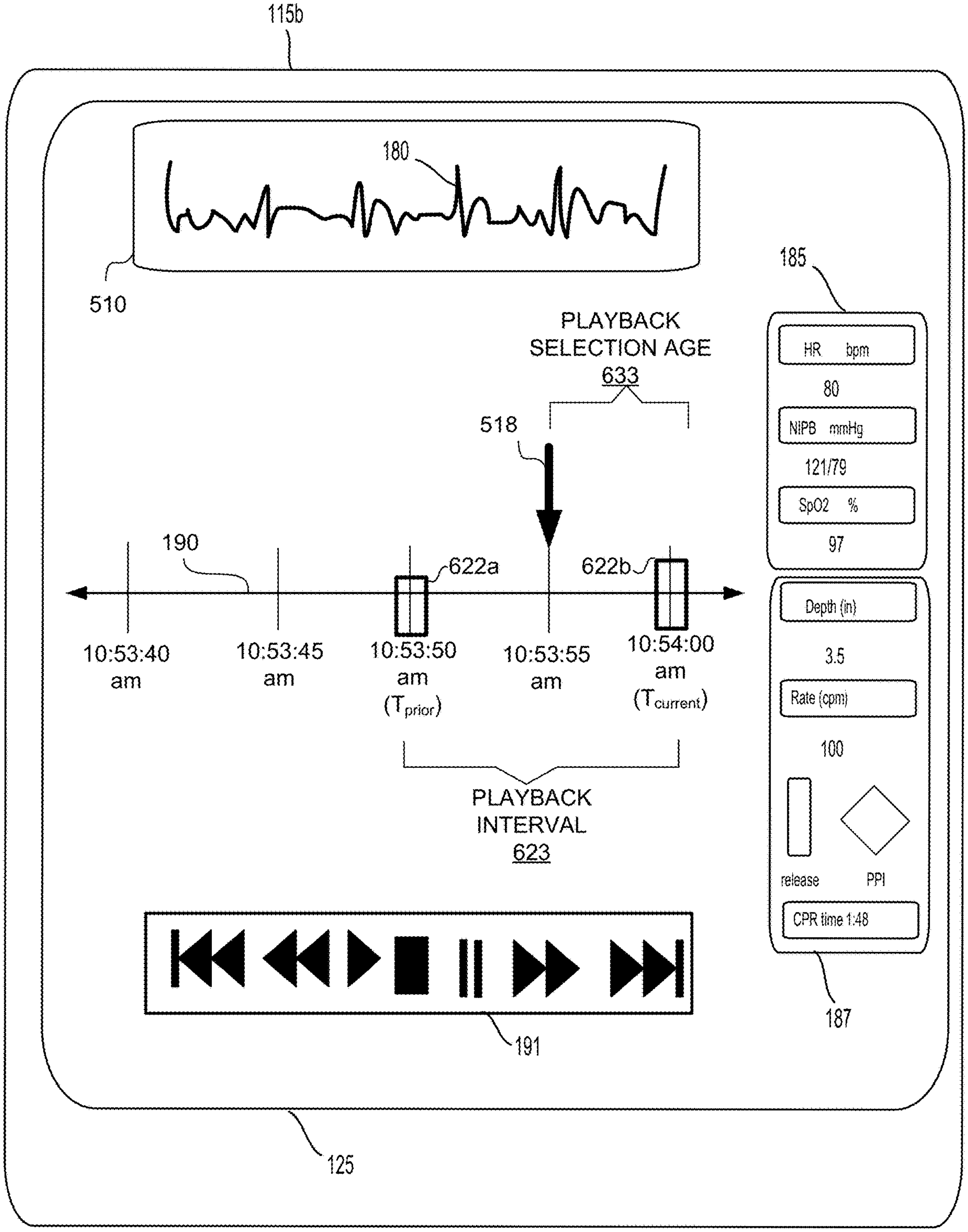
FIGS. 2A-2B show examples of an interactive timeline that enables selection of a playback time period.
Figure 2B:
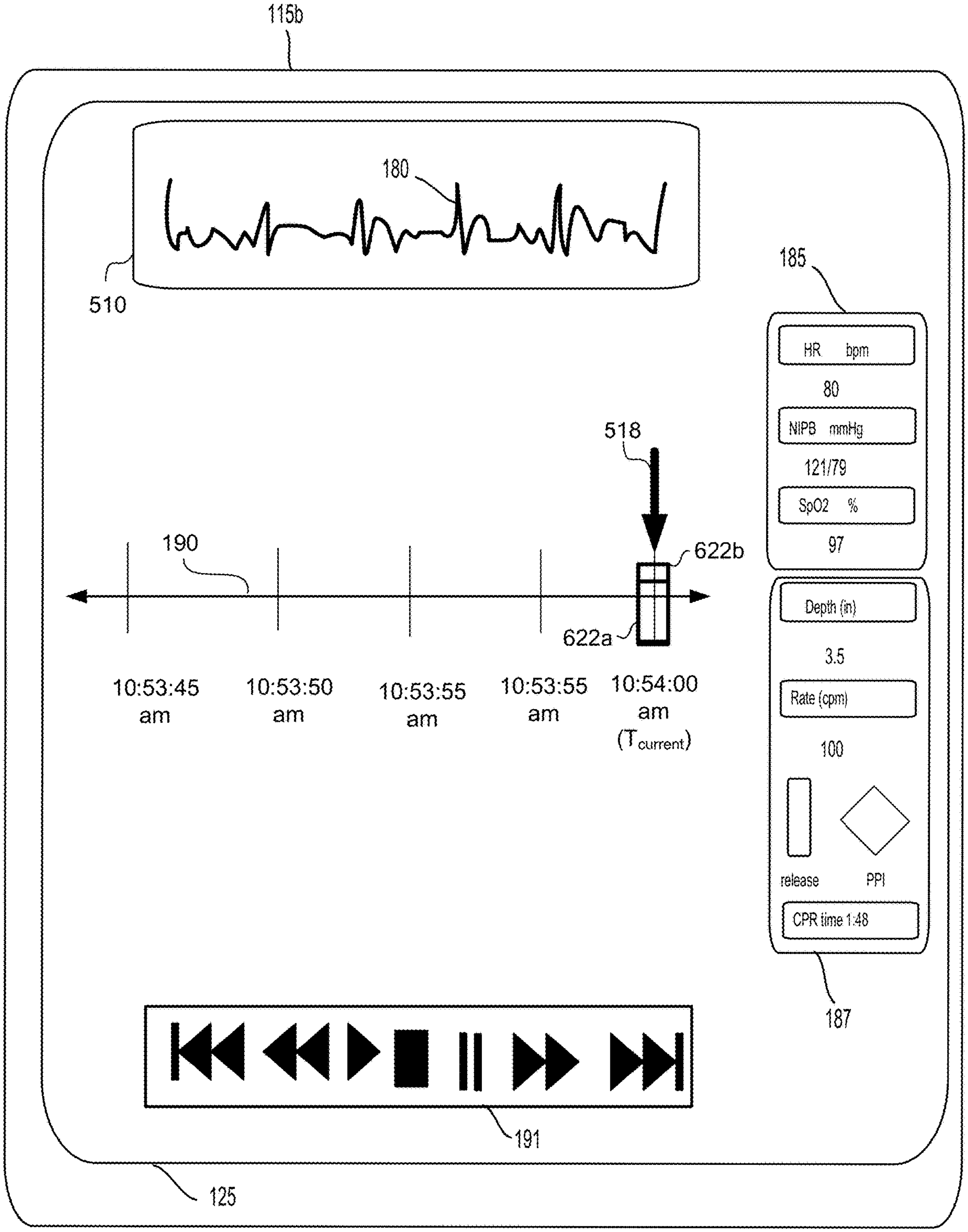

Referring to FIGS. 2A and 2B, examples of an interactive timeline that enables a user of the playback interface to select a playback time period is shown. The selected playback time period determines the user-selected age that contributes to the patient data age along with contributions from transmission latencies and the duration of data display.

The playback interface 125 may include an interactive timeline 190, a media navigation bar 191, and a data display window 510. The data display window 510 may be configured to display one or more visual representations of the patient data, for example, a physiological waveform 180. The playback interface 125 may further include discrete physiological measurement data 185 (e.g., data measured at discrete intervals as opposed to continuous measurements) and/or CPR performance parameters 187. Features of the playback interface 125 are discussed in further detail below with regard to FIGS. 7-13C. The user 102*b* may interact with the interactive timeline 190 to select a playback time period over which to review patient data.

Referring to FIG. 2A, in an implementation, the interactive timeline 190 may include two or more time interval selectors 622*a* and 622*b* (e.g., a first time interval selector and a second time interval selector). The time interval selectors 622*a* and 622*b* may define a playback interval 623 (e.g., a time interval selection). The playback interval 623 may be, for example, an interval of time over which the data display window 510 provides patient data associated with the time stamps during this interval of time. The playback interval 623 is the playback time period over which the user 102*b* may review patient data. The playback time period may determine a playback selection age 633 for the displayed data. As shown schematically in FIG. 2A, the playback selection age 633 may be the difference between the current clock time at the auxiliary device 150 and a time stamp associated with the data displayed in the window 510.

The overall age of the data displayed at the playback interface 125 is the sum of the transmission age 233*a* or 233*b* and the playback selection age 633. If the user of the playback interface 125 selects current data only (e.g., no historic data), then the playback selection age 633 is zero and the overall age of the data displayed at the playback interface 125 is just the transmission age 233*a* or 233*b*. If the user of the playback interface 125 selects historic data or historic data and current data, then the playback selection age 633 is non-zero and the age of the data displayed at the playback interface 125 changes over the playback interval 623.

In an implementation, the user may position the first time selector 622*a* to set a start time for the playback interval 623. The start time may be a time prior to a current clock time at the medical device 110 and/or auxiliary device 150 (e.g., $T_{prior}$). A clock associated with the auxiliary device 150 may determine the current clock time $T_{current}$ indicated at the playback interface 125. Each of the devices 110 and 150 may include a clock. At various intervals, these clocks may synchronize to a standard clock time. However, subsequent to the synchronization, these clocks will drift relative to each other and relative to the standard clock time. Therefore, the current clock time at the auxiliary device 150 may not be identical to the current clock time at the medical device 110.

The user may position the second time selector 622*b* to set an end time for the playback interval 623. The end time may be the current time at the playback interface 125 (e.g., for current and historic data) or may be a time prior to the current time (e.g., for all historic data). The playback interval is shown in FIG. 2A as including the current time as an example only. For all historic data, the playback interval 623 may exclude the current time and may only include times prior to the current time. In an implementation, the timeline 190 may include the first time selector 622*a* and not include the second time selector 622*b*. In such an implementation, the playback interval 623 may start at the first time selector 622*a* and automatically end at the current time.

Referring to FIG. 2B, the user may position the two or more time interval selectors 622*a* and 622*b* at the current time to select current time data and exclude historic data. In response to the selection of the current time with the time interval selectors 622*a* and 622*b*, the playback interface 125 may provide current patient data in a data display window 510. The age of the current patient data in the data display window may include the transmission age 233*a* or 233*b* as discussed above.

In an implementation, the user may sweep either the first time selector 622*a* or the second data time selector 622*b* off the timeline 190 to the right or to the left of the timeline 190. The user may position the remaining time selector at the current time to select current time data and exclude historic data.

For purposes of clinical decisions, a determination of whether or not the age of the patient data corresponds to current or non-current data may depend on the particular clinical decision(s) and/or procedure(s) at hand. For example, in a first scenario, the medical device 110 may monitor the patient 101 in response to a complaint of nausea. The patient interface devices 160 may provide patient data that indicates stable vital signs and a regular heart rhythm. In this scenario, the medical device 110 may monitor the patient over a period of hours or days within which the patient may only require a slow-paced drug administration intervention, such as an intravenous drip. In a second scenario, the medical device 110 may monitor the patient 101 in response to a suspected cardiac arrest. The patient interface devices 160 may provide patient data that indicates unstable vital signs and an arrhythmia. In this scenario, the medical device 110 may monitor the patient over a period of minutes within which the patient may require a fast-paced medical intervention such as defibrillation. Thus, the amount of tolerable delay in the data provided at the playback interface 125 may be considerably less in the second scenario as compared to the first scenario.

In general, the playback data (e.g., the patient data displayed at the playback interface 125) may be considered current data if this data is displayed close enough to the time of the physiological event and to the time of display at the medical device 110 to enable the caregivers 102*a* and/or 102*b* to medically respond to monitored physiological events in a clinically appropriate amount of time. In contrast, the playback data may be considered past data if this data is displayed too long after the time of the physiological event to enable the caregivers 102*a* and/or 102*b* to respond medically to monitored physiological events in a clinically appropriate amount of time. A designation of current or past for the playback data is deterministic based on ongoing medical conditions including, for example, a pace of progression and/or clinical developments in the type of monitored physiological events, a type of ongoing medical treatment in response to the monitored physiological events, and a physical proximity of the medical device 110 and the auxiliary device 150. These conditions may determine an acceptable patient data age relative to the same data displayed on the operational interface 135.

The type of monitored physiological events and/or the type of ongoing medical treatment may determine a pace of progression and/or clinical developments that, in turn, may determine an acceptable delay in the display of the playback data with regard to designating this data as current data or past data. The designation of current or past may depend on an age of data that defines a delay between a physiologic event and the display at the playback interface 125 of the data characterizing and/or generated by the physiologic event. Various factors including, for example, the ongoing medical treatment, the clinical condition of the patient, and/or an operational state of the medical device may determine the clinical relevance of the age of the data. In addition to the ongoing clinical situations, the physical proximity of the medical device 110 and the auxiliary device 150 may determine an acceptable patient data age.

Figure 3A:
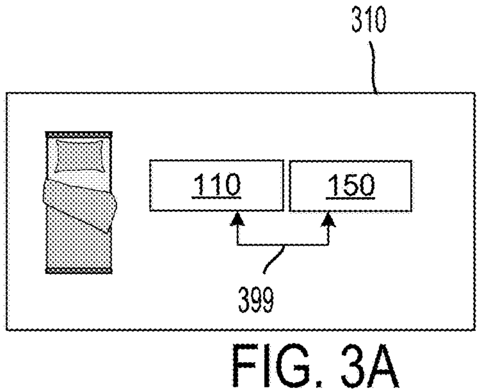
FIGS. 3A-3C show examples of proximate device configurations.
Figure 3B:
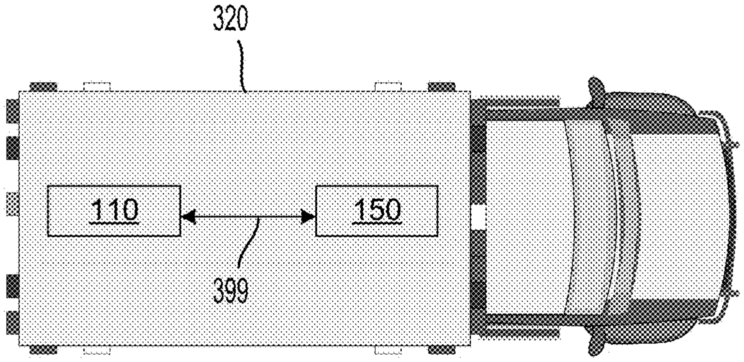
Figure 3C:
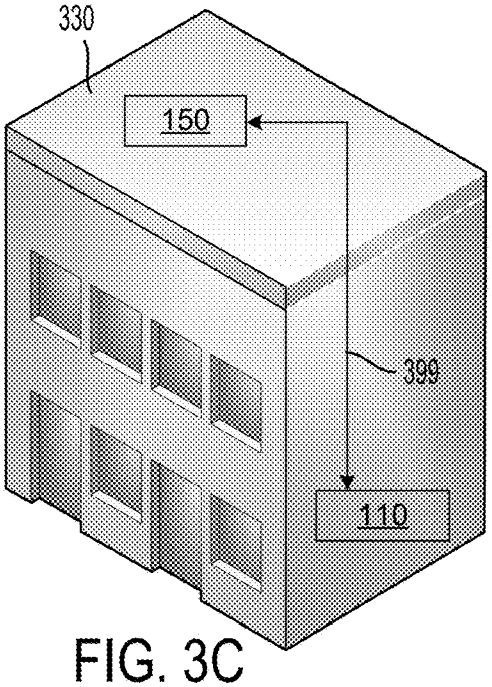

Referring to FIG. 3A-3C, examples of proximate device configurations are shown. The proximate devices may both be associated with a same local environment (e.g., as opposed to remote environments). As an example, the medical device 110 and the auxiliary device 150 may be considered proximate (i.e., not remote) if the caregivers 102*a* and/or 102*b* may reasonably expect to view the same data without a discernable delay. In these situations, caregivers may expect to be viewing the same data at the same time at both devices 110 and 150. Therefore, any discernable delay may cause confusion that may adversely impact patient care. For example, the two devices 110 and 150 may be located in a same patient area 310 or ambulance 320. The patient area 310 may be a patient treatment area such as a home, an office, a room in a home, a hospital room, a field or other outdoor area, a stretcher in transport (e.g., a stretcher being carried on a stairway or through an indoor or outdoor area) and/or an area in an airport, gymnasium, shopping center, a medical facility, etc. The patient area 310 is shown with a bed as an example only and may or may not include a bed, a stretcher, a gurney, and/or another patient support structure. As another example, the medical device 110 and the auxiliary device 150 may be available in different locations in a same building 330. For instance, the medical device 110 may be available in a hospital room of a patient and the auxiliary device 150 may be available at a nursing station monitoring the same patient.

The medical device 110 and the auxiliary device 150 may be considered remote (i.e., not proximate) if the caregivers 102*a* and/or 102*b* may reasonably expect to view the same data with a possible discernable delay. In these situations, caregivers expect to view the same data at approximately the same time at each interface 125 and 135 but may also expect that the data viewing time might include a discernable delay. Therefore, provided that the playback interface 125 provides an indication of the delay, this delay may not cause confusion that may adversely impact patient care.

Figure 3D:
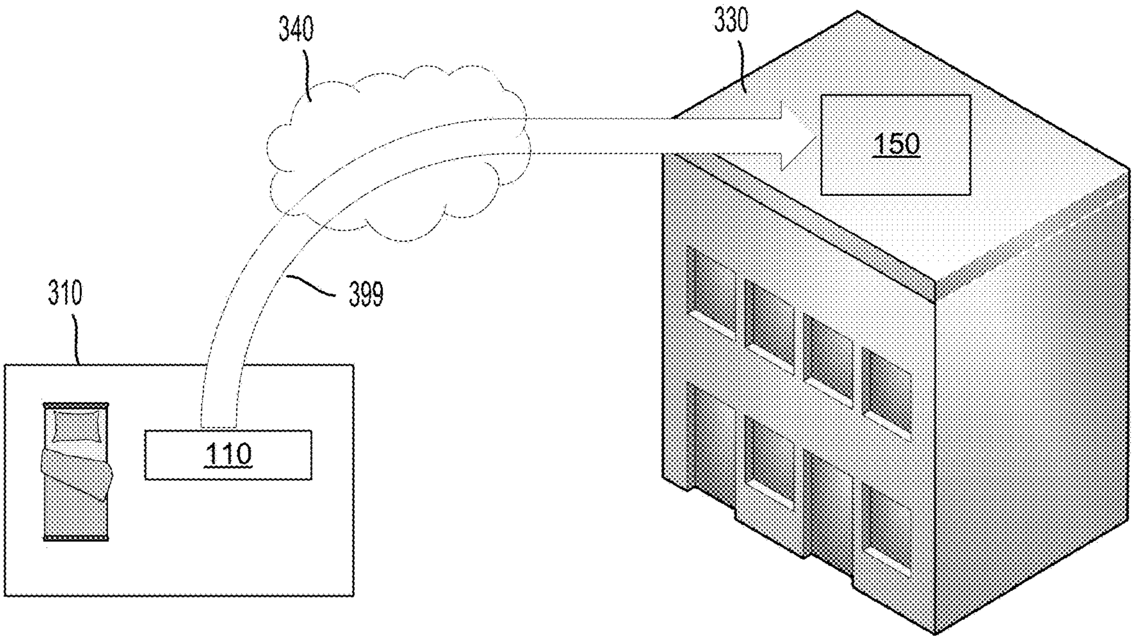
FIGS. 3D-3E shows examples of remote device configurations.
Figure 3E:
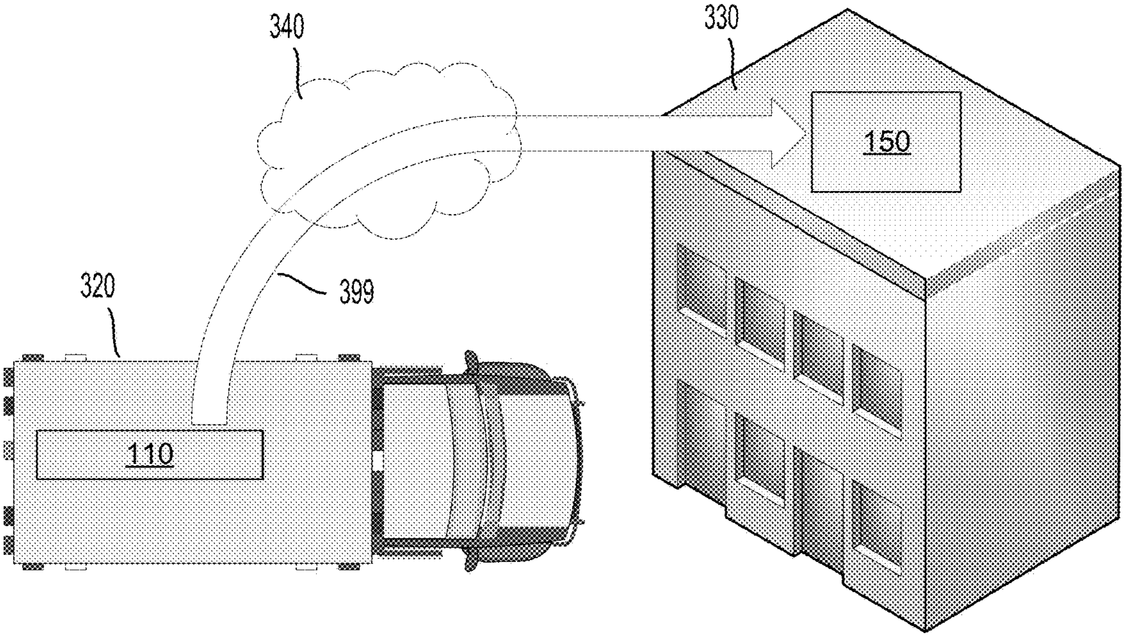

Referring to FIGS. 3D and 3E, examples of remote device configurations are shown. For example, as shown in FIG. 3D, the medical device 110 (e.g., with the operational interface 135) may be available in a patient area 310 and the auxiliary device 150 (e.g., with the playback interface 125) may be available at a hospital or other medical facility 330 providing tele-medical care for the same patient. The patient area 310 may be a patient treatment area such as a home, an office, a room in a home, a hospital room, a field or other outdoor area, and/or an area in an airport, gymnasium, shopping center, a medical facility, etc. The patient area 310 is shown with a bed as an example only and may or may not include a bed, a stretcher, a gurney, and/or another patient support structure. As another example, as shown in FIG. 3E, the medical device 110 may be available in the ambulance 320 or other vehicle transporting the patient and the auxiliary device 150 may be available at a dispatch center, a hospital, or other facility 330 preparing to treat and/or participating in treatment of the same patient. In an implementation, the examples of FIGS. 3D and/or 3E may include a telemedicine application. The auxiliary device 150 may be a computing device and/or a medical device configured for telemetry (e.g., a telemedicine auxiliary device). The medical device 110 located in the patient area 310 may collect for the patient and transmit this data via a wired connection, a wireless connection, or a combination thereof to the auxiliary device 150 at a location remote from the patient area 310. In an implementation, the medical device 110 may provide the data to a local computing device and the local computing device may transmit the data to the remote auxiliary device. The auxiliary device 150 may receive this transmitted data telemetrically and may store, process, analyze, and/or display this data in a manner such that the caregiver located with the auxiliary device 150 is confident that the presented data is up to date. Further, the auxiliary device 150 may enable treatment and/or monitoring of the patient in the patient area 310 via telemedicine. For example, medical personnel located with the auxiliary device 150 and/or with access to the auxiliary device 150 (e.g., via a short range or long range network) may view the data at the remote auxiliary device 150 and may provide user input to the auxiliary device 150 in response to this data. The auxiliary device 150 may capture the user input and transmit this user input back to the medical device 110 and/or to the local computing device associated with the auxiliary device 150. The user input may include instructions, feedback, settings, and/or prompts based on the data provided at the telemedicine auxiliary device and for the medical device 110 and/or the caregivers.

In order to determine the location of the medical device 110 relative to the auxiliary device 150, in an implementation, one or more of the caregivers 102*a* and 102*b* may provide input to the medical device 110 and/or the auxiliary device 150 indicative of the device proximity. Alternatively or additionally, one or more of the devices 110 and 150 may determine the relative location of the other of the device 110 or 150 based on characteristics of the communication channel 399. For the proximate device configurations of FIGS. 3A-3C, the communication channel 399 may be a short-range communicative coupling such as, for example, a tap-to-connect or other near field communication link, a Bluetooth® connection, a Bluetooth® Low Energy (BLE) connection, or a WiFi® connection to a local area network. The short-range communicative coupling may include connections to one or more in-premise servers. For the remote device configurations of FIGS. 3D and 3E, the communication channel 399 may include long-range communicative couplings via a network 340 such as a cellular network and/or a computer network. The long-range communicative couplings may include WiFi connections and/or connections to one or more servers located remotely and/or in-premise and may include cloud-based SaaS services and/or enterprise solutions.

In some implementations, the physical range associated with the type of communication channel or communication channel protocol may determine the proximity of the two devices 110 and 150. For example, the devices 110 and/or 150 may determine their proximity to one another based on BLE, access point information, base station information, and/or indoor location information.

As another example, an NFC protocol includes a set of communication protocols that enable two electronic devices (e.g., the medical device 110 and the auxiliary device 150) to establish communication by bringing them within approximately 4 cm (2 in) of each other. NFC is a set of short-range wireless technologies, typically requiring a separation of 10 cm or less. NFC facilitates the integration of contactless technology into active device platforms, such as mobile tablets or phones. NFC is a short-range RFID technology operating at the 13.56 MHz radio frequency (RF) band and is described in the ISO 18092/ECMA 340 and in ISO 21481/ECMA 352 standards. NFC is specified to be compatible with existing contactless systems adhering to ISO 14443, ISO 15693 and FeliCa. The standards specify both 'passive' and 'active' operation. Passive operation corresponds to the operation of conventional contactless systems. The NFC device can therefore, either act like a contactless token, interacting with a reader, or act like a reader, powering and interacting with a contactless token. Two NFC devices can also interact with each other in an active or peer-to-peer (P2P) mode when brought in close proximity. In this active mode, devices take turns to transmit an RF field, e.g. the auxiliary device 150 may turn on its RF field and transmit data to the medical device 110, followed by the auxiliary device 150 turning off its field and the medical device 110 turning on its field and transmitting data to the auxiliary device 110.

The examples of proximate and remote devices provided herein are examples only and not limiting of the disclosure. Similarly, the communicative couplings illustrated for these various examples of proximate and remote devices are examples only and not limiting of the disclosure. Other types and/or combinations of communicative couplings are within the scope of the disclosure.

Tables 1 and 2 below show examples of patient data age thresholds for different distances between the medical device 110 and the auxiliary device 150, for a variety of machine states for the medical device, and for a variety of patient data types. The machine state of the medical device may indicate one or more of a machine configuration or operational mode. As non-limiting examples, the machine configuration may correspond to a provided dashboard such as a traumatic brain injury (TBI) dashboard or a cardiopulmonary resuscitation (CPR) dashboard. As non-limiting examples, the operational mode may be one of patient monitoring, patient monitoring in the presence of a specific medical condition (e.g., myocardial infarction, respiratory distress, etc.), patient therapy (e.g., defibrillation, pacing, ventilation, etc.), or heart rhythm analysis. As non-limiting examples, the patient data types may be one of accelerometer data, ECG data, gas flow data, gas pressure data, CPR data, capnography data, pulse oximetry data, blood pressure data. Further, the patient data type may be indicative of a particular physiological condition. For example, the ECG data may be indicative of ventricular fibrillation (VF), ventricular tachycardia (VT), or atrial fibrillation (AF). Although the accelerometer data is included as a patient data type in Tables 1 and 2, the accelerometer data may be caregiver performance data during CPR delivered to the patient by caregiver.

Each table includes a set of patient data age thresholds and each patient data age threshold corresponds to a particular patient data context. As shown in Tables 1 and 2 below, the particular patient data context may correspond to a particular combination of the machine state and the patient data type. Each patient data age threshold may be a maximum acceptable patient data age or a range of acceptable patient data ages. The acceptable patient data age may be a patient data age that renders the patient data clinically actionable given the particular patient data context.

Table 1 refers to proximate devices (e.g., the device configurations shown, for example, in FIGS. 3A-3C). Table 2 refers to remote devices (e.g., the device configurations shown, for example, in FIGS. 3D and 3E). The patient data age thresholds may be predetermined and may be included, for example, in at least one look-up table for the playback interface 125. The memory 221 (as shown in FIG. 14) of the auxiliary device 150 may include the at least one look-up table. In an implementation, the playback interface 125 may access at least a first look-up table that includes a first set of patient data age thresholds for the proximate relative location and at least a second look-up table that includes the second set of patient data age thresholds for the remote relative location. In the absence of location information indicating whether the medical device 110 and the auxiliary device 150 are proximate or remote, the playback interface 125 may be configured to select one of the threshold for proximate devices or for remote devices. The playback interface 125 may determine whether or not current data and/or playback data are clinically actionable based on a comparison of the patient data age for the current data or the playback data with the patient data age thresholds.

In addition or as an alternative to the distance between the medical device 110 and the auxiliary device 150, the patient data age thresholds may depend on a patient data context. The patient data context may correspond to a machine state for the medical device, a type of patient data, or a combination thereof.

The machine state may correspond to an operational mode of the medical device 110 that may be recognizable and/or detectable by the medical device 110. For example, the machine state of the medical device may correspond to a dashboard currently displayed at the medical device 110 (e.g., a traumatic brain injury (TBI) dashboard, a cardiopulmonary resuscitation (CPR) dashboard, a ventilation dashboard, etc.), a routine underway at the medical device 110 (e.g., heart rhythm analysis, patient monitoring, etc.), and/or a treatment provided by the medical device 110 (e.g., defibrillation, pacing, ventilation, etc.). The machine state may also depend on the types of patient interface devices 160 connected to and/or providing data to the medical device 110.

The patient data type may include, for example, but not limited to, electrocardiogram (ECG data), gas flow data, gas pressure data, CPR data (e.g., accelerometer data), capnography data, pulse oximetry data, blood pressure data (e.g., non-invasive blood pressure (NIBP) and/or invasive blood pressure (IBP)). The types of data may further include any data accessible via the patient interface devices 160 and/or 260.

The patient data context may indicate a clinical situation, a patient disease state, and/or the clinical decisions being made with regard to, for example, patient treatment and/or diagnosis. The clinical situation and/or the patient disease state may be current, recurrent, recent, or otherwise relevant to the clinical decisions based on the patient data. Thus the patient data context may determine the patient data age that renders the patient data displayed at the playback interface 125 clinically actionable. For example, the threshold for ECG data may be different for monitoring a patient as compared to analyzing a heart rhythm in preparation for defibrillation therapy. As another example, the threshold for the ECG data may be different for monitoring the patient in response to a myocardial infarction as compared to monitoring the patient in response to respiratory distress.

In an implementation, the patient data context may further depend on patient medical record information. This information may include patient medical records accessed by the medical device 110 and/or the auxiliary device 150, information provided to the medical device 110 and/or the auxiliary device 150, and/or the physiological measurements provided by the patient interface devices 160 and/or 260. The patient medical records may include electronic medical records accessible by and/or provided to the medical device 110 and/or the auxiliary device 150. The patient medical records may include for example, an electronic patient care record (ePCR) and/or an electronic medical record (eMR) and/or other electronic records generated by emergency medical services, a hospital, a physician or other caregiver, etc. In an implementation, the medical device 110 and/or the auxiliary device 150 may provide soft keys, data entry fields on a user interface, touchscreen icons, etc. configured to capture the information provided by the caregiver.

In an implementation, the auxiliary device 150 may programmatically determine the patient data context based on various combinations of information. For example, the existence of a 12-lead ECG combined with a TBI dashboard may indicate a different patient data context than the 12-lead ECG combined with a ventilation dashboard. In an implementation, the auxiliary device 150 may use various clinical criteria to deduce the patient data context. For example, the presence of cardiac symptoms for a duration of 15 min-12 hours along with a particular ST elevation in a 12-lead ECG and combined with one or more of cardiac monitoring and an indication of nitroglycerin administration may indicate a ST elevation myocardial infarction (STEMI) in a patient. As another example, the presence of two or more of an elevated temperature, respiratory rate, and heart rate along with a particular end-tidal CO2 and combined with one or more of cardiac monitoring, capnography monitoring, and 12-lead ECG may indicate sepsis in a patient. As a further example, detection of a 12-lead ECG along with vital sign monitoring, pulse oximetry, and an administration of Albuterol may indicate respiratory distress in a patient.

In an implementation, the patient data age thresholds in Table 1 and Table 2 may be available for user configuration. In an implementation, the playback interface 125 may restrict the user configurable thresholds to a particular range of values, a maximum value, or a minimum value. Additionally or alternatively, the playback interface 125 may allow the user to select any threshold without restriction and/or may enable user configuration based on a particular caregiver role (e.g., medical director, physician, nurse, emergency medical technician, etc.). In various implementations, one or more of the patient data age thresholds may be available for user configuration. For example, the user may configure a particular threshold to a narrower range within the patient data age threshold range shown in Table 1 or Table 2, or the user may configure the threshold to a wider range than that shown in Table 1 or Table 2. Hence, the acceptable patient data age thresholds indicated may differ depending on the preference of the administration/supervising organization. The accelerometer data may include an accelerometer waveform and/or data derived from an accelerometer waveform such as, for example, but not limited to, a compression rate, a compression depth, a release velocity, etc. The patient data age threshold for heart rhythm analysis represents a special case for which the patient data age threshold depends on the machine state combined with features of the patient data. For example, within the machine state of heart rhythm analysis, the patient data age threshold depends on whether the ECG includes features indicative of ventricular fibrillation (VF), ventricular tachycardia (VT), or atrial fibrillation (AF).

TABLE 1

| Proximate Devices | | |
|---|---|---|
| Machine State of Medical Device | Patient Data Type | Exemplary Patient Data Age Threshold |
| Patient Monitoring | ECG | 1-2 sec |
| | Pulse oximetry | 1-2 sec |
| | Capnography | 5-10 sec |
| | NIBP | 10-30 sec |
| Patient Monitoring-Myocardial Infarction | ECG | 10-15 sec |
| | Pulse oximetry | 10-15 sec |
| | Capnography | 5-10 sec |
| | NIBP | 10-30 sec |
| Patient Monitoring-Respiratory Distress | ECG | 10-15 sec |
| | Pulse oximetry | 2-10 sec |
| | Capnography | 5-10 sec |
| | NIBP | 10-30 sec |
| Patient Therapy-Defibrillation | ECG | 10-15 sec |
| | Pulse oximetry | 1-5 sec |
| | Capnography | 5-10 sec |
| | NIBP | 10-30 sec |
| Patient Therapy-Pacing | ECG | 10-15 sec |
| | Pulse oximetry | 1-5 sec |
| | Capnography | 5-10 sec |
| | NIBP | 10-30 sec |

TABLE 1-continued

| Proximate Devices | | |
|---|---|---|
| Machine State of Medical Device | Patient Data Type | Exemplary Patient Data Age Threshold |
| Patient Therapy-Ventilation | ECG | 10-15 sec |
| | Pulse oximetry | 10-15 sec |
| | Capnography | 2-10 sec |
| | NIBP | 10-30 sec |
| TBI Dashboard | Pulse oximetry | 10-15 sec |
| | Capnography | 2-10 sec |
| | NIBP | 10-30 sec |
| | Gas flow (airway) | 2-5 sec |
| | Gas pressure (airway) | 2-5 sec |
| CPR Dashboard | Accelerometer data | 2-5 sec |
| | NIBP | 10-30 sec |
| | ECG | 10-15 sec |
| | Pulse oximetry | 10-15 sec |
| | Capnography | 2-10 sec |
| Heart Rhythm Analysis | ECG-VF | 2-5 sec |
| | ECG-VT | 5-10 sec |
| | ECG - AF | 10-25 sec |

TABLE 2

| Remote Devices | | |
|---|---|---|
| Machine State of Medical Device | Patient Data Type | Exemplary Patient Data Age Threshold |
| Patient Monitoring | ECG | 10-15 sec |
| | Pulse oximetry | 10-15 sec |
| | Capnography | 10-15 sec |
| | NIBP | 30-60 sec |
| Patient Monitoring-Myocardial Infarction | ECG | 10 sec-1 min |
| | Pulse oximetry | 30 sec-1 min |
| | Capnography | 30 sec-1 min |
| | NIBP | 30-60 sec |
| Patient Monitoring-Respiratory Distress | ECG | 10 sec-1 min |
| | Pulse oximetry | 30 sec-1 min |
| | Capnography | 30 sec-1 min |
| | NIBP | 30-60 sec |
| Patient Therapy-Defibrillation | ECG | 10 sec-1 min |
| | Pulse oximetry | 30 sec-1 min |
| | Capnography | 30 sec-1 min |
| | NIBP | 30-60 sec |
| Patient Therapy-Pacing | ECG | 10 sec-1 min |
| | Pulse oximetry | 30 sec-1 min |
| | Capnography | 30 sec-1 min |
| | NIBP | 30-60 sec |
| Patient Therapy-Ventilation | ECG | 10 sec-1 min |
| | Pulse oximetry | 30 sec-1 min |
| | Capnography | 30 sec-1 min |
| | NIBP | 30-60 sec |
| TBI Dashboard | Pulse oximetry | 30 sec-1 min |
| | Capnography | 30 sec-1 min |
| | NIBP | 30-60 sec |
| | Gas flow (airway) | 10-20 sec |
| | Gas pressure (airway) | 10-20 sec |
| CPR Dashboard | Accelerometer data | 10-20 sec |
| | NIBP | 30-60 sec |
| | ECG | 10 sec-1 min |
| | Pulse oximetry | 30 sec-1 min |
| | Capnography | 30 sec-1 min |
| Heart Rhythm Analysis | ECG-VF | 5 sec-10 sec |
| | ECG-VT | 10 sec-20 sec |
| | ECG - AF | 10 sec-1 min |

Figure 4A:
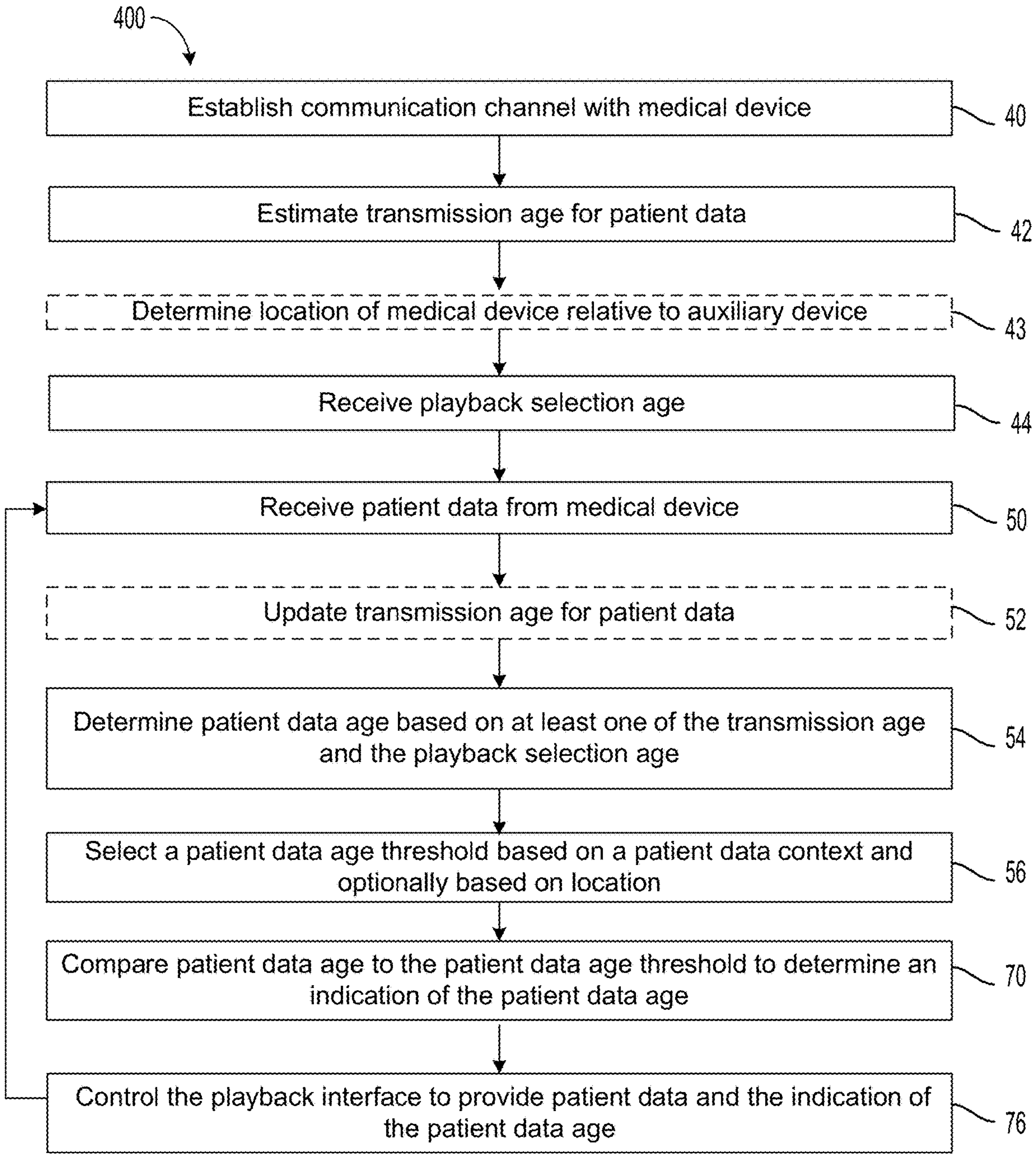
FIG. 4A shows an example process flow of a method for providing patient data and an indication of patient data age at a playback interface.

Referring to FIG. 4A, a method 400 of providing patient data and the indication of patient data age at a playback interface is shown. The method 400 is, however, an example only and not limiting. The method 400 can be altered, e.g., by having stages added, removed, rearranged, combined, and/or performed concurrently. Functions described as being performed by the auxiliary device 150 and/or the playback interface 125 may be performed by the processor 220 and/or another component of the auxiliary device 150 as discussed with regard to FIG. 14. Functions described as being performed by the medical device 110 and/or the operational interface 135 may be performed by the processor 120 and/or another component of the medical device 110 as discussed with regard to FIG. 14. In an implementation, the medical device 110 may be the modular medical device 410 and functions performed by the medical device 410 may be performed by the processor 420*a*, 420*b*, and/or another component of the medical device 410 as discussed with regard to FIG. 15.

At the stage 40, the method 400 may include establishing the communication channel. For example, the auxiliary device 150 and the medical device 110 may establish the communication channel 399. The auxiliary device 150 and/or the medical device 110 may initiate the establishment of the communication channel 399.

At the stage 42, the method 400 may include estimating a transmission age for patient data. For example, the transmission age may be the transmission age 233*a* for waveform data or the transmission age 233*b* for discrete data. As a part of the establishment of the communication channel 399, the processor of the auxiliary device 150 and/or the medical device 110 may determine (e.g., measure, calculate, and/or estimate) the RTT and/or the simulated data communications time as discussed above in reference to FIGS. 1B and 1C. The auxiliary device 150 may determine the transmission age 233*a* for the waveform data based on the RTT. The RTT may include the data communications times, or latencies, 99A, 99B, and 99C. Additionally, the medical device 110 may provide an estimate of the data display duration time 99D to the auxiliary device 150 to determine the transmission age 233*b* for the discrete data. The medical device 110 may determine the data display duration time 99D based on a difference between a current time and most recent update of the discrete data (e.g., either according to a pre-determined automated schedule and/or in response to a user request).

At the stage 43, the method 400 may optionally include determining a location of the medical device 110 relative to the auxiliary device 150. For example, as discussed above in reference to FIGS. 3A-3E, the medical device 110 and/or the auxiliary device 150 may determine if a relative location of the medical device and the auxiliary device is a proximate relative location (e.g., as exemplified in FIGS. 3A-3C) or a remote relative location (e.g., as exemplified in FIGS. 3D-3E).

At the stage 44, the method 400 may include receiving a playback selection age 633. For example, the auxiliary device 150 may capture a playback selection age 633 via the playback interface 125 (e.g., via the interactive timeline 190). If the user of the playback interface 125 at the auxiliary device 150 requests current data, then the playback selection age 633 is zero. If the user requests historic data, then the playback selection age 633 is non-zero. The playback selection age 633 refers to the time stamp or range of time stamps selected by the user 102*b* of the playback interface 125 for patient data displayed at the playback interface 125.

At the stage 50, the method 400 may include receiving patient data from the medical device. For example, the medical device 110 may transmit the patient data and the auxiliary device 150 may receive the transmitted patient data. The auxiliary device 150 may process the transmitted patient data in order to display the patient data at the playback interface 125.

At the stage 52, the method 400 may optionally include updating the transmission age for the patient data. For example, as discussed above with regard to FIGS. 1B and 1C, the auxiliary device 150 may monitor the buffer depth of the reception buffer 222*b* to detect changes in the transmission age of the patient data. The auxiliary device 150 may update a previously determined transmission age 233*a* and/or 233*b*. In an implementation, the auxiliary device updates the transmission age 233*a* and/or 233*b* in response to a receipt of patient data and may perform the update at a pre-determined interval. This interval may be a user configurable interval. For example, the auxiliary device 150 may provide this update in coordination with a screen refresh of the playback interface 125. Alternatively, the auxiliary device 150 may provide this update at some fraction of the screen refresh cycles (e.g., every second cycle, every third cycle, etc.), at random points in the course of playback, or at pre-determined time intervals (e.g., for example, but not limited to every 0.02 seconds, 0.04 seconds, 0.1 seconds, 0.5 seconds, 1 second, 2 seconds, 5 seconds, 30 seconds, 60 seconds, 120 seconds, etc.).

At the stage 54, the method 400 may include determining a patient data age based on at least one of a transmission age and a playback selection age. For example, the auxiliary device 150 may determine the patient data age. The patient data age may be the transmission age 233*a* or 233*b*, the playback selection age 633, or a combination thereof.

At the stage 56, the method 400 may include selecting a patient data age threshold based on a patient data context and optionally based on location. As discussed in more detail below with regard to FIG. 4B, the medical device 110 and/or the auxiliary device 150 may determine the patient data context based on one or more of a type of patient data and a machine state of the medical device 110. The patient data may indicate the patient data context with information included for example as a header and/or as another form of associated, attached, and/or embedded information. For example, the information may indicate the type of patient data and/or the machine state of the medical device 110. The patient data context may indicate or suggest a clinical purpose for the patient data. In various implementations, the auxiliary device 150 may determine the patient data context based on one or more of user input to the playback interface 125 and a machine state of the medical device 110. The user input to the playback interface 125 may be, for example but not limited to, a selection of an event indicator 620 and/or input to the medical condition selection control 586, as discussed below with regard to FIG. 7 and FIG. 8. Such input may indicate a pending clinical decision and/or medical treatment relevant to the patient data viewed at the playback interface 125.

Optionally, at the stage 56, the method 400 may include selecting the patient data age threshold based on the location determined at the stage 43. If the method 400 includes the stage 43, then the auxiliary device 150 may select the patient data age threshold based on a relative location of the medical device 110 and the auxiliary device 150. For example, the memory of the auxiliary device 150 (e.g., the memory 221 shown in FIG. 14) may include one or more look-up tables for the patient data age threshold. The one or more look-up tables may include Table 1 (e.g., a first look-up table) for a proximate relative location and Table 2 (e.g., a second look-up table) for a remote relative location. The auxiliary device 150 may select one of the patient data age thresholds in Table 1 or Table 2 based on the relative location. In the absence of the location information, the method 400 may be configured to select a default patient data age threshold that is independent of the relative location. For example, the default patient data age threshold may be a patient data age threshold for proximate devices (e.g., a more stringent threshold), a patient data age threshold for device thresholds (e.g., a more lenient threshold), or an average, weighted average, median, or other patient data age threshold derived from the remote and proximate thresholds. In an implementation, the memory of the auxiliary device 150 may include one look-up table that includes the default patient data age thresholds.

At the stage 70, the method 400 may include comparing the patient data age to the patient data age threshold. For example, the auxiliary device 150 may compare the patient data age to the patient data age threshold selected at the stage 56.

At the stage 76, the method 400 may include controlling the playback interface to provide the patient data and the indication of patient data age based on the comparison. For example, the auxiliary device 150 may control the playback interface 125 to provide the patient data and the indication of patient data age. The indication of patient data age refers to one or more user interface features (e.g., icons, colors, graphics, sounds, and combination thereof) displayed at the playback interface 125. The specific user interface features are discussed in detail below with regard to FIGS. 5A-5J. These features indicate to a user of the playback interface 125 whether or not the patient data age of the displayed patient data is below a patient data age threshold or within a patient data age threshold range. As such, the one or more user interface features are indicative of the comparison between the patient data age and the patient data age threshold. If the patient data age of the displayed data is greater than the maximum patient data age threshold or exceeds the patient data age threshold range, then the displayed patient data may not be clinically actionable data. Conversely, if the patient data age of the displayed data is less than the maximum patient data age threshold or within or below the patient data age threshold range, then the displayed patient data may be clinically actionable data. The indications of patient data age serve to alert and/or warn the caregiver that the displayed patient data may not be clinically actionable data. This patient data may too old, i.e., too far removed in time from the physiological event represented by the data, to serve as a basis for clinical decisions. In some cases, it may be dangerous and possibly life-threatening to base a diagnosis and/or treatment plan on patient data that is too old relative to the time of the corresponding physiological event.

Following the stage 76, the method 400 may return to the stage 50. As indicated by the loop from the stage 76 to the stage 50, at the stage 50, the method 400 may include refreshing the patient data display at the playback interface. For example, the auxiliary device 150 may refresh the patient data display at the playback interface 125, for example in response to receiving additional patient data from the medical device 110 and/or in response to retrieving additional patient data from the reception buffer 222*b* (e.g., as shown in FIG. 14) at the auxiliary device 150. The additional patient data may be of the same type as the patient data received at the stage 50. The conditions determining the transmission age may fluctuate over time, particularly the status of the communication channel. Therefore, the auxiliary device 150 and/or the medical device 110 may dynamically update the transmission age for the patient data as transmission of the patient data proceeds. In an implementation, the user may change the requested playback selection age 633 and/or a requested patient data type following the stage 76 and prior to returning to the stage 50.

In an implementation, a change in the relative location of the medical device 110 to the auxiliary device from proximate to remote or vice versa may require a re-establishment of the communication channel and a new estimation of the transmission age for the patient data. For example, the two devices may lose a WAN connection and re-establish a LAN connection if they move close to one another. For instance, the medical device 110 may be in an ambulance, the auxiliary device 150 may be in a hospital, and these devices may communicate via a WAN. When the ambulance arrives at the hospital, the devices 110 and 150 may re-establish a LAN connection. In an implementation, the change in relative location may not require a re-establishment of the communication channel. For example, the WAN connection for the remotely located devices 110 and 150 may be a cellular network connection that may be maintained when the devices 110 and 150 are proximately located. However, the medical device 110 and/or the auxiliary device 150 may detect the change in location based on access point information and/or an activation of another proximity detection. For example, a Bluetooth LE® or a NFC second connection may be established that does not replace the WAN first connection. However, the devices 110 and/or 150 may detect the presence of the second connection and thus detect proximity. In order to recognize changes in the location of the medical device relative to the auxiliary device, the method 400 may include a re-check of the location of the medical device when the method loops back from the stage 76 to the stage 50. The re-check may occur following the stage 76 and at least prior to reaching the comparison at the stage 70.

Figure 4B:
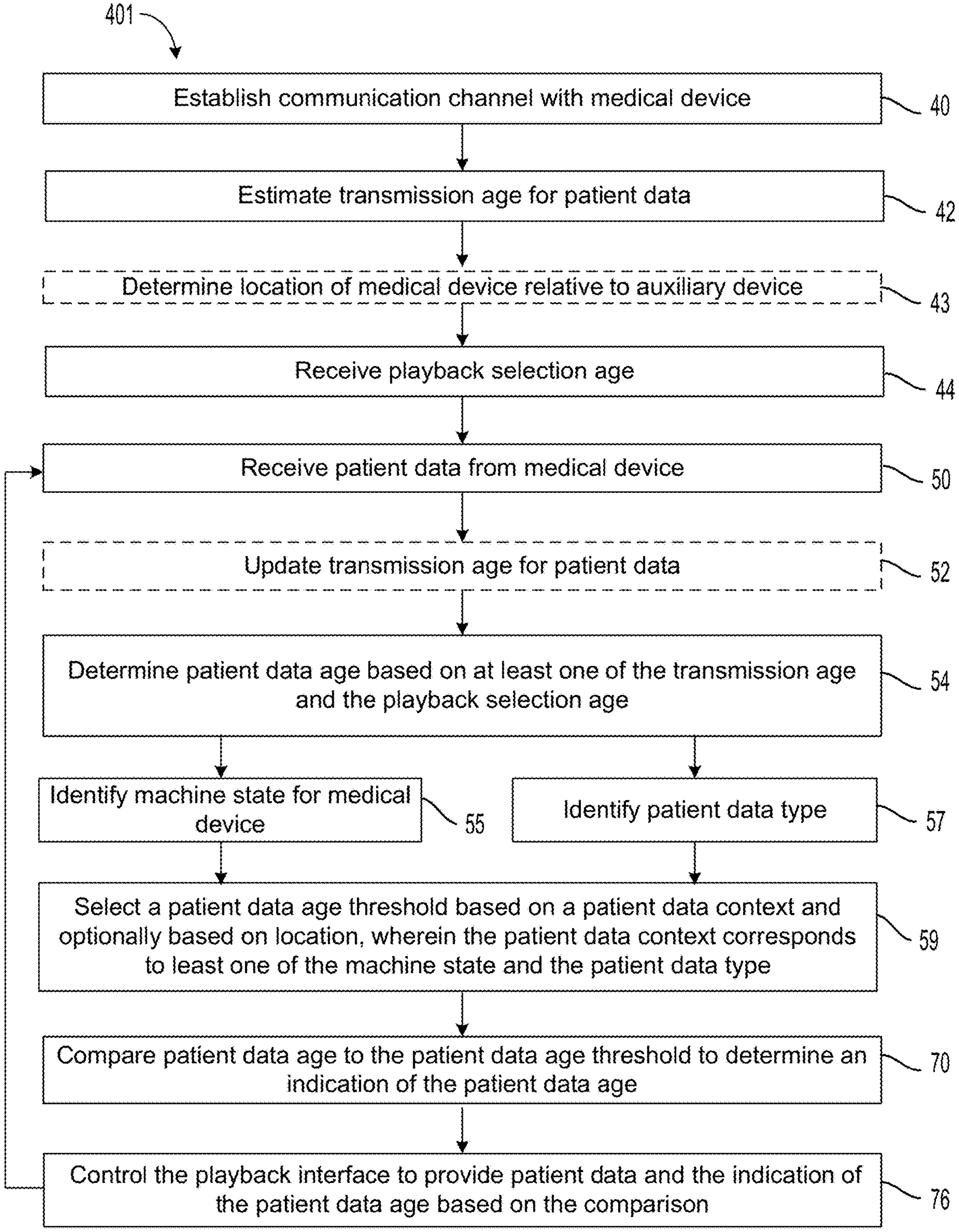
FIG. 4B shows an example process flow of a method for providing patient data and an indication of patient data age at a playback interface.

Referring to FIG. 4B, a method 401 of providing patient data and indication of patient data age at a playback interface is shown. The method 401 is, however, an example only and not limiting. The method 401 can be altered, e.g., by having stages added, removed, rearranged, combined, and/or performed concurrently. Functions described as being performed by the auxiliary device 150 and/or the playback interface 125 may be performed by the processor 220 and/or another component of the auxiliary device 150 as discussed with regard to FIG. 14. Functions described as being performed by the medical device 110 and/or the operational interface 135 may be performed by the processor 120 and/or another component of the medical device 110 as discussed with regard to FIG. 14. In an implementation, the medical device 110 may be the modular medical device 410 and functions performed by the medical device 410 may be performed by the processor 420*a*, 420*b*, and/or another component of the medical device 410 as discussed with regard to FIG. 15.

The stages 40, 42, 43, 44, 50, 52, 54, 70, and 76 are substantially as described above with regard to FIG. 4A. The stages 55, 57, and 59 in the method 401 of FIG. 4B provide an example of an implementation of the stage 56 in the method 400 of FIG. 4A. Specifically, identifying the patient data context may include one or more of identifying a machine state for the medical device and identifying a patient data type and identifying the patient data context based on one or more of the machine state and the patient data type.

At the stage 55, the method 401 includes identifying the machine state for the medical device 110. The machine state of the medical device 110 may indicate a machine configuration and/or operational mode. In an implementation, the medical device 110 may provide machine state information to the auxiliary device 150. The medical device 110 and/or the auxiliary device 150 may identify the machine state based on the machine state information. For example, the machine state information may include an indication of which therapy delivery components 161*a* and/or which sensors 161*b* (e.g., as shown in FIG. 14) are coupled to the medical device 110, are coupled to the patient 101, and/or are operational (e.g., powered on). As a further example, the operational mode may indicate settings or a routine in progress (e.g., adult, pediatric, ALS, BLS, rhythm analysis, etc.) and/or a dashboard in use (e.g., a traumatic brain injury (TBI) dashboard, a ventilation dashboard, a CPR dashboard, etc.).

At the stage 57, the method 401 includes identifying the patient data type. In various implementations, the type of patient data may be ECG data, flow sensor data, accelerometer data, capnography data, pulse oximetry data, blood pressure data, etc. In general, the type of patient data may be any type of data available to the medical device 110 via the patient interface devices 160 (e.g., as shown in FIG. 1A and FIG. 14).

At the stage 59, the method 401 includes selecting a patient data age threshold based on a patient data context and optionally based on location, wherein the patient data context includes at least one of the machine state and the patient data type. The auxiliary device 150 may select the patient data age threshold based on thresholds in Table 1 or Table 2, or based on a threshold derived therefrom. For example, the machine state may be a display of the TBI dashboard and the patient data type may be NIBP. For proximate devices, referring to Table 1, the patient data age threshold may be 10-30 seconds. For remote devices, referring to Table 2, the patient data age threshold may be 30-60 seconds. If the location information is not available, then the one or the other of the proximate or the remote locations may be a default. In an implementation, the patient data context may only include the patient data type. As seen in Tables 1 and 2, some thresholds apply to many machine states. Therefore, the auxiliary device 150 may select a default value for the threshold that does not depend on the machine state. In an implementation, the patient data context may only include the machine state and the auxiliary device may select a default value for a threshold for any waveform or for any discrete measurement irrespective of the particular data type. For example, if the machine state is patient monitoring, the threshold may be 1-2 seconds for all waveform data and 10-30 seconds for all discrete measurements.

As indicated by the loop from the stage 76 to the stage 50, at the stage 50, the method 401 may include refreshing the patient data display at the playback interface. For example, the auxiliary device 150 may refresh the patient data display at the playback interface 125, for example in response to receiving additional patient data from the medical device 110 and/or in response to retrieving additional patient data from the reception buffer 222*b* (e.g., as shown in FIG. 14) at the auxiliary device 150. The additional patient data may be of the same type as the patient data received at the stage 50.

As similarly described above with regard to the method 400 in FIG. 4A, the method 401 in FIG. 4B may include a re-evaluation of the medical device location relative to the auxiliary device 150 subsequent to the stage 76. Further, the method 401 may include a re-establishment of the communication channel and new estimation of the transmission age of the patient data.

Figure 4C:
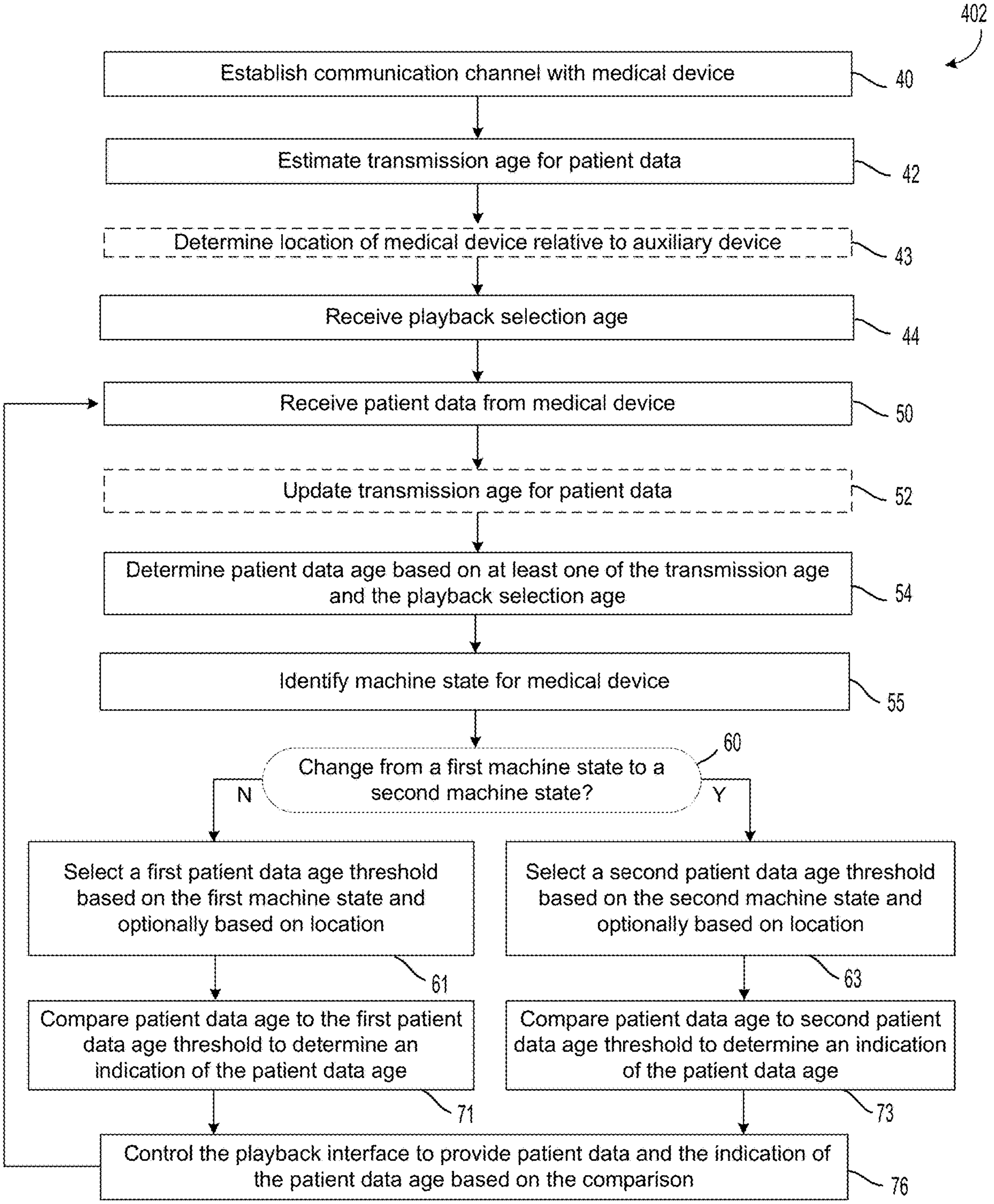
FIG. 4C shows an example process flow of a method for providing patient data and an indication of patient data age at a playback interface.

Referring to FIG. 4C, a method 402 of providing patient data and indication of patient data age at a playback interface is shown. The method 402 is, however, an example only and not limiting. The method 402 can be altered, e.g., by having stages added, removed, rearranged, combined, and/or performed concurrently. Functions described as being performed by the auxiliary device 150 and/or the playback interface 125 may be performed by the processor 220 and/or another component of the auxiliary device 150 as discussed with regard to FIG. 14. Functions described as being performed by the medical device 110 and/or the operational interface 135 may be performed by the processor 120 and/or another component of the medical device 110 as discussed with regard to FIG. 14. In an implementation, the medical device 110 may be the modular medical device 410 and functions performed by the medical device 410 may be performed by the processor 420*a*, 420*b*, and/or another component of the medical device 410 as discussed with regard to FIG. 15.

The stages 40, 42, 43, 44, 50, 52, 54, 55, and 76 are substantially as described above with regard to FIGS. 4A and/or 4B. The stages 60, 61, 63, 71, and 73 in the method 402 of FIG. 4C enable a response to a change in the machine state identified at the stage 55.

Since review of the patient data at the playback interface 125 may occur during ongoing medical treatment and/or monitoring of the patient 101 with the medical device 110, it is possible that the machine state of the medical device 110 may change during the patient data review. Therefore, it may be necessary to select a different threshold in response to the change in the machine state. For example, if the medical device 110 changes from a monitoring mode to a rhythm analysis mode in preparation for defibrillation, the clinically tolerable latency of the patient data may decrease.

As indicated by the loop from the stage 76 to the stage 50, at the stage 50, the method 402 may include refreshing the patient data display at the playback interface. For example, the auxiliary device 150 may refresh the patient data display at the playback interface 125, for example in response to receiving additional patient data from the medical device 110 and/or in response to retrieving additional patient data from the reception buffer 222*b* (e.g., as shown in FIG. 14) at the auxiliary device 150. The additional patient data may be of the same type as the patient data received at the stage 50.

At the stage 60, the method 402 includes detecting a change from a first machine state to a second machine state. The second machine state may be different from the first machine state. The auxiliary device 150 may detect the change in machine state based on machine state information received from the medical device 110 with the patient data. In an implementation, with each subsequent refresh cycle for the playback interface 125, the auxiliary device 150 may compare a current machine state with a previous machine state to detect the change in the machine state since the previous refresh cycle. For example, the medical device 110 may transmit patient data in a patient monitoring mode, e.g., a first machine state, switch to the heart rhythm analysis mode, and send a subsequent patient data in the heart rhythm analysis mode, e.g., the second machine state. In the absence of the change in machine state, the method 402 may proceed to the stages 61 and 71. In the presence of the change in machine state, the method 402 may proceed to the stages 63 and 73. For example, the processor is configured to compare the patient data age to the first patient data age threshold when the medical device is in the first machine state and to compare the patient data age to the second patient data age threshold in response to the medical device changing from the first machine state to the second machine state.

At the stage 61, the method 402 includes selecting a first patient data age threshold based on the first machine state and optionally based on location. For example, similarly to the stage 59 of FIG. 4B, the auxiliary device 150 may select the first patient data age threshold from the one or more look-up tables. If there is no change in the machine state detected at the stage 60, then the first patient data age threshold may be the same as a most recently and previously determined patient data age threshold. Thus, the auxiliary device 150 may use the first patient data age threshold for multiple cycles without change in the absence of the change in the machine state.

At the stage 71, the method 402 includes comparing the patient data age to the first patient data age threshold to determine the indication of the patient data age. For example, similarly to the stage 70 of FIG. 4B, the auxiliary device 150 may compare the patient data age to the first patient data age threshold.

At the stage 63, the method 402 includes selecting a second patient data age threshold based on the second machine state and optionally based on location. For example, similarly to the stage 59 of FIG. 4B, the auxiliary device 150 may select the second patient data age threshold from the one or more look-up tables. If there is a change in the machine state detected at the stage 60, then the second patient data age threshold may be different from the most recently and previously determined patient data age threshold. The auxiliary device 150 may continue use of the second patient data age threshold for multiple cycles without change in the absence of an additional change in the machine state. In the event of the additional change in the machine state, the auxiliary device 150 may select a third patient data age threshold which may or may not be the same as one or more thresholds used prior to the second patient data age threshold.

At the stage 73, the method 402 includes comparing the patient data age to the second patient data age threshold to determine the indication of the patient data age. For example, similarly to the stage 70 of FIG. 4B, the auxiliary device 150 may compare the patient data age to the second patient data age threshold.

Figure 4D:
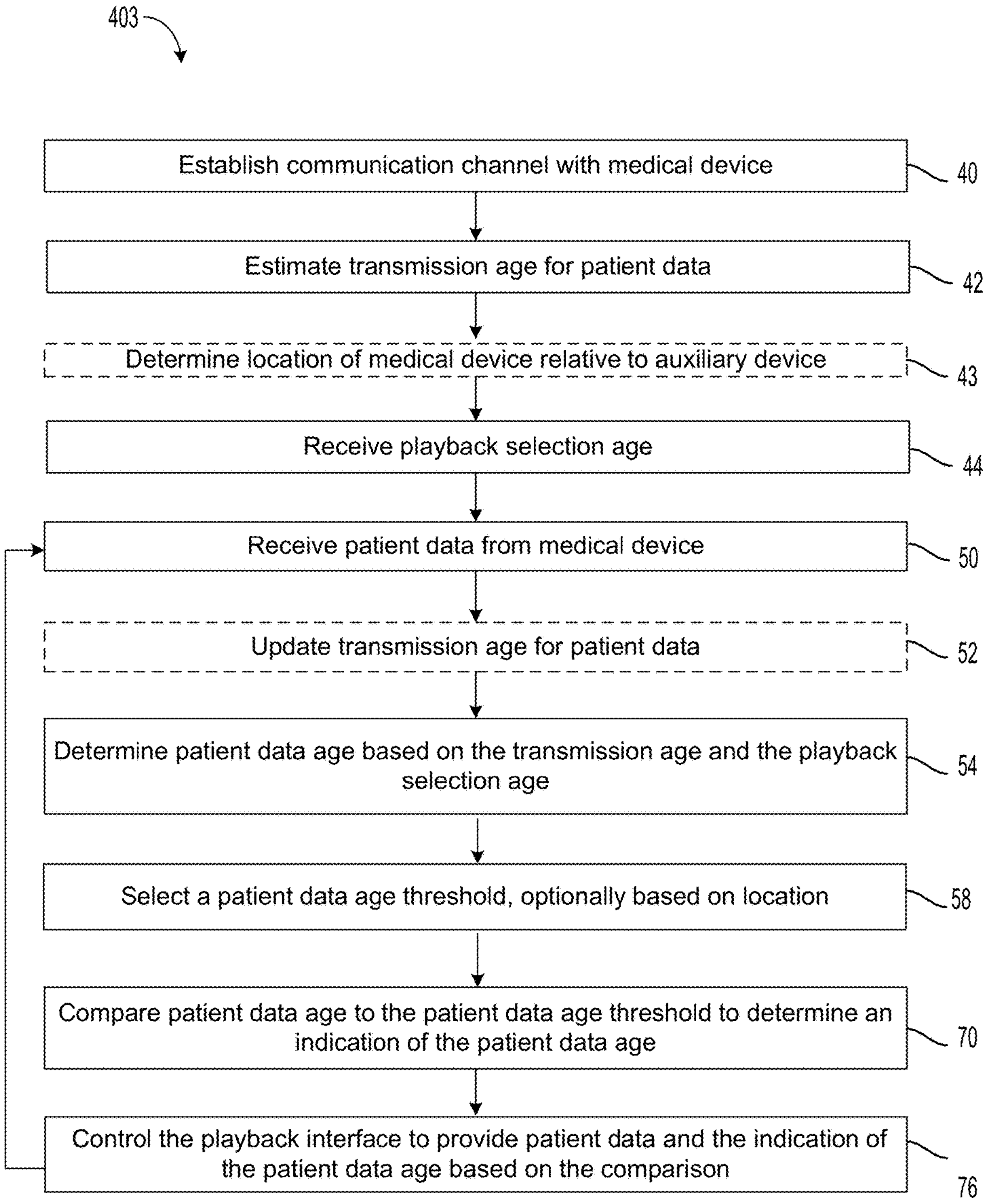
FIG. 4D shows an example process flow of a method for providing patient data and an indication of patient data age at a playback interface.

Referring to FIG. 4D, a method 403 of providing patient data and indication of patient data age at a playback interface is shown. The method 403 is, however, an example only and not limiting. The method 403 can be altered, e.g., by having stages added, removed, rearranged, combined, and/or performed concurrently. Functions described as being performed by the auxiliary device 150 and/or the playback interface 125 may be performed by the processor 220 and/or another component of the auxiliary device 150 as discussed with regard to FIG. 14. Functions described as being performed by the medical device 110 and/or the operational interface 135 may be performed by the processor 120 and/or another component of the medical device 110 as discussed with regard to FIG. 14. In an implementation, the medical device 110 may be the modular medical device 410 and functions performed by the medical device 410 may be performed by the processor 420*a*, 420*b*, and/or another component of the medical device 410 as discussed with regard to FIG. 15. The stages 40, 42, 43, 44, 50, 52, 54, 70, and 76 are substantially as described above with regard to FIG. 4A.

At the stage 58, the method 403 includes selecting a patient data age threshold, optionally based on location. In an implementation, the auxiliary device 150 may select a default patient data age threshold that is independent of the patient data context. For example, the playback interface 125 may include a pre-determined and/or pre-programmed default patient data age threshold. Optionally, in the method 403, the stage 58 may include selecting the patient data age threshold based on the patient data context. As a further option, in the method 403, the stage 58 may include selecting the patient data age threshold based on location. For example, the playback interface 125 may include a first default patient data age threshold for proximate devices that is independent of the patient data context. As another example, the playback interface 125 may include a second default patient data age threshold for remote devices that is independent of the patient data context. In an implementation, in the method 403, the stage 58 may include selecting the patient data age threshold based on the patient data age context and the location. In regard to the method 403, the patient data age context may include one or more of the machine state and the type of patient data.

Figure 5A:
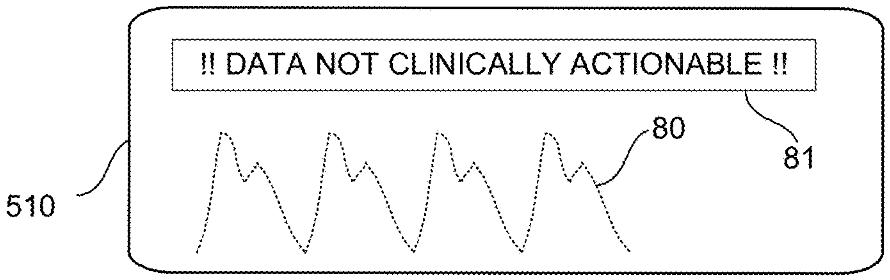
FIG. 5A shows an example of a textual indication of patient data age at the playback interface.

Referring to FIGS. 5A-5J, examples of indications of patient age at the playback interface are shown. FIG. 5A shows an example of a textual indication of patient data age at the playback interface. In an implementation, the auxiliary device 150 may control the playback interface 125 to display the textual indication 81 of patient data age for the patient data 80. The playback interface 125 may provide the patient data 80 and the textual indication 81 in the data display window 510. The patient data 80 is shown in FIG. 5A as a waveform as an example only and the textual indication 81 may appear with waveform data, time trend data, discrete data, and/or other patient data available at the playback interface 125. The textual indication 81 may provide, for example, a warning, instructions, recommendations, and/or time stamp information. The playback interface 125 may provide the textual indication 81 if the patient data age for the displayed patient data 80 exceeds a patient data age threshold and/or is outside of a patient data age threshold range (e.g., the threshold comparison described with regard to FIGS. 4A-4D).

Figure 5B:
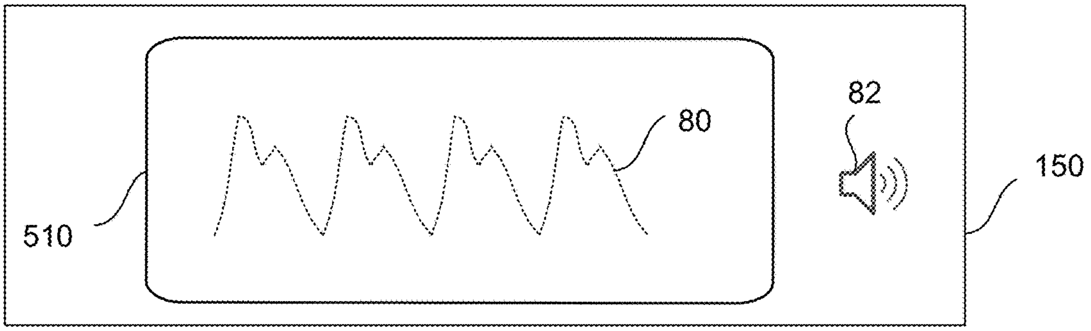
FIG. 5B shows an example of an audible indication of patient data age at the auxiliary device.

FIG. 5B shows an example of an audible indication of patient data age at the auxiliary device. In an implementation, the auxiliary device 150 may control an output device, for example, a speaker 82, to provide an audible indication of patient data age for the patient data 80. The playback interface 125 may provide the patient data 80 in the data display window 510. The patient data 80 is shown in FIG. 5B as a waveform as an example only and the speaker 82 may provide the audible indication with waveform data, time trend data, discrete data, and/or other patient data available at the playback interface 125. The audible indication may provide, for example, an alarm and/or verbal instructions, verbal recommendations, and/or verbal time stamp information. The speaker 82 may provide the audible indication if the patient data age for the displayed patient data 80 exceeds a patient data age threshold and/or is outside of a patient data age threshold range (e.g., the threshold comparison described with regard to FIGS. 4A-4D).

Figure 5C:
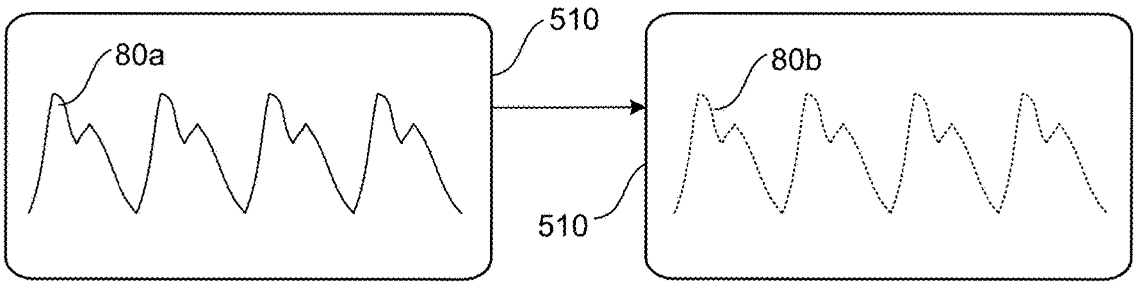
FIGS. 5C and 5D show examples of a graphic indication of patient data age at the playback interface.
Figure 5D:
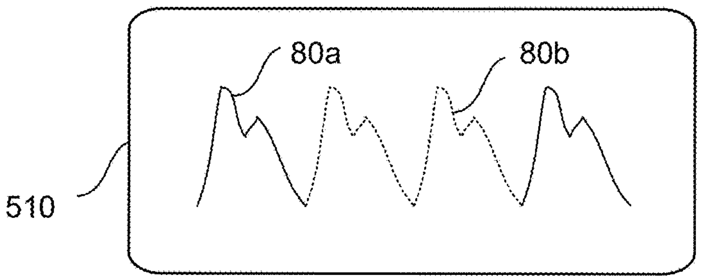

FIGS. 5C and 5D show examples of graphic indications of patient data age at the playback interface. In an implementation, the auxiliary device 150 may control the playback interface 125 to provide graphic indications of patient data age. The playback interface 125 may provide the patient data (e.g., solid line patient data 80*a* and dotted line patient data 80*b*) in the data display window 510. The waveform data is shown in FIGS. 5C and 5D waveforms as examples only and the playback interface 125 may provide the graphic indications with waveform data, time trend data, discrete data, and/or other patient data available at the playback interface 125. The playback interface 125 may change the appearance of the patient data if the patient data age exceeds a patient data age threshold and/or is outside of a patient data age threshold range (e.g., the threshold comparison described with regard to FIGS. 4A-4D). For example, when the patient data age is below the patient data age threshold or within the patient data age threshold range, the playback interface 125 may provide solid line patient data 80*a*. When the patient data age is above the patient data age threshold or outside the patient data age threshold range, the playback interface 125 may provide broken or dotted line patient data 80*b*. As shown in FIG. 5D, if the patient data age changes during the patient data review, the playback interface 125 may switch the display between the solid line patient data 80*a* and the dotted line patient data 80*b*. The broken line and solid line representations in FIGS. 5C and 5D are examples only and other appearance changes are within the scope of the disclosure. For example, the playback interface may change the gray scale or a color of the displayed patient data.

Figure 5E:
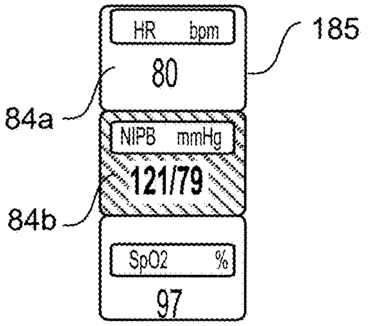
FIGS. 5E and 5F show examples of color changes as indication of patient data age at the playback interface.
Figure 5F:
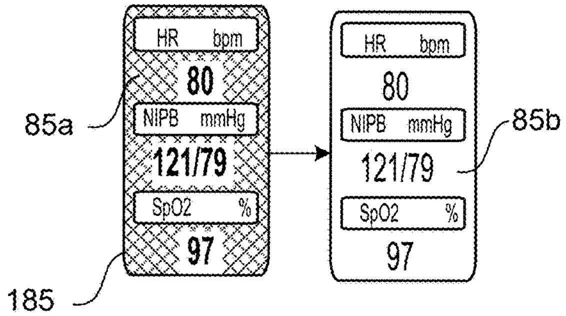

FIGS. 5E and 5F show examples of color changes as indication of patient data age at the playback interface. In an implementation, the auxiliary device 150 may control the playback interface 125 to provide a color change indication of patient data age for the discrete physiological measurement data 185. The discrete physiological measurement data 185 shown in FIGS. 5E and 5F is an example only and the playback interface 125 may provide color changes with waveform data, time trend data, discrete data, and/or other patient data available at the playback interface 125. The playback interface 125 may change the color of the patient data if the patient data age exceeds a patient data age threshold and/or is outside of a patient data age threshold range (e.g., the threshold comparison described with regard to FIGS. 4A-4D). For example, when the patient data age is below the patient data age threshold or within the patient data age threshold range, the playback interface 125 may provide the patient data with a first color 84*a*. When the patient data age is above the patient data age threshold or outside the patient data age threshold range, the playback interface 125 may provide the patient data with a second color 84*b*. As discussed in regard to FIG. 1C, the medical device 110 may receive the discrete data in response to a user request or an automated machine request. The medical device 110 may receive each type of discrete data at a different time and/or at different time intervals and may transmit each type of discrete data to the auxiliary device 150 at different times and/or different time intervals. Therefore, the transmission age associated with each type of discrete data may vary. As shown schematically in FIG. 5E, the playback interface 125 may display one or more first types of discrete data with the first color 84*a* (e.g., the heart rate and SpO2) and may display one or more second types of discrete data with the second color 84*b* (e.g., the NIBP). As shown in FIG. 5F, if the patient data age changes during the patient data review, the playback interface 125 may switch the display between a first color 85*a* and a second color 85*b*.

Figure 5G:
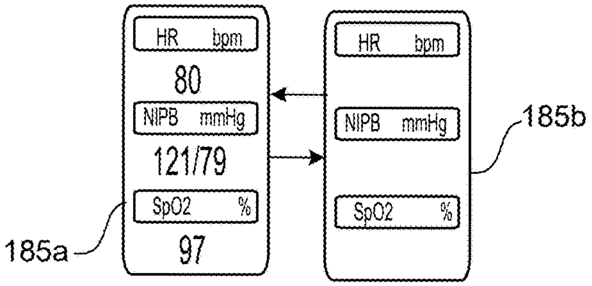
FIG. 5G shows an example of flashing data as indication of patient data age at the playback interface.

FIG. 5G shows an example of flashing data as indication of patient data age at the playback interface. In an implementation, the auxiliary device 150 may control the playback interface 125 to cyclically display and conceal patient data (e.g., provide flashing or blinking patient data instead of continuously displayed data) as an indication of patient data age. FIG. 5G schematically shows displayed discrete data 185*a* and concealed discrete data 185*b* with arrows indicating that the playback interface 125 may alternate between these two states. The discrete data 185 shown in FIG. 5G is an example only and the playback interface 125 may provide flashing data for with waveform data, time trend data, discrete data, and/or other patient data available at the playback interface 125. The playback interface 125 may provide flashing or blinking patient data if the patient data age exceeds a patient data age threshold and/or is outside of a patient data age threshold range (e.g., the threshold comparison described with regard to FIGS. 4A-4D). When the patient data age is below the patient data age threshold or within the patient data age threshold range, the playback interface 125 may steadily display the patient data. As discussed in regard to FIG. 1C, the medical device 110 may receive the discrete data in response to a user request or an automated machine request. The medical device 110 may receive each type of discrete data at a different time and/or at different time intervals and may transmit each type of discrete data to the auxiliary device 150 at different times and/or different time intervals. Therefore, the transmission age associated with each type of discrete data may vary. As a result, the playback interface 125 may steadily display one or more first types of discrete data and may flash one or more second types of discrete data.

Figure 5H:
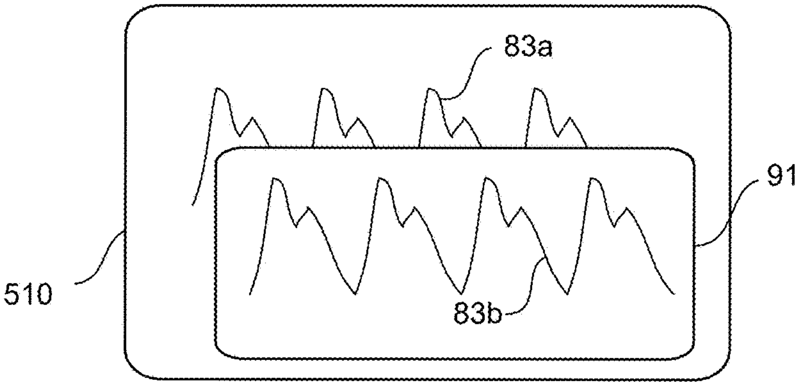
FIG. 5H shows an example of a pop-up window for indication of patient data age at the playback interface.

FIG. 5H shows an example of a pop-up window for indication of patient data age at the playback interface. In an implementation, the auxiliary device 150 may control the playback interface 125 to display a pop-up window 91. The playback interface 125 may provide the pop-up window 91 in the data display window 510. The patient data 83*a*, 83*b* is shown in FIG. 5H as a waveform as an example only and the pop-up window 91 may appear with waveform data, time trend data, discrete data, and/or other patient data available at the playback interface 125. In the example of FIG. 5H, the patient data age for the patient data 83*a* may exceed a patient data age threshold and/or be outside of a patient data age threshold range (e.g., the threshold comparison described with regard to FIGS. 4A-4D). The playback interface may display patient data 83*b* with a patient data age that is below the patient data age threshold or within the patient data age threshold range in the pop-up window 91. Such a display configuration may indicate to the user that the patient data 83*a* may not be clinically actionable data and may force the user to view clinically actionable data in the pop-up window 91.

Figure 5I:
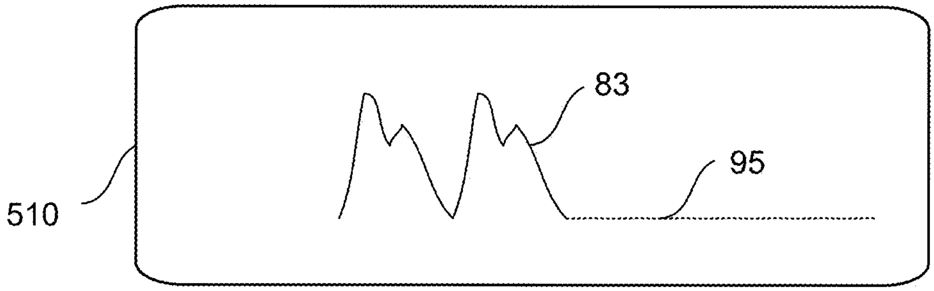
FIGS. 5I and 5J show examples of indications of a loss of data transmission through a communication channel.
Figure 5J:
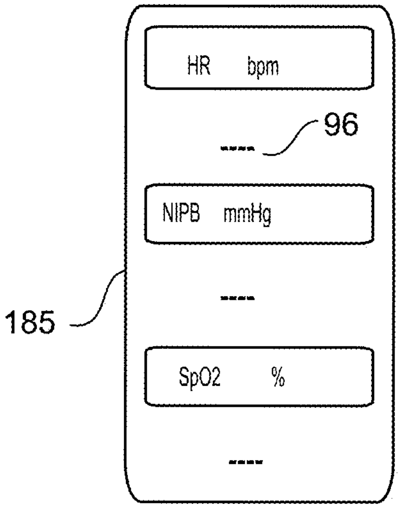

FIGS. 5I and 5J show examples of indications of a deterioration of data transmission through a communication channel. The deterioration of data transmission may drastically increase the age of the patient data and/or result in a lapse in reception of patient data. During the review of patient data at the playback interface 125, there may be a lapse in data reception at the auxiliary device 150. For example, the communication channel 399 may be alive but the latency associated with the communication channel 399 may increase. As a result, the auxiliary device 150 may exhaust the reception buffer (e.g., the reception buffer 222*b* as shown in FIG. 14). The playback interface 125 may continue to display previously received and stored historic data but may cease to provide current time patient data 83. If the user of the playback interface 125 requests a playback interval that includes only historic data, then the playback interface 125 may provide this data irrespective of changes in the communication channel 399. However, if the user of the playback interface 125 requests current data, the playback interface 125 may display a flat dashed line 95 or a flat dashed line 96 in place of the current time patient data 83 to indicate that there is no current data available at the auxiliary device 150. If data reception resumes at the auxiliary device 150, then the playback interface 125 may resume display of the patient data and may include an indication of the patient data age. If there is a disconnection of the communication channel 399, then the playback interface 125 may provide a textual, graphic, and/or audible message indicative of a loss of communicative coupling between the medical device 110 and the auxiliary device 150. These devices may then re-establish or attempt to re-establish the communication channel 399.

Figure 6:
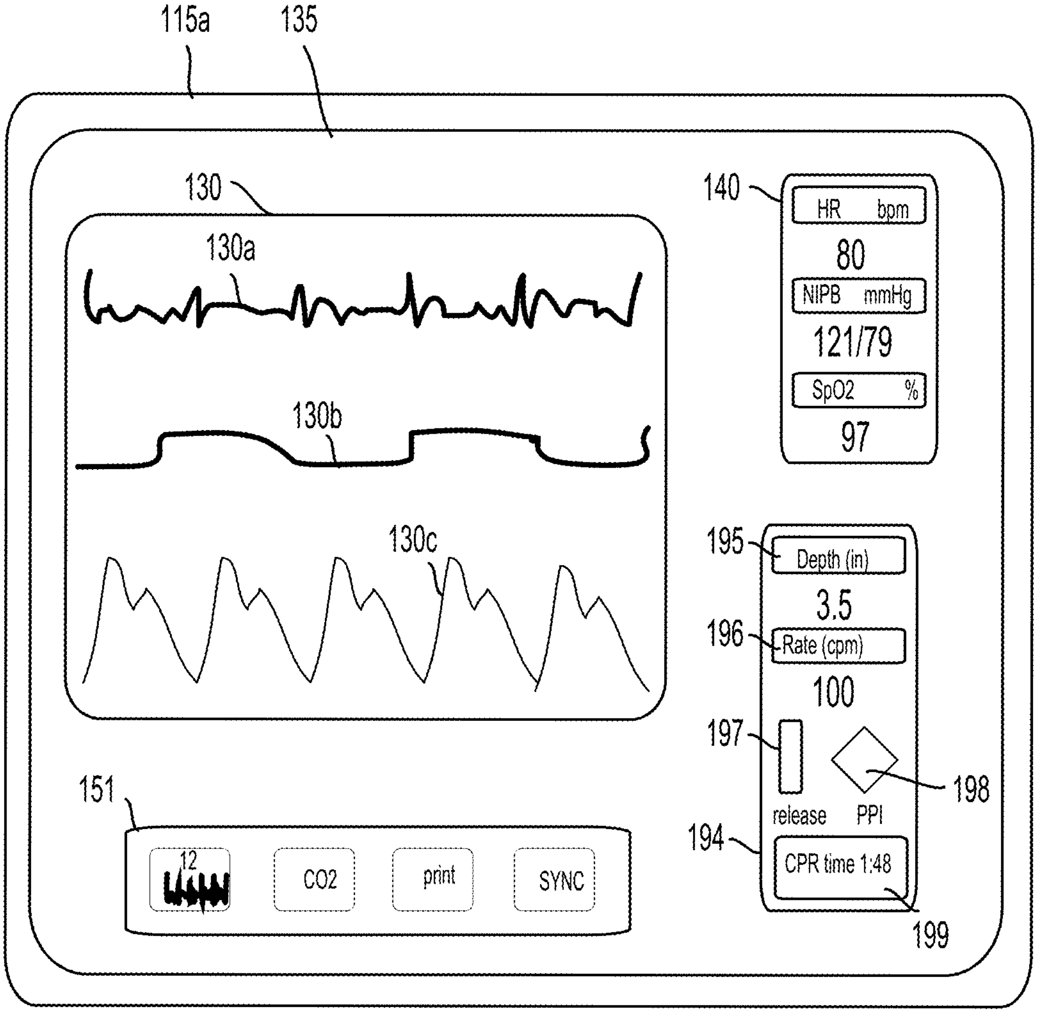
FIG. 6 shows an example of an operational interface.

Referring to FIG. 6 with further reference to FIG. 1A, an example of an operational interface is shown. A display screen 115*a* of the medical device 110 may be configured to provide the operational interface 135. The operational interface 135 may provide operational information that includes the patient data. For example, the patient data may include physiological measurements 140 that correspond to a particular point in time (e.g., discrete physiological measurements). The physiological measurements 140 may include, for example, blood pressure (e.g., non-invasive blood pressure (NIBP) and/or invasive blood pressure (IBP)), heart rate, respiration rate, temperature, oxygen saturation (e.g., SpO2), end tidal carbon dioxide (e.g., EtCO2), Near Infrared Spectroscopy (NIRS) measurements, and/or other physiological parameters. As another example, the operational information may include physiological waveforms 180 and/or time trends (e.g., body temperature time trends, heart rate time trends, respiration rate time trends, and/or other time trends). The waveforms may correspond to physiological sensor data received substantially continuously as a function of time, such as an electrocardiogram (ECG) 130*a*, a capnography waveform 130*b* (e.g., end tidal carbon dioxide (EtCO2)), and/or an oxygen saturation (e.g., SpO2) waveform 130*c*. The operational information may further include medical care delivery parameters such as CPR performance parameters 194. The CPR performance parameters 194 may include for example, a compression depth 195, a compression rate 196, a chest release indicator 197, a perfusion performance indicator 198, and a CPR time indicator 199. In an implementation, the CPR performance parameters 194 may include blood pressure data and/or blood flow data. These examples of patient data are not limiting of the disclosure as other types of data corresponding to various medical devices are within the scope of the disclosure. The operational interface 135 may further include one or more soft-key labels 151 and/or other controls (e.g., touch screen buttons) for operation of the medical device 110. For example, the other controls may determine operational parameters and/or care delivery parameters for the medical device 110. The operational interface may display and/or otherwise provide the patient data in real-time as it is captured, generated, and/or collected by the medical device during an ongoing medical event. Thus, the user may view the patient data in real-time at the operational interface 135 in order to effectively administer care to the patient.

Figure 7:
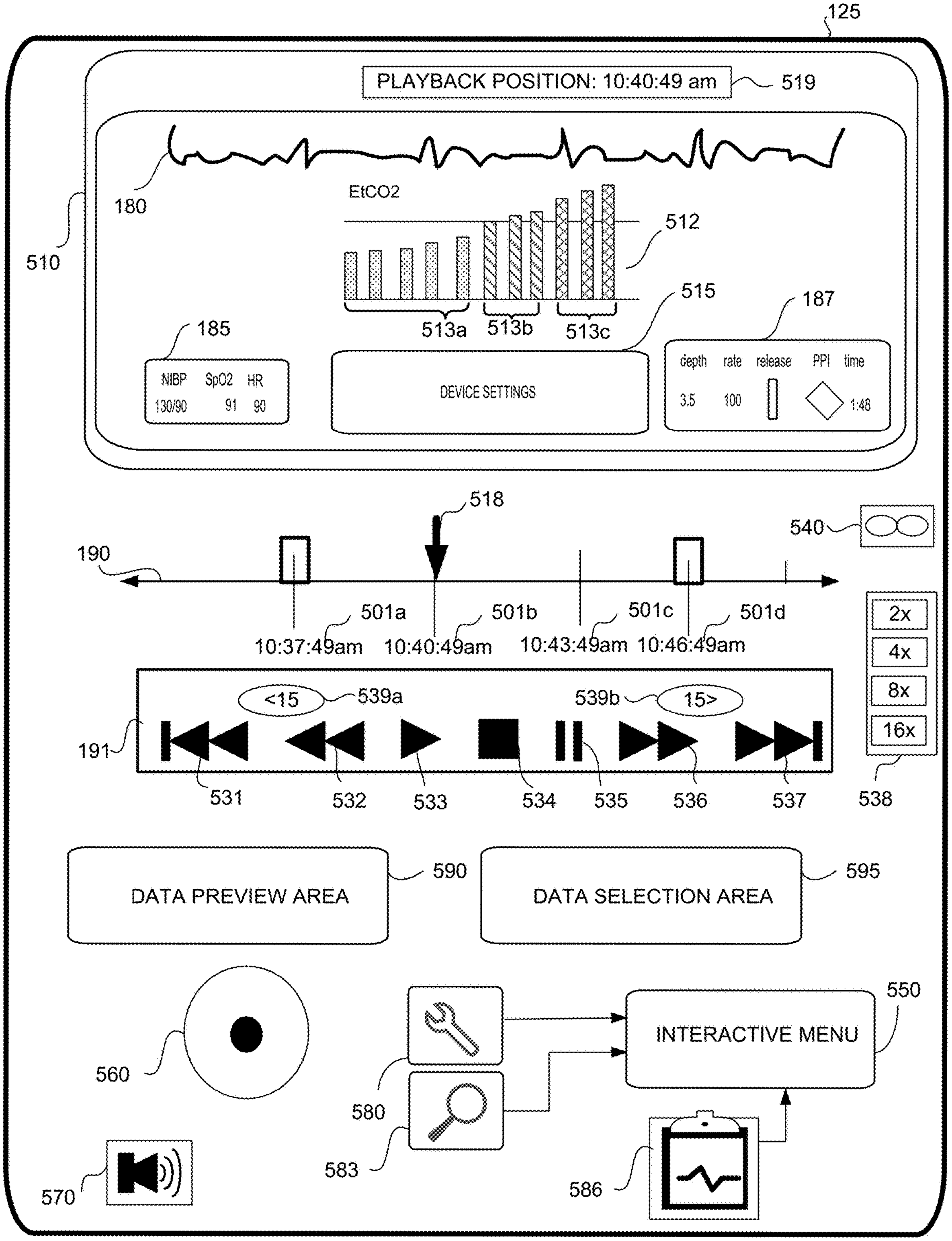
FIG. 7 shows a schematic diagram of an example of a playback interface.

Referring to FIG. 7, a schematic diagram of an example of the playback interface is shown. The playback interface 125 may receive the patient data as image format data that constitutes a snapshot of the visual representation of that data on the operational interface 135. The playback interface 125 may display the snapshot and, as such, the visual representation of the data on the playback interface 125 may replicate and redisplay the visual representation of the data that matches a previously rendered image at the operational interface 135. Alternatively, the playback interface 125 may not replicate and redisplay the visual representation of the data that matches the previously rendered image of the data at the operational interface 135. Rather, the processor controlling the playback interface 125 may receive non-image format data and generate the visual representation of the data for the playback interface 125 based on the non-image format data. Therefore, the visual representation of the patient data on the playback interface 125 may be different from the visual representation of the same patient data at the operational interface 135, for example, the visual representation on the playback interface 125 may be rendered or otherwise displayed in a format and/or layout that differs from how the data was displayed on the operational interface.

The playback interface 125 may include the data display window 510. In an implementation, the data display window 510 may display visual representations of a physiological waveform 180 and/or of a discrete physiological measurement data 185, and/or of CPR performance parameters 187, and/or of a time trend 512 (e.g., the time trend 512 for EtCO2 includes a bar graph as an example, but the time trend may be line graph or another graph indicative of a value of a discrete variable as a function of time). The visual representations may include graphical representations, numerical representations, textual representations, etc.

The time trend 512 may provide a visual representation of trending data from signals indicative of a physiological parameter such as for example, ECG, systolic blood pressure, end tidal carbon dioxide (EtCO2), blood oxygen saturation (SpO2), etc. Trending data may be displayed as a running record of previous readings. The oldest readings may appear on the left, and the newest readings may appear on the right. The newest reading may be inserted on the right side while displacing the oldest reading on the left side. Alternatively, the oldest readings may appear on the right and the newest readings may appear on the left. The newest reading may be inserted on the left side while displacing the oldest reading on the right side. Other options for visually indicating the trend data for a given signal may be employed. For example, a time trend for EtCO2 is shown as a bar graph 512.

In an implementation, the playback interface 125 may scale the time trend data, adjust the frequency of the values displayed for the time trend data, and/or adjust a pattern and/or color with which the trending values are displayed according to the particular patient and/or the patient's condition. These features may convey information about how the trending values compare with acceptable values or ranges of values, or user-defined values or ranges of values. For example, in the bar graph 512, the playback interface 125 may display the five bars 513*a* on the left with a first pattern and/or color to indicate that the patient's EtCo2 at the times corresponding to those particular measurements was or is at a critical level far below acceptable ranges. The playback interface 125 may display the middle three bars 513*b* with a second pattern and/or color to indicate that EtCo2 at the times corresponding to those particular measurements was or is below acceptable limits, but not at a critical level. The right three bars 513*c* may exhibit a third pattern and/or color to indicate that the patient's EtCo2 at the times corresponding to those particular measurements was within acceptable limits for the patient's age. The color of other information on the playback interface 125 may change based on a target and/or desired range for a particular parameter. Further the playback interface 125 may display a target value and/or a range (e.g., with a numerical indicator and/or a graphical indicator).

In an implementation, the data display window 510 may include a device settings window 515. The device settings window 515 may provide device settings associated with the displayed patient data based on time. The device settings may correspond to the settings, status, activities, etc. of the device that collected the displayed patient data at the time corresponding to the displayed patient data. For example, the device settings window 515 may provide battery status information, heart rhythm analysis information, shock delivery information, and/or other therapy delivery information. The shock delivery information and/or the therapy delivery information may correspond to the device settings at the time of shock or other therapy delivery (e.g., energy, flow rate, start time, stop time, compression rate, compression depth, etc.). For example, the device settings window 515 may provide at least a portion of the information in Table 3 below. Such information may enable the user of the playback interface 125 to evaluate the displayed patient data in light of the device settings, status, and/or activities at the time of data collection.

The playback interface 125 may include the interactive timeline 190. The information provided in the data display window 510 may correspond to a time as indicated by the interactive timeline 190. The interactive timeline 190 is shown as a substantially linear timeline however this is an example only and other non-linear timelines are within the scope of the disclosure. The times (e.g., 501*a*, 501 *b*, 501*c*, 501*d*) represented on the interactive timeline 190 are representative of the time stamps associated with the sensor data. The medical device 110 may determine the time stamps and include the time stamps with the patient data sent to the auxiliary device 150. Each time stamp may be an absolute clock time (e.g., from the clock associated with the medical device 110) or an elapsed time. For example, the elapsed time may be an elapsed time from a particular event within the medical encounter such as turn-on of the medical device, a first ECG of the patient, a defibrillation shock administration, a drug delivery, a pacing therapy administration, etc.

As discussed above, the interactive timeline 190 may include the playback pointer 518. During playback of patient data in the data display window 510, the playback pointer 518 may automatically move along the interactive timeline 190 synchronously with the playback of the patient data in terms of time. Thus, the playback pointer 518 may dynamically indicate the time associated with the patient data shown in the data display window 510 during playback. In an implementation, the data display window 510 may include a playback position indicator 519 that indicates a numeric representation of the time on the interactive timeline 190 associated with the playback pointer 518.

The playback interface 125 may include a media navigation bar 191. The media navigation bar 191 may include user interactive data display controls for the data displayed in the data display window 510. The user interactive data display controls may capture user input indicative of data display parameters for the playback interface. As used at least with regard to the media navigation bar 191, "control" refers to either or both of a physical button or a virtual/screen selection interface option. For example, the media navigation bar 191 may include a rewind control 532, a play control 533, a stop control 534, a pause control 535, and a fast forward control 536. The bar 191 may further include a skip back control 531, and skip forward control 537. These user interactive data display controls may enable the user to control the playback of the patient data at the playback interface 125. These controls may determine a time during the medical event at which to begin and/or end data playback, a speed at which to provide the playback, and/or initiate a start and/or stop of the patient data playback. The skip back control 531 and the skip forward control 537 may enable the playback interface 125 to select a time corresponding the beginning or the end of a data record or a section of a data record. These controls may enable the user to review data according to a user-selected sequence and skip between medical events, chapters, and/or visual event indicators 620.

In an implementation, the playback interface 125 may include one or more of a jump-back control 539*a* and a jump-forward control 539*b*. For example, the media navigation bar 191 may include these controls. The jump-back control 539*a* and the jump-forward control 539*b* may change the time of the displayed patient data by a preconfigured interval. The preconfigured interval may be, for example, 5 seconds, 10 seconds, 15 seconds, 30 seconds, 60 seconds, 120 seconds, 180 seconds, or another suitable time period. In an implementation, the playback interface 125 may enable the jump-back control 539*a* and the jump-forward control 539*b* once the playback of the patient data is underway.

The time selection controls (e.g., the skip back control 531, the skip forward control 537, the jump-back controls 539*a* and 539*b*, and/or the one or more time interval selectors 622*a* and 622*b*) may permit the user of the playback interface 125 to selectively review data at times at which significant events of interest occurred. The time interval selectors may indicate a data window. In contrast, without these selection features, the reviewer may have to review a sequence of captured data in chronological order and some or most of the sequence may not include data of interest to the reviewer.

In an implementation, the playback interface 125 may include a playback speed selection bar 538. The playback interface 125 may present the patient data at a default playback speed. By clicking on or otherwise selecting one of the 2×, 4×, 8×, or 16× portions of the playback speed selection bar 538, the user may adjust the presentation speed for the patient data to a speed other than the default speed. In an implementation, the playback speed may be a multiplier applied to the default playback speed. The playback speed may be, for example, but not limited to, 2×, 4×, 8×, or 16× this default playback speed. The user may adjust the playback speed to change the duration of the patient data playback. For example, at the default speed, the playback duration for the patient data of interest may be 12 minutes. The user may select a 4× playback speed to reduce the playback duration to three minutes. In an implementation, the playback speed may be continuously configurable between a range of speeds (e.g., 0.25×-4×) rather than a discrete speed setting (e.g., 2×, 4×). For example, the low end of the speed range might be as low as 0.250×, 0.5×, or 2×. The high end of the speed range might be at least 2×, 4×, 8×, 16×, 32×. In an implementation, the playback speed selection bar 538 may be configured to visually indicate a currently active playback speed selection.

In an implementation, the selected playback speed or the default playback speed may be the same speed at which at which the operational interface 135 displays the patient data. For example, the operational interface 135 may display waveform and/or time trend data at a sweep speed. The sweep speed may be a user configurable speed and the operational interface 135 may display the waveform and/or time trend data at a default speed or at a user selected speed. In an implementation, the playback interface 125 may receive a current sweep speed setting from the operational interface 135 in order to match or apply a multiplier to the current sweep speed. As examples, the sweep speed may be a speed in a range of approximately 1 mm/sec-50 mm/sec. For example, the sweep speed may be approximately 3 mm/sec, 6 mm/sec, 12.5 mm/sec, 25 mm/sec, or 50 mm/sec. The default sweep speed and/or speed options provided for a user configuration may depend on the particular data in the time trend and/or waveform. For example, ECG data may correspond to different default and/or options for the sweep speed than CO2 or other ventilation parameter data.

The playback of data may proceed at the selected playback speed over the selected time period. Any physiological measurements collected and saved during this time may appear on the playback interface 125 at the times during the selected time period corresponding to the time at which the medical device collected and saved these measurements. In an implementation, the playback interface 125 may display a value for the measurement and then change the value at a time when a new measurement was collected and saved by the medical device. For example, the selected time interval for playback may be one minute. During this minute, the device 110 and/or 150 may have collected physiological measurements once per second (e.g., heart rate, invasive blood pressure, SpO2, etc.). The playback may proceed according to the default or user selected playback speed and for each playback time interval corresponding to one second, the playback interface 125 may display the physiological measurement for that interval and then change the displayed measurement at the next playback time interval corresponding to one second. As another example, the medical device may collect some physiological measurements on demand. For example, a user may request a non-invasive blood pressure measurement at regular or irregular intervals. Each measurement may include a time stamp and the playback interface 125 may display the measurement based on the time stamp. In an implementation, the device 110 and/or 150 may collect numeric values for other available parameters every time the device collects blood pressure and/or another parameter measurement on demand. As a further example, performance data timing may correspond to performance time intervals. For instance, the device 110 and/or 150 may collect chest compression rate and depth data for each chest compression. Thus, the time intervals of the collection may depend on the compression rate. Each item of performance data may include a time stamp and the playback interface 125 may display the measurement based on the time stamp. In an implementation, the device 110 and/or 150 may capture numeric values of all available parameters at a regular time interval (e.g., every 5 seconds, every 10 seconds, every 15 seconds, every 30 seconds, every 60 seconds, etc.). The playback interface 125 may provide these numeric values for every capture time within the playback interval to provide a time trend for these values.

In an implementation, the playback interface 125 may automatically adjust the playback speed based on whether the playback data is current data. For example, during playback of non-current data, the user selected playback speed (e.g., as selected via the playback speed selection bar 538) may determine an actual playback speed implemented by the playback interface 125. In an implementation, the playback pointer 518 may move along the interactive timeline 190 as the data playback proceeds to indicate the time stamp associated with the displayed data. However, for current data, the playback interface 125 may automatically override the user-selected speed and change the playback speed to match the speed at which the operational interface 135 displays the data (e.g., the default or user selected sweep speed).

In an implementation, the playback interface 125 may include a rotary navigation control 560. For example, the rotary navigation control 560 may provide media navigation capabilities similar to those provided by the media navigation bar 191. Further, the rotary navigation control 560 may provide playback loop selection capabilities. The rotary navigation control 560 may be, for example, a jog dial, a jog wheel, a shuttle dial, a shuttle wheel, etc. The rotary navigation control 560 may enable the user to scan through the playback images at the playback interface 125 at various speeds (e.g., a fast shuttle speed or a slow jog speed). In an implementation, the rotary navigation control 560 may be configured to rotate while it is pressed in to a detented stop. Each rotary detent may indicate a request to the playback interface 125 to skip to the next event in the playback data, such as a defibrillation or drug delivery. The rotary navigation control 560 may be in the form of a physical knob that rotates and contains a rotary encoder, or may take the form of a touchscreen emulation of a rotary knob that the user moves with circular finger motion.

In an implementation, the playback interface 125 may provide a volume selection bar 570. The volume selection bar 570 may capture input from the user and, in response to the captured input, the playback interface 125 may adjust an audio playback volume. For example, the user of the playback interface 125 may click on, tap, press, or otherwise provide input to the volume selection bar 570. In an implementation, the playback interface 125 may provide audio data from the medical event simultaneously with or instead of the visual data.

In an implementation, the playback interface 125 may provide a tool function key 580. The user may activate the tool function key 580, for example, via a touchscreen icon, a soft key, and/or other user input device 244. The tool function key 580 may enable a selection of one or more particular types of tools that may include playback time intervals and/or playback speeds. In an implementation, the tool function key 580 may provide selectable options at the interactive menu 550.

Figure 8:
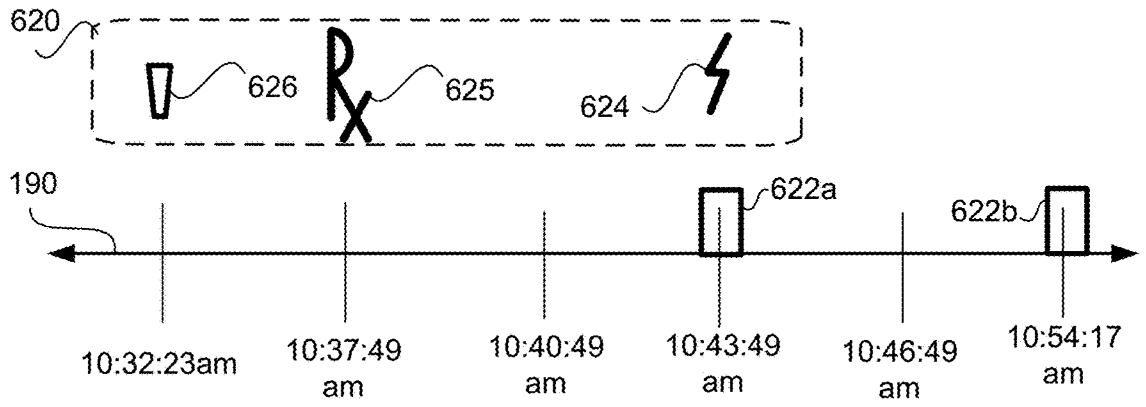
FIG. 8 shows an example of interactive timeline features.

Referring to FIG. 8, examples of visual event indicators for the interactive timeline are shown. The interactive timeline 190 may include visual event indicators 620. In various implementations, the visual event indicators 620 may correspond to medical events and/or device events. The visual event indicators 620 may include graphic icons, textual annotations, or a combination thereof. The visual event indicators 620 may also be referred to as code markers. The medical device 110 may capture code markers and may transmit the code markers to the auxiliary device 150. The patient data received at the auxiliary device 150 and displayed at the playback interface 125 may include the code markers.

For example, the visual event indicators 620 shown in FIG. 8 include a defibrillation indicator 624, a drug administration indicator 625, and a bronchodilator indicator 626. The shape of the icons used for the visual event indicators 620 may be indicative of a type of code marker. For example, the lightning bolt (e.g., indicator 624) may represent shock events and the Rx symbol (e.g., indicator 625) may represent drug administration events. Although an example of one of each type of visual event indicator is shown in FIG. 8 for simplicity, the interactive timeline 190 may include one or more of the various types of the visual event indicators 620. These types of event indicators are examples only and not limiting of the disclosure as the visual event indicators 620 may include other or additional types of event indicators for various medical events.

In an implementation, the medical events represented by the visual event indicators 620 may be delivered therapy events and/or physiological patient events. For example, delivered therapy events may include therapy administered by a person (e.g., manual chest compressions, medications, intubation, ventilation, etc.) and/or therapy administered by a machine (e.g., automated chest compressions, automated drug infusions, electrotherapy, ventilation, etc.). The physiological patient events may be measured events and/or events observed by a caregiver. For example, measured events may include physiological measurements made with a physiological sensor, such as, for example, a pulse oximetry measurement, an ECG, a blood pressure, etc. The observed events may include physiological events that are observed as a result of a caregiver evaluation rather than a sensor measurement. For example, the observed events may include return of spontaneous circulation (ROSC), a coma score, a pain score, difficulty breathing, etc. The caregiver may assign a qualitative value to the observed event but the observed events may not be measurable via the sensor.

In an implementation, the device events represented by the visual event indicators 620 may be a status event and/or operation event of the medical device. For example, the status event may include a low battery, an expired electrode or other consumable, etc. The operation event may include an analyzed heart rhythm, a communication coupling, an electrode attachment, a shock delivery time, a shock duration, a shock energy, etc. Device events may further include, for example, one or more of the occurrence of an alarm (e.g., a monitor-generated alarm such as a heart rate or other arrhythmia alarm), the acquisition of a medical measurement or signal (which may be helpful for documenting at the end of a medical event), and a time at which a "rearrest" soft key was pressed. For example, a user of the medical device may press a "rearrest" soft key at a time at which a renewed or subsequent cardiac arrest condition is observed.

In an implementation, the patient data may include the code markers but may only provide the visual event marker 620 in response to a user request. For example, the user may select a time and/or a time interval on the interactive timeline 190 and playback interface 125 may display the code markers associated with the patient data for the selected time and/or time interval. The playback interface 125 may display the code markers graphically (e.g., on the interactive timeline) and/or as a list that may include the code marker and the time associated with the code marker. As described above, the code markers may include device events. This may provide the advantage of enabling the user of the playback interface 125 to evaluate the patient data in view of particular device conditions existing at the time of patient data collection.

Further examples of data, parameters, and/or events that may correspond or be represented by visual event indicators 620 and/or code markers include one or more clinical events as summarized in Table 3 below. The parameters may include one or more of heart rate, SpO2, pulse rate, EtCO2, non-invasive blood pressure, invasive blood pressure, temperature, change in temperature, blood carbon monoxide level, blood methemoglobin level, total hemoglobin in blood, blood oxygen content, a perfusion index indicative of an arterial pulse signal strength, and a measurement indicative changes in the perfusion index during respiration. The information in Table 3 is an example only and not limiting of the disclosure as other data, parameters, and/or events are within the scope of the disclosure.

TABLE 3

| Category | Sub-Category |
|---|---|
| Foreground analysis | Start shock advisory analysis |
| | Shock advisory result |
| | Individual segment result |
| | Halt shock analysis due to error |
| Defibrillation | Synchronization state |
| | Selected energy |
| | Delivered energy |
| | Device impedance |
| | Patient impedance |
| | Number of shocks |
| CPR | Compression rate |
| | Compression depth |
| Alarms | High parameter alarm |
| | Low parameter Alarm |
| | No breath |
| | Alarm activation |
| | Alarm deactivation |
| | Alarm limit change |
| Life threatening alarms | Asystole |
| | Ventricular fibrillation/tachycardia |
| | Extreme bradycardia |
| | Extreme tachycardia |
| Twelve lead data | ECG data |
| | Analysis result |
| | Patient demographic |
| | Parameter values |
| Treatment markers | System defined |
| | User defined |
| | Drug Delivery |
| | IV |
| | Sedation |
| | CPR |
| | Oxygen delivery |
| | Intubation |
| | Glucose delivery |
| | Fluid delivery |
| Pacer mode | Enter pacer mode |
| | Exit pacer mode |
| | Change pacer rate |
| | Change pacer current |
| Other | Background analysis for advised shock |
| | Change in parameter value |
| | Enter manual mode from AED mode |

As shown above, the treatment markers may include drug delivery. The treatment marker may record the action of delivering the drug along with the name of the drug delivered (e.g., epinephrine, atropine, phenobarbitol, aspirin, morphine, naloxone hydrochloride, diazepam, nitro-glycerin, beta-blockers, Atrovent®, and/or other drugs that provide a rapid response to a code condition). The delivered drugs may include pharmacological treatments for cardiac conditions, respiratory conditions, psychological conditions, allergy, drug overdose, diabetes, fluid control (e.g., a diuretic), pain, etc.

In an implementation, the playback interface 125 may automatically generate the visual event indicators 620. For example, the processor of the device providing the playback interface may generate the visual event indicators 620 in response to machine administered therapy, measured physiological event, and/or device events. In an implementation, the user may request a new visual event indicator 620 via a user input to the playback interface 125. Additionally or alternatively, the user may provide an annotation for the interactive timeline 190 as an event indicator.

In an implementation, the playback interface 125 may include a snap-to-event feature. For example, the user may position the first time selector 622*a* and/or the second time selector 622*b* and provide input to the media navigation bar 191. For instance, the user may press the play control 533 to begin data playback. In response to the input to the media navigation bar 191, the playback interface 125 may move one or more of the first time selector 622*a* and the second time selector 622*b* to a nearest event marker 620. In this way, the playback interface 125 may snap the particular time selector to the event marker. The playback interface 125 may then implement the input to the media navigation bar 191 from the snapped to event marker. For example, if the input is "play" then the playback interface 125 may play the data starting at the snapped to event marker. As another example, if the input is rewind (e.g., control 532 or 531), the playback interface 125 may rewind from the snapped to event marker. In an implementation, if the first time selector 622*a* or the second time selector 622*b* is within a threshold time interval of the current time, the playback interface 125 may snap the particular time selector to the current time and provide real-time playback. The threshold time interval for this snap-to-current feature may be a predetermined time interval such as 1 second, 2 seconds, 3 seconds, 5 seconds, 10 seconds, 15 seconds, 30 seconds, etc. In an implementation, the predetermined time interval may be a user configurable time interval.

In an implementation, the playback interface 125 may enable the user to playback data based on a specific medical condition of the patient. The user may select the medical condition via one or more of the event indicators 620 and/or a medical condition selection control 586. For example, the user may select the event indicator 620 that corresponds to a medical condition of interest to the user with regard to data review. Alternatively or additionally, the user may activate the medical condition selection control 586 via the one or more input device(s) 244 (e.g., a soft key, a tap on a touchscreen icon, a selection of an icon via a cursor, etc.). The medical condition selection control 586 may enable the user to select one or more medical conditions, for example, via the interactive menu 550. The interactive menu 550 may display a list of one or more medical conditions. The one or more medical conditions may be conditions of the patient whose data is under review via the playback interface 125.

Based on the selected medical condition, the playback interface 125 may predetermine various configuration and/or usage settings for data playback and/or display at the playback interface 125. For example, in an implementation, the playback interface 125 may automatically select one or more playback intervals 623 based on the medical condition selected by the user. Additionally or alternatively, the playback interface 125 may select the playback speed, and/or the number of loop repetitions based on the selected medical condition.

For example, the user may select a medical condition of "chest pain" at the interactive menu 550. Additionally or alternatively, the user may select the drug delivery event indicator 625 corresponding to administration of nitroglycerine. The user may select this event based on the knowledge that nitroglycerine may be administered in response to chest pain. In response to either or both of these selections, the playback interface 125 may provide ECG data for a time period spanning the drug administration. Further, the playback interface 125 may automatically select a playback start time at 10 seconds prior to the nitroglycerine delivery event and then set playback for data over a time period of 1 minute, 5 minutes, 10 minutes, 15 minutes, etc. The time period may be preconfigured as a clinically relevant time period based on the selected one or more medical conditions. As another example, if the selected medical condition is difficulty breathing, the playback interface may select a start point that coincides with an event indicator for delivery of bronchodilator.

Figure 9:
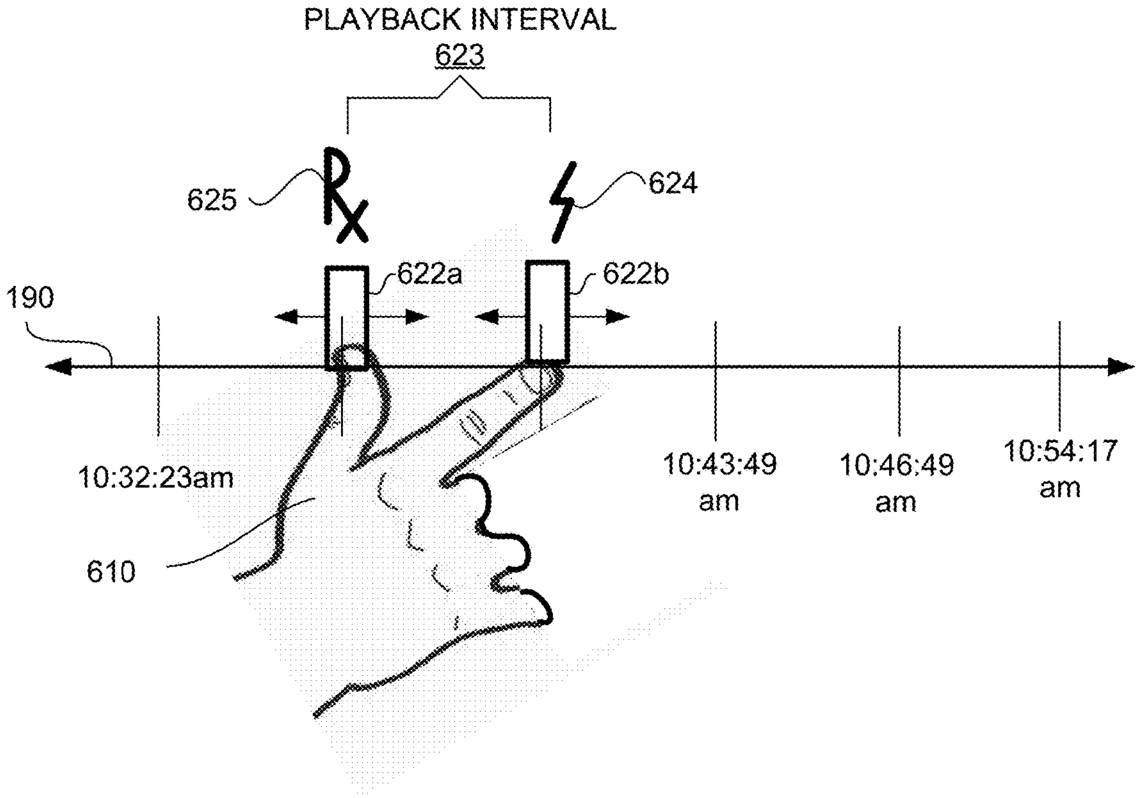
FIG. 9 shows an example of touchscreen control of the playback interface.

Referring to FIG. 9, an example of touchscreen control of the playback interface is shown. In an implementation, the playback interface 125 may capture a touchscreen gesture 610 to determine the playback interval 623. As an example, the interactive timeline 190 may recognize as input the two times indicated by each finger of the caliper gesture and set these times as the boundaries of the playback interval 623. As another example, the user may use the touchscreen gesture 610 to drag or slide the time selectors 622*a* and 622*b* along the interactive timeline 190. In an implementation, the time selectors 622*a* and 622*b* and/or other features on the playback interface 125 may capture input via a push gesture that exerts sufficient pressure on the display screen 115*b* to interpret the input as a push gesture.

In an implementation, the playback interface 125 may provide looped playback of the patient data over the playback interval 623. For example, the looped playback may improve recognition by the user of the playback interface 125 of changes in ECG morphology due to delivery of nitroglycerin or changes in EtCO2 as a result of delivery of a bronchodilator. Thus, the playback interface 125 may provide the patient data from the start time of the playback interval 623 to the stop time of the playback interval 623 and then repeat this playback at the start time of the playback interval 623 to provide the data loop. The playback loop may repetitively playback the data over the playback interval 623. In an implementation, the playback interface 125 may include a loop control 540 (e.g., as shown in FIG. 7) that may control the loop playback (e.g., start the playback, stop the playback, capture input indicating a number of repetitions, etc.). The playback loop may be played back at an adjustable speed and loop interval duration.

In an implementation, the user may select one or more visual event indicators 620 to set the playback interval 623. For example, the playback interval 623 may be associated with a first selected visual event indicator (e.g., the indicator 625) and a second selected visual event indicator (e.g., the indicator 624). Thus, the playback interface 125 may be configured to playback patient data corresponding to the intervening time between the two selected indicators. In the example of FIG. 9, the playback interface 125 may playback data collected by the medical device 110 between delivery of a drug and a subsequent defibrillation. For example, if the patient is experiencing chest pain, the first visual event indicator selected may be a code marker for delivery of nitroglycerine.

In an implementation, the playback interval 623 may include a time interval prior to and/or subsequent to the time associated with the visual event indicator 620 and/or a code marker. For example, the playback time interval may specify that the playback of data associated with the selected visual event indicator 620 begin with data associated with a time such as 1 second, 2 seconds, 5 seconds, 10 seconds, 15 seconds, 30 seconds, 60 seconds or another suitable time interval prior to the time stamp of the selected visual event indicator 620. In this way, the user of the playback interface 125 may review and/or analyze medical data leading up to the event associated with the selected visual event indicator 620. Similarly, the playback time interval may specify that the playback of data associated with the selected visual event indicator 620 end with data associated with a time, for example, of 1 second, 2 seconds, 5 seconds, 10 seconds, 15 seconds, 30 seconds, 60 seconds, 2 minutes, or another time interval after the time stamp of the selected visual event indicator 620. In this way, the user of the playback interface 125 may review and/or analyze medical data subsequent to the selected visual event indicator 620.

Selection (e.g., by tapping, clicking, pressing, and/or another method of providing input to the playback interface 125) of a visual event indicator 620 may also result in specific information relevant to that visual event indicator 620 appearing in the data display window 510. For instance, if the drug administration icon 625 is associated with an intervention using a bronchodilator then the data provided in the data display window 510 might be the EtCO2 waveform, heart rate, spirometric data, and/or other ventilator flow parameters and waveforms. This data may provide an indication of whether or not the intervention has improved the patient condition. As another example, selection of the drug administration event indicator 625 may initiate playback of relevant parameters such as capnography or airway flow data (e.g., spirometry data). The playback may enable an evaluation of a patient response to an administration of nitroglycerine, a bronchodilator, and/or adrenaline, for instance. As further example, a selection of the shock visual event indicator 624 may initiate playback of ECG waveform data corresponding to the selected shock.

Figure 10A:
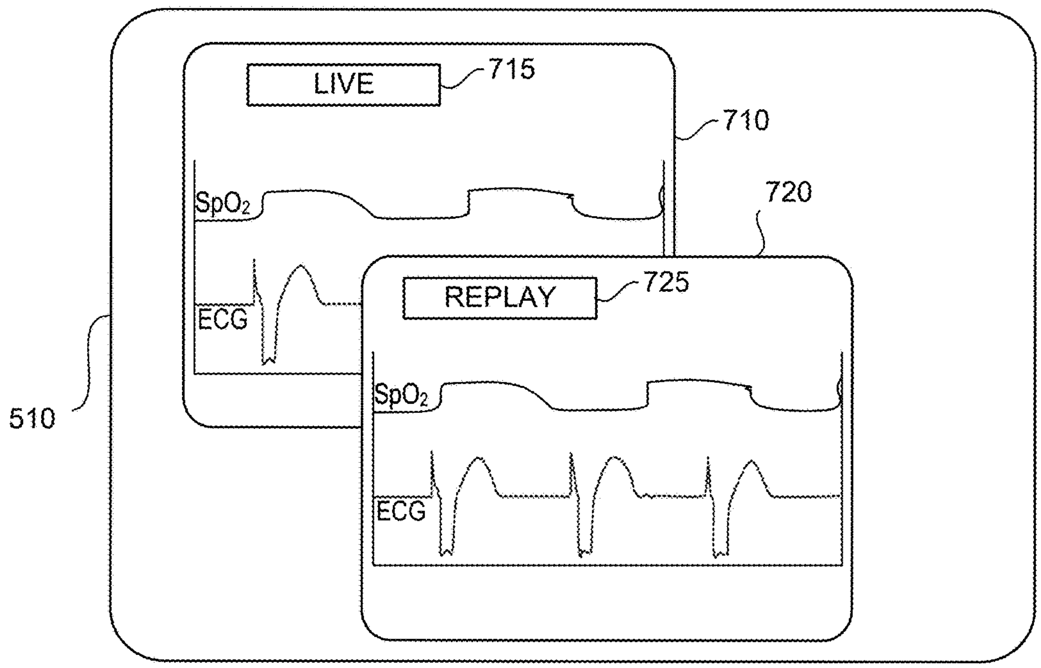
FIGS. 10A-10B show examples of multiple temporal windows on the playback interface.
Figure 10B:
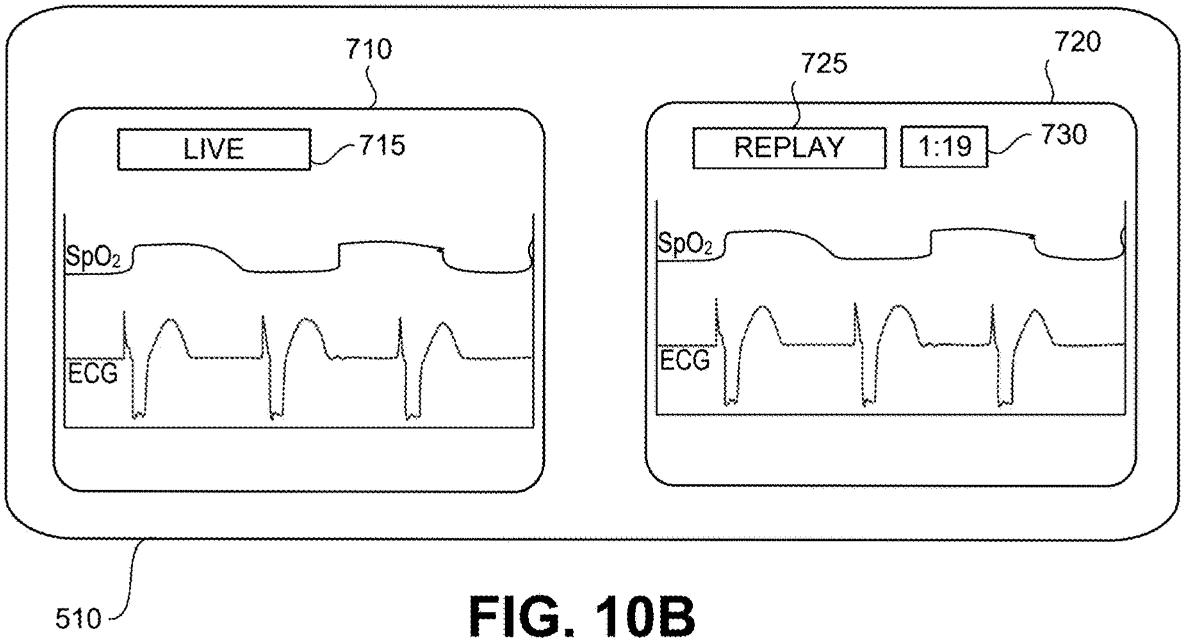

Referring to FIGS. 10A and 10B, with further reference to FIG. 7, examples of multiple temporal windows on the playback interface is shown. In an implementation, the data display window 510 may provide the multiple temporal windows. The multiple temporal windows may include one or more real-time windows 710 (e.g., the “LIVE” window as indicated by the temporal status field 715) and one or more historical windows 720 (e.g., the “REPLAY” window as indicated by the temporal status field 725). The real-time windows 710 may include patient data that includes transmission delays but does not include historic patient data based on the user selection of data not currently available at the operational interface. The real-time windows 710 may include indicators of transmission delays as discussed with regard to FIG. 5.

The multiple temporal windows may be displayed with overlap as shown, for example, in FIG. 10A or without overlap as shown, for example, in FIG. 10B. In various implementation, the multiple temporal windows may include a combination of real-time and historical windows, all historical windows, or all real-time windows. Multiple real-time windows may include different real-time data and/or different visual representations of the real-time patient data. In an implementation, the “REPLAY” window may include a time delay indicator 730 that displays a time span (e.g., an amount of time) between the displayed data and the current clock time at the auxiliary device. The time delay indicator 730 may indicate the historic point in time selected by the user.

Figure 11:
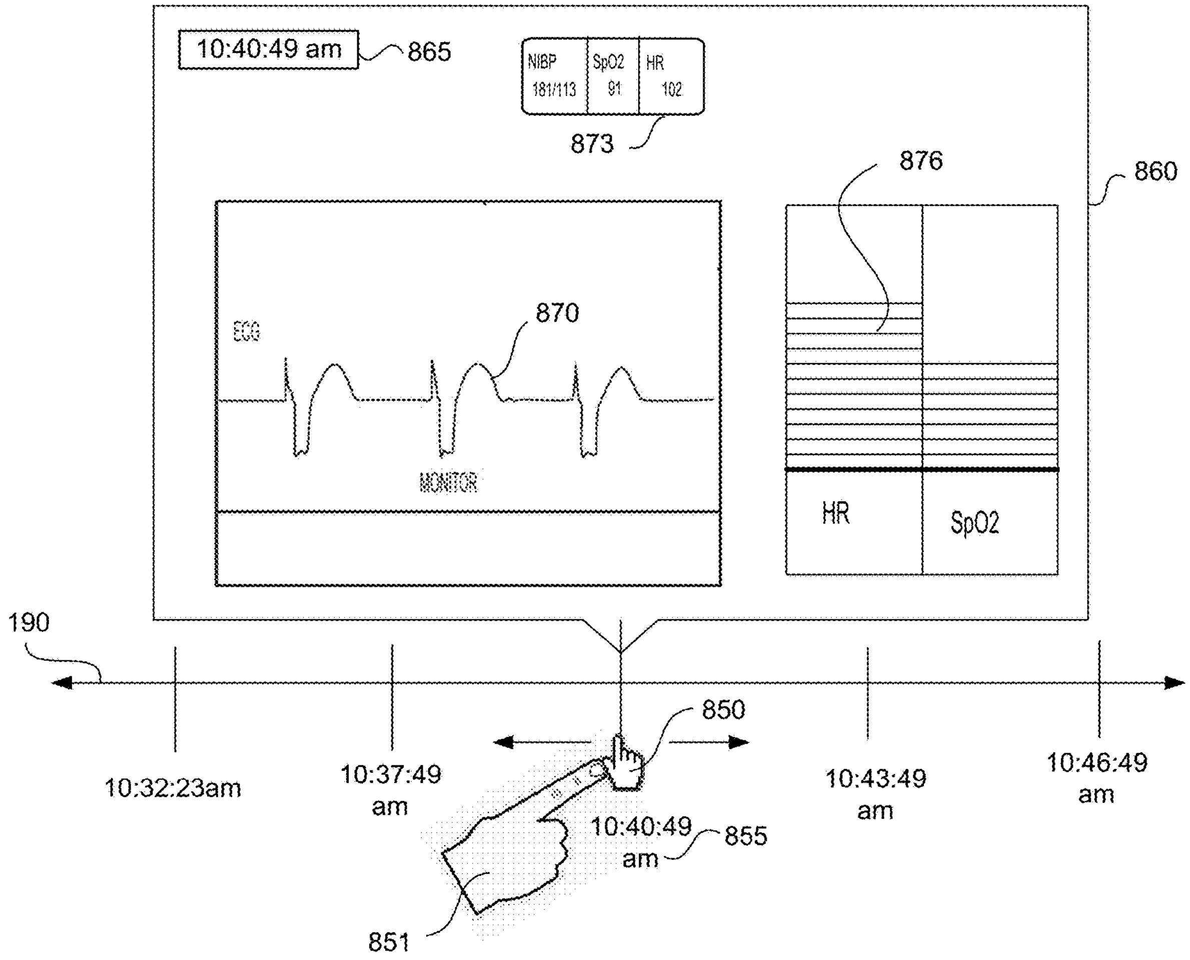
FIG. 11 shows an example of an on-screen cursor for the interactive timeline.

Referring to FIG. 11, with further reference to FIG. 7, an example of an on-screen cursor for the interactive timeline is shown. In an implementation, the interactive timeline 190 may include an on-screen cursor 850. For example, the on-screen cursor 850 may take the form of a hand with a pointed finger. However, this form is an example only and other cursor icons and/or representations are within the scope of the disclosure. The user of the playback interface 125 may provide input (e.g., via the one or more input device(s) 244 shown in FIG. 14) and this input may determine a position of the on-screen cursor 850 along the interactive timeline 190.

In an implementation, the display that provides the playback interface 125 may be a touchscreen. The user may place his or her finger 851 on the on-screen cursor 850 and move the on-screen cursor 850 along the touchscreen in response to a movement of the user’s finger 851 along the touchscreen. With this or another touchscreen gesture, the user may position the on-screen cursor 850 at a particular timeline position (e.g., a user-selected position) in order to select the time associated with this position as the time for patient data playback. In various implementations, the user of the playback interface 125 may click, double click, tap, double tap, and/or provide another input to the interactive timeline 190 to activate the on-screen cursor 850. Though, it can be appreciated that for certain embodiments such as where the playback interface 125 is a touchscreen, an on-screen cursor is not a required element.

In an implementation, the user may provide an input (e.g., a touchscreen gesture such as a press or tap on the on-screen cursor 850) to activate a preview pop-up window 860. The preview pop-up window 860 may provide a visual representation of the patient data that includes sufficient detail for the user to determine whether to select a time period for playback that includes the particular timeline location corresponding to the pop-up window. For example, the ECG displayed in the pop-up window may exhibit features representative of bradycardia or another relatively easily observable ECG feature. In response to viewing this ECG feature, the user may decide to view discrete physiological values over this time period, for example the EtCO2 values to try to determine the cause of and/or effective medical interventions for the condition represented in the ECG.

In some implementations, the playback interface 125 displays the preview pop-up window 860 above or to the side of a location or area on the touchscreen corresponding to a location of one or more of the user’s digits (e.g., thumb, fingers). The touchscreen is configured to recognize the location of the one or more of the user’s digits. In this manner, the information provided in the preview pop-up window 860 may be unobstructed by the user’s digits. Additionally or alternatively, in an implementation, the preview pop-up window 860 may be located proximate to the on-screen cursor 850 and/or the interactive timeline 190. The playback interface 125 may approximately vertically align the preview pop-up window 860 with the playback pointer 518. In some implementations, the on-screen cursor 850 may replace the playback pointer 518, or vice-versa. The information displayed in the preview pop-up window 860 may include patient data and/or device state information that corresponds to the time indicia of the playback pointer 518 and/or the on-screen cursor 850.

In an implementation, the user of the playback interface 125 may slide the on-screen cursor 850 along the interactive timeline 190 to determine and change the contents of the preview pop-up window 860. In some implementations, if the display 115*b* is the pressure sensitive touchscreen, then in response to a pressure on the screen in excess of a pressure threshold (e.g., a pressure in excess of approximately 0.2-0.3 lbs.), the playback interface 125 may increase a size of the preview pop-up window 860 (e.g., increase an area of the display screen 115*b* occupied by the preview pop-up window 860). In some implementations, the size of the preview pop-up window 860 may be proportional to the amount of force in an approximately linear fashion. In various implementations, the pressure threshold may be 0.5 pounds, 1 pound, 2 pounds, 3 pounds, 4 pounds, or 5 pounds of force. In some implementations, there may be multiple thresholds that cause enlargement of the preview pop-up window 860 to increase in size in a step-wise fashion in response to an increase in pressure on the touchscreen. For example, as the pressure on the touchscreen increases and exceeds additional thresholds of the multiple thresholds, the size of the preview pop-up window 860 may increase relative to a previous size.

In some implementations, the preview pop-up window 860 may be too small to adequately display all of the patient data corresponding to the time indicia of the playback pointer 518 or on-screen cursor 850. In such cases, the playback interface 125 may prioritize the patient data according to predetermined criteria. The playback interface 125 may display the patient data at the pop-up window 860 according to the determined priority and a current size of the preview pop-up window 860. For example, the playback interface 125 may display a single data element with the highest priority if there is only space to display the single data element in the preview pop-up window 860. With progressively larger preview pop-up windows 860, the playback interface 125 may display additional data elements in order of their predetermined priority. For instance, heart rate information may have the highest priority, SpO2 next higher, followed by, in order, EtCO2, EGC waveform, pulse oximetry waveform. In some implementations, the priority order may be a default priority for the playback interface 125. In some implementations, the playback interface 125 may automatically modify the priority order from the default order and/or capture user input to modify the priority order from the default order. The priority order may depend on the state of the medical device 110. For example, if the medical device 110 is in a defibrillation mode (e.g., the defibrillation electrodes are attached to the patient, an ECG analysis is underway, a device log indicates a recent electrotherapy delivery, etc.), then the playback interface 125 may change the second priority data element from SpO2 to EtCO2. As described below, the playback interface 125 may enable the user to play back data based on a specific medical condition of the patient. The user may select the medical condition via one or more of the event indicators 620 and/or a medical condition selection control 586. For instance, if the user selects myocardial infarction (heart attack), the priority may be adjusted to have ST segment elevation be the highest priority, followed by ECG waveform, followed by heart rate.

In some implementations, the playback interface 125 may adjust the information displayed in the preview pop-up window 860 if the playback pointer 518 and/or the on-screen cursor 850 are co-located with a visual event indicator 620. This situation may indicate that the patient data in the preview pop-up window 860 corresponds to the time of the visual event indicator. For instance, the visual event indicator 620 may be a lightning bolt (e.g., indicator 624) that represents defibrillation shock event, in which case the priority and information display formatting may be adjusted to present the information most relevant and in an optimal fashion relative to the specific defibrillation event; for instance, the information displayed may be 6 seconds of ECG prior to the defibrillation shock, 9 seconds of ECG after the shock, the results of the defibrillation analysis pre-shock (e.g. either "Shock" or "No-Shock Advised"), 6 seconds of additional ECG along with ECG heart rate and pulse oximetry heart rate after some period of delay post-shock (e.g. 5 seconds, 10 seconds, 30 seconds) in order to assess whether return of spontaneous circulation was achieved. If the visual event indicator 620 is the Rx symbol (e.g., indicator 625) representing a drug administration event, for instance delivery of an asthma inhaler, the highest priority data element may be breath tidal volume, followed by other respiratory diagnostic information like capnographic information or spirometric data.

In some implementations, narrow regions around the visual event indicators have a so-called "magnetic" feature. The magnetic feature causes the on-screen cursor 850 to be attracted to the timeline location of the particular visual event indicator 620 to which the on-screen cursor 850 is adjacent within less than a predetermined distance. The predetermined distance may be measured in terms of time (e.g. less than 30 seconds, less than 1 minute, etc.) or screen distance (e.g. less than 0.05 inch, less than 0.1 inch, less than 0.25 inch). When the on-screen cursor 850 is less than the predetermined distance from the visual event indicator 620, what is displayed on the preview pop-up window 860 is the information from the time at the visual event indicator 620. In some implementations, the magnetic feature may also include causing the on-screen cursor 850 to jump spatially so that it is vertically aligned with the visual event indicator 620. In some implementations, when the magnetic feature occurs and the information from the time of the visual event indicator 620 is displayed in the preview pop-up indicator, it may further cause the preview pop-up window to increase in size so that more data may be easily and cogently be displayed.

For example, the patient data may include a physiologic waveform 870. In various implementations, the preview pop-up window 860 may provide the patient data in a text and/or numeric format 873 and/or in a non-numeric graphical format 876 (e.g., a bar graph, a fillable shape, an icon, an arrow, etc.). The patient data display in the preview pop-up window 860 may correspond to the time 855 (e.g., 10:40:49 am) associated with the position of the on-screen cursor 850. In an implementation, the preview pop-up window 860 may include a window time indicator 865 that indicates the position of the cursor 850 along the interactive timeline 190.

Figure 12:
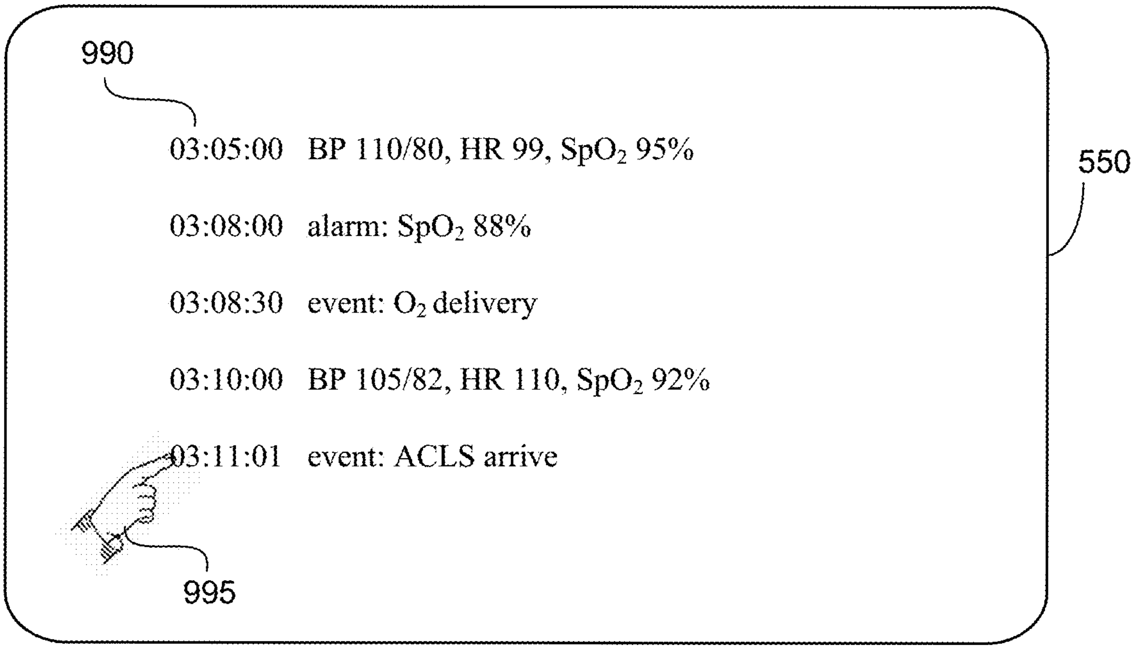
FIG. 12 shows an example of an event search function for the playback interface.

Referring to FIG. 12 with further reference to FIG. 7, an example of an event search function for the playback interface is shown. In an implementation, the playback interface 125 may provide an event search function 583. The user may activate the event search function 583, for example, via the one or more input device(s) 244 (e.g., a soft key, a tap on a touchscreen icon, a selection of an icon via a cursor, etc.).

In an implementation, activation of the event search function 583 may open the interactive menu 550. The interactive menu 550 may include a text list 990 of events and/or interventions and may include one or more code markers. The list 990 may be a user-selectable list. In this example, the list 990 includes time stamped data for blood pressure (BP), heart rate (HR), oxygen saturation ($SpO_2$), delivery of oxygen ($O_2$), and arrival of advanced cardiac life support (ACLS) equipment and/or personnel. The user may select an event from the list 990 to initiate playback of event data. For example, the user of the playback interface 125 may select an event via a touch gesture or a mouse or other input device (e.g., input device(s) 244). Via the user input, the user may adjust a position of a selection cursor 995 to select the event. In response, the playback interface 125 may provide playback of data collected by the medical device 110 at the time of the selected event indicator (e.g., the event "ACLS arrive" at 03:11:01 is shown as selected in FIG. 12 based on the position of the selection cursor 995). In an implementation, the text list 990 may be a sorted list according to chronological order.

The event search function 583 may be a search/sort function and may sort the visual event indicators 620 or code markers by types of events and interventions, for instance, defibrillation shock, drug administration, intubation, fluid delivery, chest compression protocol, or ventilation protocol. The events may also be sorted into diagnostic events and therapy events. For example, therapy events may include defibrillation, pacing, drug delivery, etc. Diagnostic events may include detection of ventricular fibrillation, COPD, asthma, etc.

In an implementation, activation of the event search function 583 may enable a user selection of one or more particular types of the visual event indicator 620 and/or code markers (e.g., shock events, drug events, etc.). For example, in response to the selection of an event, the event search function 583 may highlight events on the interactive menu 550 that correspond to the selected type of code marker. In an implementation, the event search function 583 may highlight the visual event indicators 620 on the interactive timeline 190 that correspond to the selected type of code marker. The user may select one or more of the visual event indicators 620 on the interactive timeline 190 to receive more information about the event indicated by the visual event indicator.

Figure 13A:
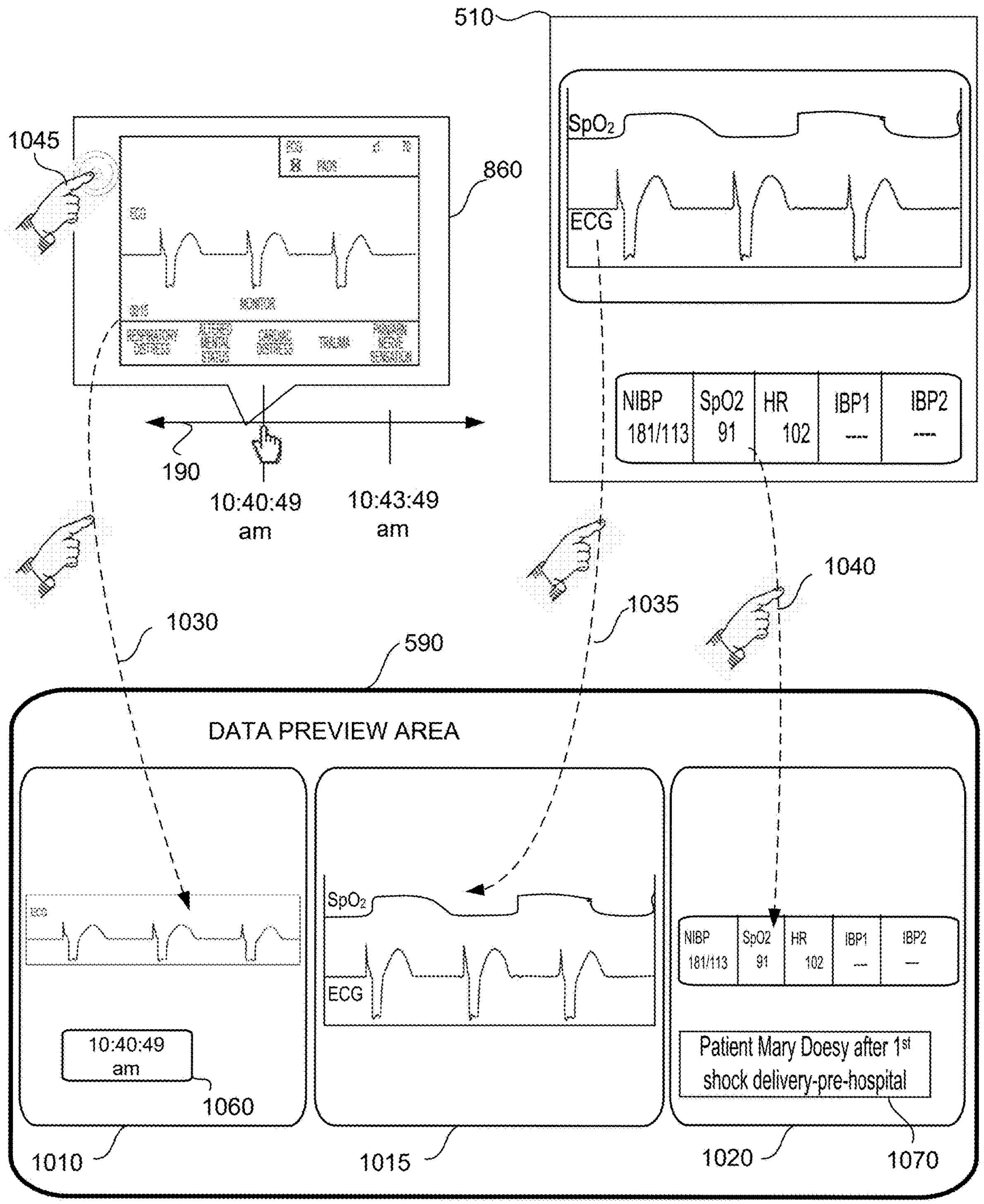
FIG. 13A shows an example of a data preview area for the playback interface.

Referring to FIG. 13A, with further reference to FIG. 7, an example of a data preview area for the playback interface is shown. In an implementation, the playback interface 125 may provide the data preview area 590. The data preview area 590 may include one or more data preview windows, e.g., data preview windows 1010, 1015, and 1020. In an implementation, the user of the playback interface 125 may drag and drop displayed information from the data display window 510 and/or from the preview pop-up window 860 to the data preview area 590. For example, the user may implement one of the drag and drop touchscreen gestures represented schematically in FIG. 13A as the arrows 1030, 1035, and 1040. In an implementation, the user may implement a tap and/or a push (e.g., the push gesture 1045) to exert pressure on a particular data image, and cause the playback interface 125 to add the particular data image to the data preview area 590. In a further implementation, the user may add data to the data preview area 590 via a pointing device such as a mouse and/or a cursor. For example, the user may click/double click on a selected data image and either drag the selected data image to the data preview area 590 or employ a second click to move the selected data image to the data preview area 590.

In an implementation, the data preview windows 1010, 1015, and 1020 may provide data in various formats. For example, one or more of the data preview windows may provide the data in a time trend format, waveform format, text format, numeric format, and/or non-numeric graphical format.

In an implementation, one or more of the data preview windows 1010, 1015, and 1020 may include a time display 1060. The time display 1060 may be the time on the interactive timeline 190 that is associated with the data image in the respective data preview window 1010, 1015, or 1020. In an implementation, the playback interface 125 may automatically display the data images within the data preview area 590 in chronological order. For example, as a data image is added to a data preview window 1010, 1015, and/or 1020, the playback interface 125 may rearrange the data preview windows 1010, 1015, and 1020 such that the windows display the data images in chronological order from right to left or from left to right within the data preview area 590.

In an implementation, the playback interface 125 may prompt the user to enter an annotation 1070 specific to the data image when it has been dragged to the data preview area 590. For example, the annotation may include caregiver notes, observations, instructions, etc. The playback interface 125 may capture the annotation 1070 as a text input, for instance via a keyboard and/or via an audio input, for instance, via a microphone. The playback interface 125 may associate the audio recording with the particular data represented by the data image. In addition, the playback interface 125 may implement voice recognition software to convert the audio recording into text.

In an implementation, the user may select one of the data preview windows 1010, 1015, or 1020 for data playback. The data display window 510 may playback the data from the selected data preview window 1010, 1015, or 1020. For example, the user may initiate playback by pressing on the selected data preview window, clicking a mouse controlling a cursor on the selected data preview window, or otherwise providing user input, via the touchscreen or other user input device, indicative of the selected data preview window. The processor 120 may control the playback interface 125 to begin playback of the data in the selected data preview window at the time indicated by the time display 1060 or alternatively at a time that is a preconfigured interval (e.g., 1 second, 5 seconds, 10 seconds, 15 seconds, 30 seconds, 60 seconds, 120 seconds, 180 seconds, etc.) before the time indicated by the time display 1060.

Figure 13B:
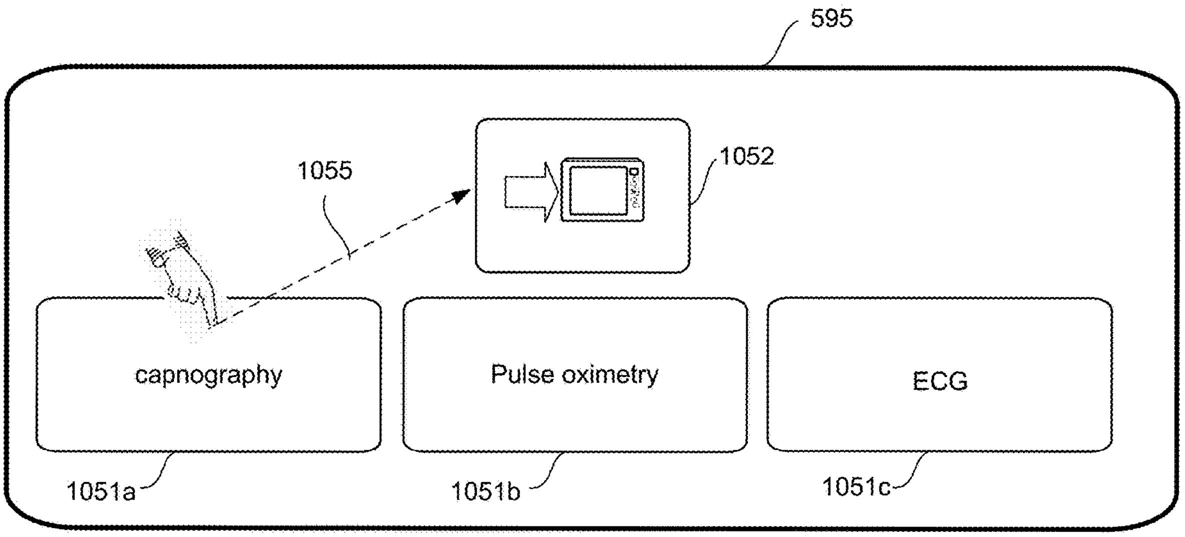
FIG. 13B shows a schematic example of selecting a data type via a touchscreen gesture.
Figure 13C:
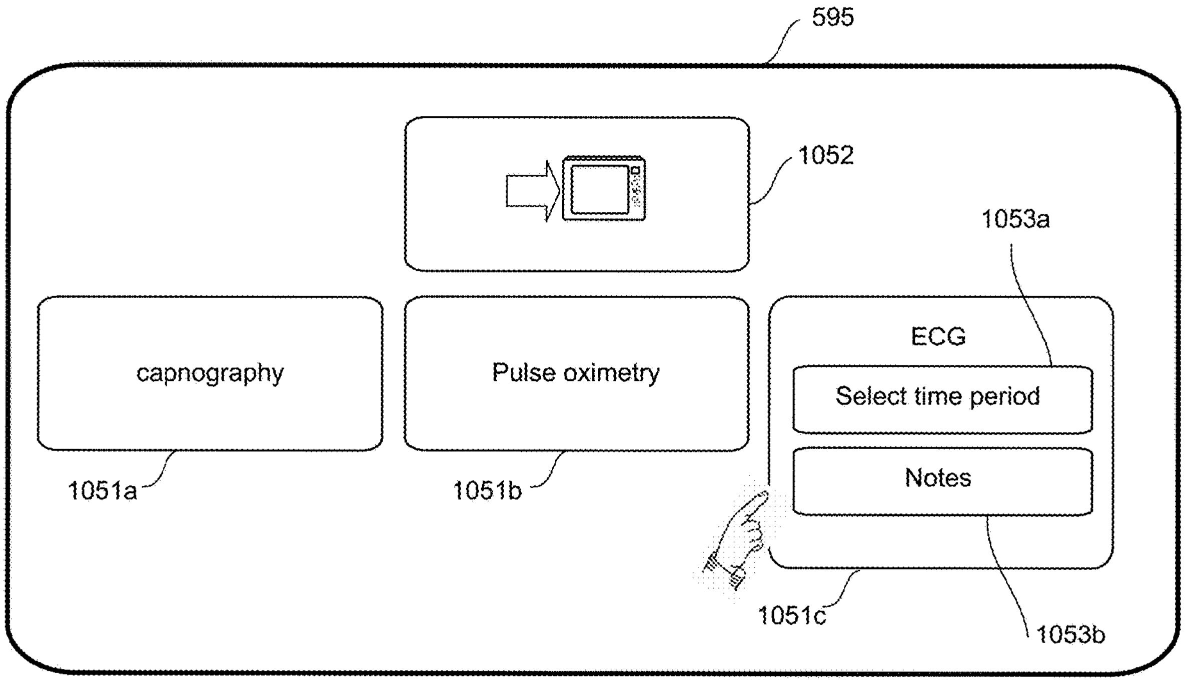
FIG. 13C shows a schematic example of opening a data attribute window via a tap on a data type icon.

Referring to FIGS. 13B and 13C, with further reference to FIG. 7, examples of a data selection area for user selection of data to display on a communicatively coupled device are shown. In an implementation, the playback interface 125 may include the data selection area 595. The data selection area 595 may include one or more data type icons (e.g., the icons 1051*a*, 1051*b*, and 1051*c*) where data type icon corresponds to a particular data type (e.g., capnography, pulse oximetry, ECG, etc.). The icons may be textual, graphic, or a combination thereof. The data selection area 595 may further include one or more target device icons 1052. Each of the target device icon(s) 1052 may represent a communicatively coupled device. For example, if the data selection area 595 is at the playback interface 125 of the auxiliary device 150, the communicatively coupled device may be the medical device 110. In this scenario, for example, the auxiliary device 150 may capture the user selection of data to display at the medical device 110. The auxiliary device 150 may provide this selection as an instruction to the medical device 110 via the communicative coupling 399. The medical device 110 may receive this instruction and control its display screen 115*a* to display the data selected by the user at the auxiliary device 150.

In an implementation, as shown for example in FIG. 13B, the user of the playback interface 125 may select a data type via a touchscreen gesture. For example, the user may perform a drag and drop gesture 1055 to drag the selected data type (e.g., capnography 1051*a*) to the target device icon 1052. In response to this gesture, the processor controlling the playback interface 125 may send an instruction indicative of the selected data type to the communicatively coupled device.

In an implementation, as shown for example in FIG. 13C, the user of the playback interface 125 may tap on a data type icon (e.g., the ECG icon 1051*c*) to open one or more data attribute windows (e.g., the windows 1053*a* and 1053*b*). For example, the data attribute windows may enable the user to select a time period for the data display instruction (e.g., using the time period selection window 1053*a*) and/or include notes for the user of the communicatively coupled device (e.g., using the notes window 1053*b*). Alternatively or additionally, the user may provide data display instructions for the communicatively coupled device via the interactive menu 550 shown in FIG. 7.

In an implementation, it may be beneficial for the user of the auxiliary device to determine and/or modify information provided at the medical device. For example, based on data review at the playback interface 125, the user 102*b* may provide user input at the auxiliary device 150 that causes the medical device 110 to provide particular information for the user 102*a*. The auxiliary device 150 may capture the user input at the playback interface 125 and send the user input to the medical device 110 via the communicative coupling 399. The medical device 110 may receive the user input and provide information at the display screen 115*a* based on the received user input. In various implementations, the user input may include an instruction to automatically display selected patient data and/or may include an instruction to provide the user input as user feedback.

As an example, the user 102*b* of the auxiliary device 150 may review the patient data collected by the medical device 110 at the playback interface 125. The patient data may include a capnography waveform, a pulse oximetry waveform, and an ECG. The user 102*b* may evaluate the patient data and determine that the caregiver 102*a* should view the capnography waveform in order to adjust ventilation provided to the patient. The user 102*b* may provide user input to the playback interface 125 that generates an instruction for the medical device 110 to display the capnography waveform. In response to receipt of this instruction, the medical device 110 may automatically display the capnography waveform. Alternatively, in response to receipt of this instruction, the medical device 110 may prompt the user 102*a* to select the capnography waveform for display.

In an implementation, the user feedback may include one or more visible and/or audible instructions provided at the operational and/or the playback interface. For example, the visible instructions may include text instructions, graphic instructions, animated instructions, video instructions, a live video stream, a pre-recorded video, a written and/or video chat, etc. As additional or alternative examples, the visible instructions may include data annotations and/or other display changes to the playback interface features. For example, display changes may include color and/or font changes, additional event markers, flashing event markers and/or data, highlighted time intervals for displayed data (e.g., color indications of times on the timeline and/or color changes to selected data portions corresponding to particular time ranges), hidden data and/or hidden portions of data, etc. As further examples, the audible instructions may include live audio stream, pre-recorded audio, audio-video instructions (e.g., live and/or pre-recorded), an audio chat, a live communication with the user of the auxiliary device 150 (e.g., a cellular, Internet, and/or other network based audio call), an alarm, a tone or other noise emitted from the first medical device, etc. In an implementation, the medical device 110 may provide a user selectable icon to enable the provision of instructions from the user 102*b* of the auxiliary device. For example, an icon may read "press to play instructions" and in response to user pressure on the icon, the first medical device 110 may provide the instructions.

Referring to FIG. 14, examples of components of the medical device 110 and the auxiliary device 150 are shown schematically. The medical device 110 may include at least one processor 120 (e.g., a second processor), at least one memory 121 (e.g., a second memory), one or more output devices 130 (e.g., second output devices), one or more user input devices 144 (e.g., second input devices), and at least one communication interface 145 (e.g., a second communication interface). The auxiliary device 150 may include at least one processor 220 (e.g., a first processor), at least one memory 221 (e.g., a first memory), one or more output devices 230 (e.g., first output devices), one or more user input devices 244 (e.g., first input devices), and at least one communication interface 245 (e.g., a first communication interface).

In various implementations, the medical device 110 may be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 110 may be an integrated therapy delivery/monitoring device within a single housing (e.g., the single housing 1140, as shown in FIG. 14). The single housing 1140 may surround, at least in part, the therapy delivery components and the monitoring components. In an implementation, the medical device 110 may be a modular therapy delivery/monitoring device, for example the device 410 as described in further detail below with regard to FIG. 15.

The patient interface device(s) 160 may include one or more therapy delivery component(s) 161*a* and/or one or more sensor device(s) 161*b*. The patient interface device(s) 160 are described with regard to FIG. 1A and also described below with regard to FIG. 14.

The medical device 110 may be configured to couple to the one or more therapy delivery component(s) 161*a*. In combination, the medical device 110 and the one or more therapy delivery components may provide therapeutic treatment to the patient 101. In an implementation, the medical device 110 may include or incorporate the therapy delivery component(s) 161*a*. The therapy delivery component(s) 161*a* are configured to deliver therapy to the patient and may be configured to couple to the patient. For example, the therapy delivery component(s) 161*a* may include one or more of electrotherapy electrodes including defibrillation electrodes and/or pacing electrodes, chest compression devices (e.g., one or more belts or a piston), ventilation devices (e.g., a mask and/or tubes), drug delivery devices, etc. The medical device 110 may include the one or more therapy delivery component (s) 161*a* and/or may be configured to couple to the one or more therapy delivery component(s) 161*a* in order to provide medical therapy to the patient. The therapy delivery component(s) 161*a* may be configured to couple to the patient 101. For example, the caregiver 102*a* may attach the electrodes to the patient and the medical device 110 (e.g., a defibrillator or defibrillator/patient monitor) may provide electrotherapy to the patient 101 via the defibrillation electrodes. These examples are not limiting of the disclosure as other types of medical devices, therapy delivery components, sensors, and therapy are within the scope of the disclosure.

The first medical device 110 may be, for example, a therapeutic medical device capable of delivering a medical therapy. For example, the medical therapy may be electrical therapy (e.g. defibrillation, cardiac pacing, synchronized cardioversion, diaphragmatic or phrenic nerve stimulation) and the first medical device 110 may be a defibrillator, a defibrillator/monitor, a mechanical ventilator such as the ZOLL Z-Vent, and/or another medical device configured to provide electrotherapy. As another example, the medical therapy may be chest compression therapy for treatment of cardiac arrest and the first medical device 110 may be a mechanical chest compression device such as a belt-based chest compression device or a piston-based chest compression device. As other examples, the medical therapy may be ventilation therapy, therapeutic cooling or other temperature management, invasive hemodynamic support therapy (e.g. Extracorporeal Membrane Oxygenation (ECMO)), etc. and the medical device 110 may be a device configured to provide a respective therapy. In an implementation, the medical device 110 may be a combination of one or more of these examples. The therapeutic medical device may include patient monitoring capabilities via one or more sensors. These types of medical therapy and devices are examples only and not limiting of the disclosure.

The medical device 110 may include, incorporate, and/or be configured to couple to the one or more sensor(s) 161*b* which may be configured to couple to the patient 101. The sensor(s) 161*b* are configured to provide signals indicative of sensor data (e.g., first sensor data) to the medical device 110. The sensor(s) 161*b* may be configured to couple to the patient. For example, the sensor(s) 161*b* may include cardiac sensing electrodes, a chest compression sensor, and/or ventilation sensors. The one or more sensors 161*b* may generate signals indicative of physiological parameters of the patient 101. For example, the physiological parameters may include one or more of at least one vital sign, an ECG, blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, physical parameters as determined via ultrasound images, parameters determined via near-infrared reflectance spectroscopy, pneumography, and/or cardiography, etc. The ultrasound images may include ultrasound images of a patient's heart, carotid artery, and/or other components of the cardiovascular system. Additionally or alternatively the one or more sensors 161*b* may generate signals indicative of chest compression parameters, ventilation parameters, drug delivery parameters, fluid delivery parameters, etc.

In addition to delivering therapy to the patient, the therapy delivery component(s) 161*a* may include, be coupled to, and/or function as sensors and provide signals indicative of sensor data (e.g., second sensor data) to the medical device 110. For example, the defibrillation electrodes may be configured as cardiac sensing electrodes as well as electrotherapy delivery devices and may provide signals indicative of transthoracic impedance, electrocardiogram (ECG), heart rate and/or other physiological parameters. As another example, a therapeutic cooling device may be an intravenous cooling device. Such a cooling device may include an intravenous (IV) device as a therapy delivery component configured to deliver cooling therapy and sense the patient's temperature. For example, the IV device may be a catheter that includes saline balloons configured to adjust the patient's temperature via circulation of temperature controlled saline solution. In addition, the catheter may include a temperature probe configured to sense the patient's temperature. As a further example, an IV device may provide therapy via drug delivery and/or fluid management. The IV device may also monitor and/or enable monitoring of a patient via blood sampling and/or venous pressure monitoring (e.g., central venous pressure (CVP) monitoring).

The medical device 110 may be configured to receive the sensor signals (e.g., from the therapy delivery component(s) 161*a* and/or the sensor(s) 161*b*) and to process the sensor signals to determine and collect the patient data. The patient data may include patient data which may characterize a status and/or condition of the patient (e.g., physiological data such as ECG, heart rate, respiration rate, temperature, pulse oximetry, non-invasive hemoglobin parameters, capnography, oxygen saturation (SpO2), end tidal carbon dioxide (EtCO2), invasive blood pressure (IBP), non-invasive blood pressures (NIBP), tissue pH, tissue oxygenation, Near Infrared Spectroscopy (NIRS) measurements, etc.). Additionally or alternatively, the patient data may characterize the delivery of therapy (e.g., chest compression data such as compression depth, compression rate, etc.) and/or the patient data may characterize a status and/or condition of the medical equipment used to treat the patient (e.g., device data such as shock time, shock duration, attachment of electrodes, power-on, etc.).

The auxiliary device 150 may incorporate and/or be configured to couple to one or more patient interface device(s) 260. The patient interface device(s) 260 may include one or more therapy delivery components 261*a* and one or more sensors 261*b*. The therapy delivery component(s) 261*a* may be substantially as described herein with regard to the therapy delivery component(s) 161*a*. Similarly, the sensor(s) 261*b* may be substantially as described herein with regard to the sensor(s) 161*b*.

Similarly, a processor of the auxiliary device (e.g., the processor 220 shown in FIG. 14) may determine and/or generate the patient data (e.g., second patient data) based on the signals from the patient interface devices 260. The processor of the first medical device 110 and/or the processor of the auxiliary device 150 may chronologically merge first patient data from the medical device 110 with second patient data from the auxiliary device 150 to create an integrated record.

As similarly shown in FIG. 1A, the devices 110 and 150 may be communicatively coupled via the communication channel 399, as described above. Further, one or more of the devices 110 and 150 may be communicatively coupled with one or more servers 1110 via the communication links 1180 and/or 1190. In an implementation, the device 110 may communicate with the servers 1110 via the device 150. The communicative couplings 1180 and 1190 may each be a wired and/or a wireless communication link. The wired communication links may include a wired electrically coupling, an optical coupling via an optical cable, etc. The wireless communication link may include coupling via a radio frequency or other transmission media and/or via a network such as a local area network, an ad hoc network, a mesh network, a cellular and/or other communication network, a computer network, etc. The communication links 1180 and 1190 may utilize protocols such as, for example, 802.11, ZigBee®, Bluetooth®, etc. In various implementations, the communication links 1180 and/or 1190 may provide secure and/or authenticated communication channels. In an implementation, the devices described herein may encrypt and/or decrypt the data transmitted and/or received via the communication links 1180 and/or 1190.

The components of 120, 121, 130, 144, 145, and 155 of the medical device 110 are communicatively coupled (directly and/or indirectly) to each other for bi-directional communication. Similarly, the components 220, 221, 230, 244, 245, and 255 of the auxiliary device 150 are communicatively coupled (directly and/or indirectly) to each other for bi-directional communication.

Although shown as separate entities in FIG. 14, the one or more of the components of the device 110 and/or 150 may be combined into one or more discrete components and/or may be part of the processor 120 or the processor 220, respectively. The processor 120 and the memory 121 may include and/or be coupled to associated circuitry in order to perform the functions described herein. Similarly, the processor 220 and the memory 221 may include and/or be coupled to associated circuitry in order to perform the functions described herein.

In an implementation, one or more of the devices 110 and 150 may be a therapeutic medical device configured to deliver medical therapy to the patient 101. Thus, each of the devices 110 and 150 may optionally include the therapy delivery control module 155 and 255, respectively. For example, the therapy delivery control module 155 and/or 255 may be an electrotherapy delivery circuit that includes one or more capacitors configured to store electrical energy for a pacing pulse or a defibrillating pulse. The electrotherapy delivery circuit may further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 155 and/or 255 may be a compression device such as an electromechanical controller configured to control a mechanical compression device. As a further example, the therapy delivery control module 155 and/or 255 may be an electromechanical controller configured to control drug delivery, temperature management, ventilation, and/or other type of therapy delivery. Alternatively, one or more of the devices 110 and 150 may be configured to provide patient monitoring and/or diagnostic care without providing medical therapy.

The medical device 110 (e.g., a first medical device) may incorporate and/or be configured to couple to one or more patient interface device(s) 160. The patient interface device(s) 160 may include one or more therapy delivery component(s) 161*a* and one or more sensor(s) 161*b*. The one or more therapy delivery component(s) 161*a* and the one or more sensor(s) 161*b* sensor may provide one or more signals to the medical device 110 via wired and/or wireless connection (s).

The one or more therapy delivery components 161*a* may include electrotherapy electrodes (e.g., the electrotherapy electrodes 166*a*), ventilation device(s) (e.g., the ventilation devices 166*b*), intravenous device(s) (e.g., the intravenous devices 166*c*), compression device(s) (e.g., the compression devices 166*d*), etc. For example, the electrotherapy electrodes may include defibrillation electrodes, pacing electrodes, and/or combinations thereof. The ventilation devices may include a tube, a mask, an abdominal and/or chest compressor (e.g., a belt, a cuirass, etc.), a mechanical ventilator, etc. and combinations thereof. As an example, the mechanical ventilator may be a portable, battery powered ventilator. The intravenous devices may include drug delivery devices, fluid delivery devices, and combinations thereof. The compression devices may include mechanical compression devices such as abdominal compressors, chest compressors, belts, pistons, and combinations thereof. In various implementation, the therapy delivery component(s) 161*a* may be configured to provide sensor data and/or be coupled to and/or incorporate sensors. For example, the electrotherapy electrodes may provide sensor data such as transthoracic impedance, ECG, heart rate, etc. Further the electrotherapy electrodes may include and or be coupled to a chest compression sensor. As another example, the ventilation devices may be coupled to and/or incorporate flow sensors, gas species sensors (e.g., oxygen sensor, carbon dioxide sensor, etc.), etc. As a further example, the intravenous devices may be coupled to and/or incorporate temperature sensors, flow sensors, blood pressure sensors, etc. As yet another example, the compression devices may be coupled to and/or incorporate chest compression sensors, patient position sensors, etc. The therapy delivery control module 155 may be configured to couple to and control the therapy delivery component(s) 161*a*.

In various implementations, the sensor(s) 161*b* may include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal CO2, saturation of muscle oxygen (SMO2), arterial oxygen saturation (SpO2), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos may be two-dimensional or three-dimensional.

The sensor(s) 161*b* may include sensing electrodes (e.g., the sensing electrodes 162), ventilation sensors (e.g., the ventilation sensors 164), temperature sensors (e.g., the temperature sensor 167), chest compression sensors (e.g., the chest compression sensor 168), etc. For example, the sensing electrodes may include cardiac sensing electrodes. The cardiac sensing electrodes may be conductive and/or capacitive electrodes configured to measure changes in a patient's electrophysiology, for example to measure the patient's ECG information. In an implementation, the sensing electrodes may be configured to measure the transthoracic impedance and/or a heart rate of the patient 101. The ventilation sensors may include spirometry sensors, flow sensors, pressure sensors, oxygen and/or carbon dioxide sensors such as, for example, one or more of pulse oximetry sensors, oxygenation sensors (e.g., muscle oxygenation/pH), O2 gas sensors and capnography sensors, and combinations thereof. The temperature sensors may include an infrared thermometer, a contact thermometer, a remote thermometer, a liquid crystal thermometer, a thermocouple, a thermistor, etc. and may measure patient temperature internally and/or externally. The chest compression sensor may include one or more motion sensors including, for example, one or more accelerometers, one or more force sensors, one or more magnetic sensors, one or more velocity sensors, one or more displacement sensors, etc. The chest compression sensor may be, for example, but not limited to, a compression puck, a smart-phone, a hand-held device, a wearable device, etc. The chest compression sensor may be configured to detect chest motion imparted by a rescuer and/or an automated chest compression device (e.g., a belt system, a piston system, etc.). The chest compression sensor may provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes may include or be configured to couple to the chest compression sensor.

The patient data provided at the operational interface and/or playback interface may include the patient data provided via the one or more therapy delivery component(s) 161*a* and/or the one or more sensor(s) 161*b*. For example, the medical device 110 (e.g., the first medical device) may process signals received from the therapy delivery component(s) 161*a* and/or the sensor(s) 161*b* to determine the patient data. Similarly, the auxiliary device 150 may process signals received from the therapy delivery component(s) 261*a* and/or the sensor(s) 261*b* to determine the patient data.

In various implementations, the auxiliary device 150 may be a medical device (e.g., a second medical device) or a computing device (e.g., personal computer, a laptop computer, a mobile device, a hand-held device, a wireless device, a tablet computer, a wearable device such as a wrist-worn device, a head-worn device, heads up display, etc., or combinations thereof) adapted for medical use. In an implementation, the auxiliary device 150 may include a computing device and/or a medical device configured for telemetry. The auxiliary device 150 may incorporate and/or be configured to couple to one or more patient interface device(s) 260. The patient interface device(s) 260 may include one or more therapy delivery components 261*a* and one or more sensors 261*b*. The therapy delivery component (s) 261*a* may be substantially as described herein with regard to the therapy delivery component(s) 161*a*. Similarly, the sensor(s) 261*b* may be substantially as described herein with regard to the sensor(s) 161*b*. The auxiliary device 150 may receive patient data in a manner substantially similar to that described herein for the medical device 110. For example, the device 210 may receive the patient data based on signals received from the therapy delivery component(s) 261*a* and the sensor(s) 261*b*.

Figure 15:
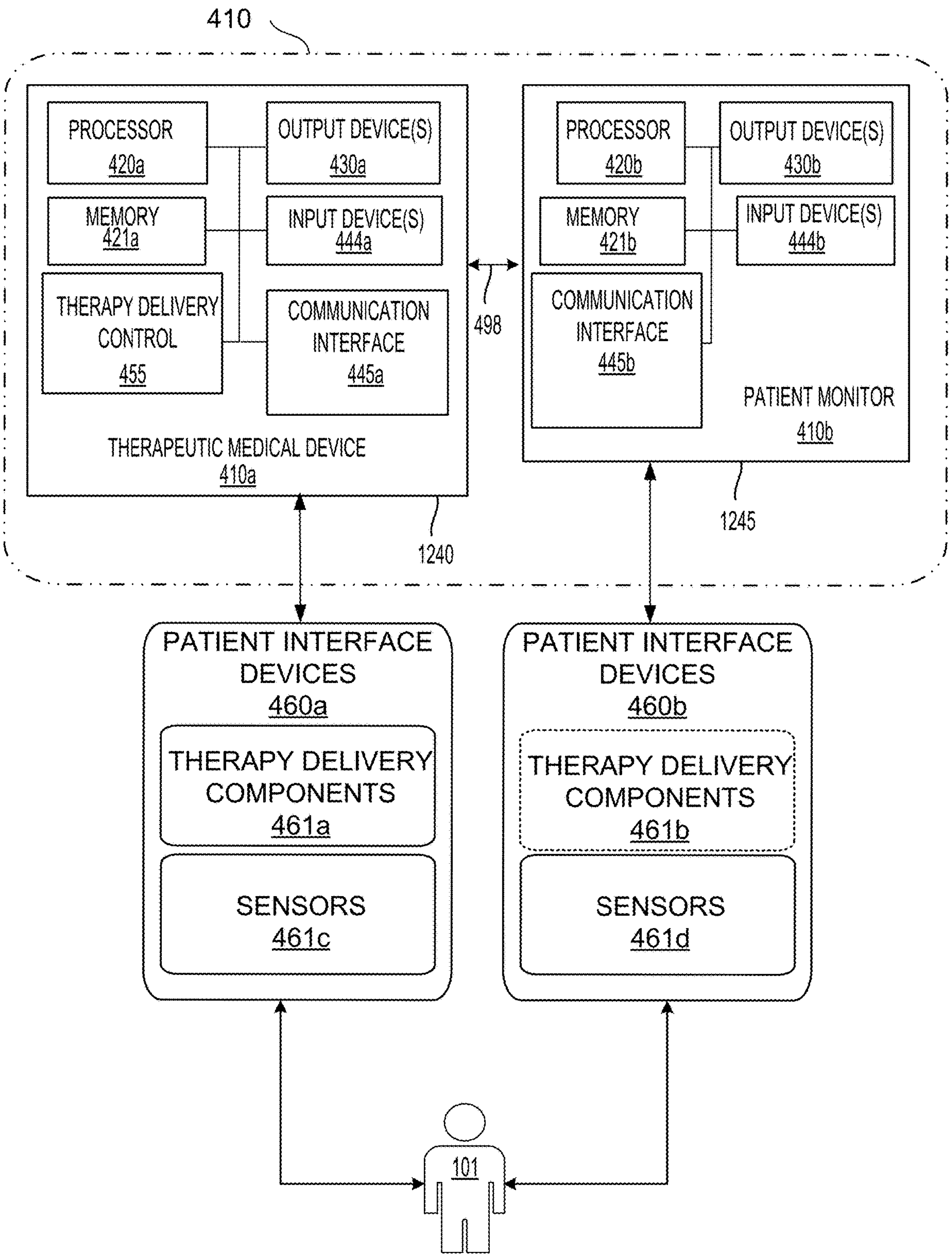
FIG. 15 shows examples of components of a modular therapeutic medical device/patient monitor.

Referring to FIG. 15, a schematic diagram of a modular therapeutic medical device/patient monitor is shown. The modular therapeutic medical device/patient monitor 410 may include a therapeutic medical device 410*a* and patient monitor 410*b*. In various implementations, one or both of the devices 110 and 150 may be the modular therapeutic medical device/patient monitor 410. In an implementation, the therapeutic medical device 410*a* may be a defibrillator and may be a professional defibrillator (e.g., an advanced defibrillator). In an implementation, the patient monitor 410*b* may be an advanced critical care monitor. The modular therapeutic medical device/patient monitor 410 may be a defibrillator and a patient monitor configured to communicatively couple to one another.

The dotted line associated with the index number 410 indicates that the therapeutic medical device 410*a* and the patient monitor 410*b* may be functionally joined but are not physically contained within a single housing. Rather, the therapeutic medical device 410*a* and the patient monitor 410*b* are disposed in physically separate housings (e.g., the housing 1240 and the housing 1245). As such, the therapeutic medical device 410*a* and the patient monitor 410*b* may be used together or individually as discussed further below. The therapeutic medical device 410*a* and the patient monitor 410*b* may communicate via a wired and/or wireless communicative coupling 498. The first housing 1240 may surround, at least in part, components of the therapeutic medical device 410*a* configured to support therapy delivery and receive sensor signals via the therapy delivery components 461*a* and the one or more sensors 461*c*. The second housing 1245 may surround, at least in part, components of the patient monitor 410*b* configured to support patient monitoring via the one or more sensors 461*d*. In contrast to the components surrounded, at least in part, by the first housing 1240, the components surrounded by the second housing 1245 may exclude the components configured to support therapy delivery via the therapy delivery components 461*a*.

The modular therapeutic medical device/patient monitor 410 may provide therapy and/or monitor the patient 101 via the patient interface devices 460*a* and 460*b*. The patient interface devices 460*a* and 460*b* may be substantially as described with regard to the patient interface devices 160. The patient interface devices 460*a* may include therapy delivery components 461*a* and/or sensor devices 461*c*. The patient interface devices 460*b* may monitor the patient 101 via the sensor devices 461*d*.

The therapeutic medical device 410*a* may be configured to provide therapy to the patient 101 via the one or more therapy delivery components 461*a*. In an implementation, the one or more therapy delivery components 461*a* may include defibrillation electrodes. The defibrillation electrodes may include and/or be configured to function as sensing electrodes. The sensors 461*c* may include sensing electrodes, for example, 12-lead electrodes configured to provide ECG data.

The therapeutic medical device 410*a* may monitor the patient 101 and collect patient data (e.g., via the therapy delivery component(s) 461*a* and/or the sensor(s) 461*c*). The patient data may include one or more of treatment data, sensor data, resuscitation/care data, and/or combinations thereof. The therapy delivery component(s) 461*a* may be substantially as described with regard to the therapy delivery component(s) 161*a* and the sensor device(s) 461*c* may be substantially as described with regard to the sensor device(s) 161*b*.

In an implementation, the patient monitor 410*b* may exclude therapy delivery capabilities and patient interface devices 460*b* may exclude therapy delivery components. The patient monitor 410*b* may be configured to monitor the patient 101 via the one or more sensors 461*d*. The patient monitor 410*b* may be configured to collect the patient data via the one or more sensors 461*d*. The patient data may include one or more of treatment data, sensor data, resuscitation/care data, and/or combinations thereof. The one or more sensors 461*d* may generate signals indicative of ECG and/or other cardiac parameters, ventilation parameters, drug and/or fluid delivery parameters, etc.

Optionally, the patient monitor 410*b* may be configured to provide a different therapy to the patient 101 than the therapeutic medical device 410*a* via the therapy delivery components 461*b*. For example, the therapeutic medical device 410*a* may provide defibrillation therapy to the patient 101 and the patient monitor 410*b* may exclude the capability of providing defibrillation therapy but may be configured to provide ventilation therapy, drug and/or fluid delivery therapy, etc.

Although shown together in FIG. 15, each of the therapeutic medical device 410*a* and the patient monitor 410*b* may perform all of their respective therapy and/or monitoring functions with or without the other of the therapeutic medical device 410*a* and the patient monitor 410*b*. Thus, the caregiver 102*a* and/or 102*b* (e.g., as shown in FIG. 1A) may use the therapeutic medical device 410*a* alone (e.g., without the patient monitor 410*b*) or in combination with the patient monitor 410*b*. Similarly, the caregiver 102*a* and/or 102*b* may use the patient monitor 410*b* alone (e.g., without the therapeutic medical device 410*a*) or in combination with the therapeutic medical device 410*a*.

For simplicity in FIG. 15, the therapeutic medical device 410*a* and the patient monitor 410*b* are shown as corresponding to one patient 101. However, in an implementation, the therapeutic medical device 410*a* and the patient monitor 410*b* may correspond to two different patients (e.g., a first patient and a second patient) since these devices may be used independently and do not have to be used in conjunction with one another. Thus, the therapeutic medical device 410*a* may provide therapy to and/or monitor a first patient and the patient monitor 410*b* may provide therapy to and/or monitor a second patient.

The therapeutic medical device 410*a* and the patient monitor 410*b* may be configured to automatically pair with one another via the communication connection 498. Further, each of the therapeutic medical device 410*a* and the patient monitor 410*b* may be configured to share data with the other of the therapeutic medical device 410*a* and the patient monitor 410*b* via the communication connection 498. The communication connection 498 may enable the therapeutic medical device 410*a* and the patient monitor 410*b* to provide therapy and monitor the same patient 101 cooperatively.

As shown in FIG. 15, the therapeutic medical device 410*a* may include a processor 420*a*, a memory 421*a*, one or more output devices 430*a*, one or more input devices 444*a*, and a communication interface 445*a*. The patient monitor 410*b* may include a processor 420*b*, a memory 421*b*, one or more output devices 430*b*, one or more input devices 444*b*, and a communication interface 445*b*. Although shown as separate entities, the components of the therapeutic medical device 410*a* and/or the patient monitor 410*b* 420*a*, 421*a*, 445*a*, may be combined into one or more discrete components and/or may be part of the processor 420*a* and/or 420*b*. The processor 420*a* and the memory 421*a* may include and/or be coupled to associated circuitry in order to perform the functions described herein. Similarly, the processor 420*b* and the memory 421*b* may include and/or be coupled to associated circuitry in order to perform the functions described herein. The components 420*a*, 421*a*, 430*a*, 444*a*, 445*a*, and 455 are communicatively coupled (directly and/or indirectly) to each other for bi-directional communication. Similarly, the components 420*b*, 421 *b*, 430*b*, 444*b*, and 445*b* are communicatively coupled (directly and/or indirectly) to each other for bi-directional communication The therapy delivery control module 455 may be an electrotherapy delivery circuit substantially as described with regard to the therapy delivery control modules 155 and 255. As another example, the therapy delivery control module 455 may be a compression device such as an electro-mechanical controller configured to control a mechanical compression device. As a further example, the therapy delivery control module 455 may be an electro-mechanical controller configured to control drug delivery, temperature management, ventilation, and/or other type of therapy delivery. Optionally, the patient monitor 410*b* may be configured to control the therapy delivery components 461*b* and/or to communicatively couple to another device configured to control these components.

The medical device (e.g., the medical device 110 or the auxiliary device 150) may be, for example, but not limited to, one or more of a patient monitor, a defibrillator, a mechanical chest compression device (e.g., an automated chest compression device, a belt-based chest compression device, a piston-based chest compression device, a hand-held chest compression device for mechanically assisted chest compressions, an active compression-decompression device, or combinations thereof), a ventilator, an intravenous cooling device, and/or combinations thereof. The medical device may be a wearable device. The medical device may include or be coupled to a patient monitor. The ventilator may be a mechanical ventilator. The mechanical ventilator may be a portable, battery-powered ventilator. The intravenous cooling device may deliver cooling therapy and/or may sense a patient's temperature. The medical device may provide, for example, but not limited to, one or more of electrical therapy (e.g., defibrillation, cardiac pacing, synchronized cardioversion, diaphragmatic stimulation, phrenic nerve stimulation, etc.), ventilation therapy, therapeutic cooling, temperature management therapy, invasive hemodynamic support therapy (e.g., extracorporeal membrane oxygenation (ECMO)), and/or combinations thereof. The medical device may incorporate and/or couple (e.g., mechanically, electrically, and/or communicatively) to one or more sensors (e.g., the patient interface devices 160 and/or 260). The sensors may include, for example, but not limited to, cardiac sensing electrodes, chest compression sensor(s), ventilation sensor(s), and/or one or more sensors capable of providing signals indicative of one or more of vital sign(s), electrocardiogram (ECG), blood pressure (e.g., invasive blood pressure (IBP), non-invasive blood pressure (NIBP)), heart rate, pulse oxygen level, respiration rate, heart sounds, lung sounds, respiration sounds, end tidal CO2, saturation of muscle oxygen (SMO2), arterial oxygen saturation (SpO2), cerebral blood flow, electroencephalogram (EEG) signals, brain oxygen level, tissue pH, tissue oxygenation, tissue fluid levels, and/or one or more sensors capable of providing signals indicative of one or more parameters determined via ultrasound, near-infrared reflectance spectroscopy, pneumography, cardiography, ocular impedance, spirometry, tonometry, plethysmography, eye tracking, chest compression parameters (e.g., compression depth, compression rate, compression release, release velocity, distance of active release for active compression-decompression, etc.), ventilation parameters, respiratory parameters, drug delivery parameters, fluid delivery parameters, transthoracic impedance, blood sampling, venous pressure monitoring (e.g., CVP), temperature, pulse oximetry, non-invasive hemoglobin parameters, and/or combinations thereof. In various implementations, the one or more sensors may also provide therapy.

Referring to FIGS. 14 and 15, the processors 120, 220, 420*a*, and 420*b* are physical processors (i.e., an integrated circuit configured to execute operations on the devices 110, 150, 410*a*, and 410*b*, respectively, as specified by software and/or firmware stored in a computer storage medium). The processors 120, 220, 420*a*, and 420*b* are operably coupled, respectively, to the memory 121, the memory 221, the memory 421*a*, and the memory 421*b*. The processors 120, 220, 420*a*, and 420*b* may be intelligent hardware devices (for example, but not limited to, a central processing unit (CPU), a graphics processing unit (GPU), one or more microprocessors, a controller or microcontroller, an application specific integrated circuit (ASIC), a digital signal processor (DSP), etc.) designed to perform the functions described herein and operable to carry out instructions on the devices 110, 150, 410*a*, and 410*b*, respectively. Each of the processors 120, 220, 420*a*, and 420*b* may be one or more processors and may be implemented as a combination of hardware devices (e.g., a combination of DSP and a microprocessor, a plurality of microprocessors, one or more microprocessors in conjunction with a DSP core, or another such configuration). Each of the processors 120, 220, 420*a*, and 420*b* may include multiple separate physical entities that may be distributed in the devices 110, 150, 410*a*, and 410*b* respectively. Each of the processors 120, 220, 420*a*, and 420*b* is configured to execute processor-readable, processor-executable software code containing one or more instructions or code for controlling the processors 120, 220, 420*a*, and 420*b* to perform the functions as described herein. The processors 120, 220, 420*a*, and/or 420*b* may utilize various architectures including but not limited to a complex instruction set computer (CISC) processor, a reduced instruction set computer (RISC) processor, or a minimal instruction set computer (MISC). In various implementations, the processors 120, 220, 420*a* and/or 420*b* may be a single-threaded or a multi-threaded processor. The processors 120, 220, 420*a*, and/or 420*b* may be, for example, but not limited to, an Intel® Itanium® or Itanium 2@processor(s), AMD® Opteron®, Athlon MP® processor(s), a Motorola® line of processor, or an ARM, Intel Pentium Mobile, Intel Core i5 Mobile, AMD A6 Series, AMD Phenom II Quad Core Mobile, or like devices.

The medical device 110 and/or the auxiliary device 150 may include a patient interface device signal processor 156 and 256, respectively. The patient interface device signal processor 156 and 256 may include A/D converters and other hardware configured to receive and process signals from the patient interface devices 160 and 260, respectively. In an implementation, the processor 120 may include the patient interface device signal processor 156 and/or the processor 220 may include the patient interface device signal processor 256.

The memories 121, 221, 421*a*, and 421*b* refer generally to a computer storage medium, including but not limited to RAM, ROM, FLASH, disc drives, fuse devices, and portable storage media, such as Universal Serial Bus (USB) flash drives, etc. Each of the memories 121, 221, 421*a*, and 421*b* may include, for example, random access memory (RAM), or another dynamic storage device(s) and may include read only memory (ROM) or another static storage device(s) such as programmable read only memory (PROM) chips for storing static information such as instructions for a coupled processor (e.g., one of the processors 120, 220, 420*a*, and 420*b*). The memories 121, 221, 421*a*, and 421*b* may include USB flash drives that may store operating systems and other applications.

The USB flash drives may include input/output components, such as a wireless transmitter and/or USB connector that can be inserted into a USB port of another computing device. The memories 121, 221, 421*a*, and/or 421*b* may be long term, short term, or other memory associated with the respective device 110, 150, 410*a*, and 410*b* and are not to be limited to a particular type of memory or number of memories, or type of media upon which memory is stored. The memories 121, 221, 421*a*, and/or 421*b* include a non-transitory processor-readable storage medium (or media) that stores the processor-readable, processor-executable software code. The memories 121, 221, 421*a*, and/or 421*b* may store information and instructions. For example, the memories 121, 221, 421*a*, and/or 421*b* may include flash memory and/or another storage media may be used, including removable or dedicated memory in a mobile or portable device. As another example, hard disks such as the Adaptec® family of SCSI drives, an optical disc, an array of disks such as RAID (e.g. the Adaptec family of RAID drives), or other mass storage devices may be used. The memories 121, 221, 421*a*, and/or 421*b* may include removable storage media such as, for example, external hard-drives, floppy drives, flash drives, zip drives, compact disc-read only memory (CD-ROM), compact disc-re-writable (CD-RW), or digital video disk-read only memory (DVD-ROM).

The communication interfaces 145, 245, 445*a*, and 445*b* may transmit and/or receive information to and/or from one or more devices external to and communicatively coupled to the devices 110, 150, 410*a*, and 410*b*, respectively. In an implementation, the communication interface 145 may include a transmission buffer 122*a* and/or a reception buffer 122*b*. In an implementation, the communication interface 245 may include a transmission buffer 222*a* and/or a reception buffer 222*b*. The transmission buffers 122*a* and 222*a* may hold data prepared for transmission and may monitor and/or control data encoding rates for preparing data for transmission and/or release rates of data to the communication channel 399 (e.g., a transmission rate from the medical device 110 and/or from the auxiliary device 150). The reception buffers 122*b* and 222*b* accumulate incoming transmitted data and hold the transmitted data until the processor 120 or 220, respectively, are ready to process the transmitted data.

The communication interfaces 145, 245, 445*a*, and 445*b* may transmit and/or receive the information via a wired and/or wireless communicative coupling (e.g., 399, 1190, and/or 1180). The information may include information stored in at least one of the memories 121, 221, 421*a*, and 421*b*. The information may include, for example, but not limited to, resuscitative treatment information, physiological information, patient information, rescuer and/or caregiver information, location information, rescue and/or medical treatment center information, etc. The communication interfaces 145, 245, 445*a*, and/or 445*b* may enable short-range and/or long-range wireless communication capabilities which may include communication via near field communication, ZigBee®, Wi-Fi, Bluetooth®, satellite(s), radio waves, a computer network (e.g., the Internet), a cellular network, etc. The communication interfaces 145, 245, 445*a*, and/or 445*b* may enable communication via a network such a Local Area Network (LAN), Wide Area Network (WAN), a mesh network, an ad hoc network, or another network. The communication interfaces 145, 245, 445*a*, and/or 445*b* may include, for example, an RS-232 port for use with a modem based dialup connection, a copper or fiber 10/100/1000 Ethernet port, or a Bluetooth® or WiFi interface.

In an implementation, the communication interfaces 145, 245, 445*a*, and/or 445*b* may enable communication between one or more of the devices 110, 150, 410*a*, and 410*b* and one or more servers 1110. For example, the one or more servers 1110 may be remote servers and may include a cloud server and/or a central facility server. In an implementation, the one or more servers 1110 may be associated with a medical provider (e.g., a hospital, a physician's office, a medical records office, an emergency services office, an emergency services vehicle, a dispatch center, etc.).

In an implementation, the communication interface 445*b* may enable the patient monitor 410*b* to communicatively couple with multiple therapeutic medical device(s) 410*a* and/or with another patient monitor. The patient monitor 410*b* may merge the received patient data and/or other information with patient data and/or other information collected by and/or generated at the patient monitor 410*b* to create an integrated record. In an implementation, the therapeutic medical device 410*a* may communicatively couple with the one or more servers 1110 via the patient monitor 410*b* and the communication interface 445*b*. In an implementation, the patient monitor 410*b* may provide the integrated record to the one or more servers 1110. Alternatively or additionally, the therapeutic medical device 410*a* may provide patient data and/or other information to the one or more servers 1110 via the communication interface 445*a* independently from the communication interface 445*b*.

The output device(s) 130 and user input device(s) 144 may be included in the medical device 110 and/or coupled to the medical device 110. Similarly, the output device(s) 230 and the user input device(s) 244 may be included in the auxiliary device 150 and/or coupled to the auxiliary device 150, the output device(s) 430*a* and the user input device(s) 444*a* may be included in the therapeutic medical device 410*a* and/or coupled to the therapeutic medical device 410*a*, and the output device(s) 430*b* and the user input device(s) 444*b* may be included in the patient monitor 410*b* and/or coupled to the patient monitor 410*b*. The output device(s) 130, 230, 430*a*, and/or 430*b* may include one or more of a display (e.g., the displays 115*a*, 115*b*), a speaker (e.g., the speaker 82), and a haptic device. The display may be a display screen. The auxiliary device may provide at least one first display screen and the medical device may provide at least one second display screen. The display may provide a graphical user interface (GUI). The display may be, for example, but not limited to, a liquid crystal display (LCD) and/or a light emitting diode (LED) display. In an implementation, the output device(s) 130, 230, 430*a*, and/or 430*b* may be input/output device(s) capable of capturing user input. For example, the display (e.g., 115*a* and/or 115*b*) may be a touchscreen. The touchscreen may be, for example, a pressure sensitive touchscreen or a capacitive touchscreen. The touchscreen may capture user input provided via touchscreen gestures and/or provided via exertions of pressure on a particular area of the screen. Examples of touchscreen gestures that may enable user input may include pushing on the touchscreen to exert pressure that exceeds a particular threshold to indicate an input to a pressure sensitive touchscreen by the user. The touchscreen and the controlling processor (e.g., 120, 220, 420*a*, and/or 420*b*) may be configured recognize touchscreen gestures including, for example, but not limited to, tap, double tap, caliper gesture, drag and drop, slide, press and drag, hold and press, etc. In an implementation, the processors 120, 220, 420*a*, and/or 420*b* may control a respective display to provide visual representations of data captured by and/or received at the device 110, 150, 410*a*, and/or 410*b*. The visual representations may include still images and/or video images (e.g., animated images).

In an implementation, the output device(s) 130, 230, 430*a*, and 430*b* and/or the input device(s) 144, 244, 444*a*, and 444*b* may include wearable devices such as, for example, a heads-up display mounted onto eyeglasses, a face shield, a watch, and/or devices that may be integrated with other wearable communication devices, such as, for example, an ear bud or a Bluetooth® hands free phone adaptor. The processors 120, 220, 420*a*, and 420*b* may control the output devices 130, 230, 430*a*, and 430*b* respectively, to provide information for the user. The information may include feedback (e.g., visible feedback, audible feedback, haptic feedback, textual feedback, numerical feedback, and graphical feedback) such as CPR feedback.

The one or more user input devices 144, 244, 444*a*, and 444*b* may include, for example, a keyboard, a mouse, joystick, trackball, or other pointing device, a microphone, a camera, etc. Further, the user input devices 144, 244, 444*a*, and 444*b* may be a touchscreen and/or another input/output device capable of providing information for the user and capturing information from the user. The touchscreen may be a pressure sensitive touchscreen.

In an implementation, the user input devices 144, 244, 444*a*, and/or 444*b* may be configured to capture information, such as, for example, patient medical history (e.g., medical record information including age, gender, weight, body mass index, family history of heart disease, cardiac diagnosis, co-morbidity, left ventricular ejection fraction, medications, previous medical treatments, and/or other physiological information), physical examination results, patient identification, caregiver identification, healthcare facility information, etc.

The processor, memory, communication interfaces, input and/or output devices and other components described above are meant to exemplify some types of possibilities. In no way should the aforementioned examples limit the scope of the disclosure, as they are only exemplary embodiments of these components.

Various modifications and additions can be made to the exemplary embodiments discussed without departing from the scope of the present disclosure. For example, while the embodiments described above refer to particular features, the scope of the disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A system for review of clinical data comprising:

a medical device configured to receive signals indicative of patient data from one or more patient interface devices coupled to the medical device; and at least one auxiliary device configured to communicatively couple to the medical device via a communication channel, the at least one auxiliary device comprising:

at least one output device, a memory, a communication interface, and at least one processor coupled to the memory, the at least one output device, and the communication interface, wherein the at least one processor is configured to:

establish the communication channel with the medical device, receive machine state information from the medical device, receive the patient data from the medical device via the communication channel, determine a patient data age, select a patient data age threshold based on the received machine state information, compare the patient data age to the patient data age threshold to determine an indication of the patient data age, and control the at least one output device to provide the patient data and the indication of the patient data age.

2. The system of claim 1, wherein the memory comprises at least one look-up table that includes patient data age thresholds, wherein each patient data age threshold in the at least one look-up table corresponds to a particular patient data context, and wherein the at least one-first processor is configured to select the patient data age threshold based on the at least one look-up table.

3. The system of claim 1 wherein the patient data age threshold is a range of acceptable patient data ages.

4. The system of claim 1 wherein the patient data age threshold is a maximum acceptable patient data age.

5. The system of claim 1 wherein the at least one processor is configured to select the patient data age threshold further based on a patient data context that corresponds to a patient data type.

6. The system of claim 5 wherein the at least one-first processor is configured to identify the patient data type.

7. The system of claim 6 wherein the patient data type comprises ECG data indicative of a particular physiological condition.

8. The system of claim 7 wherein the particular physiological condition comprises ventricular fibrillation, ventricular tachycardia, or atrial fibrillation.

9. The system of claim 5 wherein the patient data context corresponds to a particular combination of (a) a machine state of the medical device as defined by the machine state information and (b) the patient data type.

10. The system of claim 1 wherein the machine state information indicates one or more of a machine configuration or an operational mode.

11. The system of claim 1 wherein the at least one-first processor is configured to determine a relative location of the medical device and the at least one auxiliary device and select the patient data age threshold based on the relative location.

12. The system of claim 11, wherein the relative location of the medical device and the at least one auxiliary device comprises a proximate relative location or a remote relative location, wherein the memory comprises a first look-up table that includes first patient data age thresholds for the proximate relative location and a second look-up table that includes second patient data age thresholds for the remote relative location, wherein each patient data age threshold in the first and second look-up tables corresponds to a particular patient data context, and wherein the at least one processor is configured to select the patient data age threshold from the first look-up table or the second look-up table based on the relative location.

13. The system of claim 11 wherein the at least one-first processor is configured to determine the relative location based on one or more characteristics of the communication channel.

14. The system of claim 1 wherein the at least one output device comprises a display screen and the indication of the patient data age comprises one or more user interface features indicative of a comparison between the patient data age and the patient data age threshold.

15. The system of claim 1 wherein the communication channel comprises one or more of a wired or a wireless communication channel.

16. The system of claim 1 wherein the medical device comprises a defibrillator or a defibrillator/patient monitor.

17. The system of claim 1 wherein the medical device comprises a defibrillator and a patient monitor configured to communicatively couple to one another.

18. The system of claim 1 wherein the medical device comprises a first medical device and the at least one auxiliary device comprises a second medical device.

19. The system of claim 1 wherein the medical device comprises a near field communication tag configured to establish the communication channel between the medical device and the at least one auxiliary device in response to a proximate location of the at least one auxiliary device relative to the medical device.

20. The system of claim 1, further comprising a data display window configured to provide a visual representation of the patient data, wherein the visual representation of the patient data comprises one or more of waveforms, time trends, or discrete physiological measurements for one or more of cardiac parameters or ventilation parameters.

21. The system of claim 1, further comprising a data display window configured to provide a visual representation of the patient data, wherein the visual representation of the patient data comprises one or more of a textual, numerical, or graphical representation of cardiopulmonary resuscitation (CPR) performance data.

22. The system of claim 21 wherein the CPR performance data comprises one or more of a compression depth, a compression rate, a chest release indicator, a perfusion performance indicator, or a CPR time indicator.

23. The system of claim 1, further comprising:

a data display window configured to provide a visual representation of the patient data; and an interactive timeline configured to capture user input indicative of a time interval selection of the visual representation of the patient data, wherein the interactive timeline comprises:

a first time interval selector configured to indicate a start time of the visual representation of the patient data, and a second time interval selector configured to indicate an end time of the visual representation of the patient data, and wherein the first time interval selector and the second time interval selector are configured to move along the interactive timeline in response to the user input.

24. The system of claim 1, further comprising:

a data display window configured to provide a visual representation of the patient data; and an interactive timeline configured to capture user input indicative of a time interval selection of the visual representation of the patient data, wherein the interactive timeline comprises one or more visual event indicators and is configured to capture a user selection of at least one visual event indicator of the one or more visual event indicators.

25. The system of claim 24 wherein the data display window is configured to provide the visual representation of the patient data that corresponds to the user selected at least one visual event indicator.

26. The system of claim 1 further comprising:

a data display window configured to provide a visual representation of the patient data; and a media navigation bar configured to capture user input indicative of data display parameters and to control the visual representation of the patient data based on the user input wherein the media navigation bar comprises user interactive data display controls configured to enable a user to control playback of the patient data, the user interactive data display controls comprising one or more of a rewind control, a play control, a stop control, a pause control, and a fast forward control, a skip back control, or a and skip forward control.

27. The system of claim 1 wherein the at least one auxiliary device is configured as a telemedicine auxiliary device.

28. The system of claim 1 wherein the at least one processor is further configured to estimate a transmission age for the patient data.

29. The system of claim 28 wherein the patient data age is determined based on at least one of the transmission age and a playback selection age.

30. The system of claim 1 wherein the at least one processor is further configured to:

estimate a round-trip time (RTT) for the communication channel after establishing the communication channel; and determine a transmission age for the patient data using the RTT.

31. The system of claim 30 wherein the at least one processor is further configured to:

estimate an updated transmission age for the patient data; and a update the previously determined transmission age for the patient data.

* * * * *